(12) United States Patent
Ali et al.

(10) Patent No.: US 8,119,806 B2
(45) Date of Patent: Feb. 21, 2012

(54) CICLETANINE DERIVATIVES

(75) Inventors: Amjad Ali, Freehold, NJ (US); Iyassu K. Sebhat, Jersey City, NJ (US); Christopher L. Franklin, Quincy, MA (US); Kathleen M. Rupprecht, Cranford, NJ (US); Robert K. Baker, Cranford, NJ (US); Ravi P. Nargund, East Brunswick, NJ (US); Lin Yan, East Brunswick, NJ (US); Pei Huo, Millburn, NJ (US); Dong-Ming Shen, Edison, NJ (US); Nicoletta Almirante, Milan (IT); Stefano Biondi, Pero (IT); Massimiliano Ferrario, Ceriano Laghetto (IT); Alessia Nicotra, Grandate (IT)

(73) Assignee: Merck Sharp & Dohme Corp., Rahway, NJ (US)

( * ) Notice: Subject to any disclaimer, the term of this patent is extended or adjusted under 35 U.S.C. 154(b) by 297 days.

(21) Appl. No.: 12/509,698

(22) Filed: Jul. 27, 2009

(65) Prior Publication Data

US 2010/0029678 A1    Feb. 4, 2010

Related U.S. Application Data

(60) Provisional application No. 61/137,250, filed on Jul. 29, 2008, provisional application No. 61/189,034, filed on Aug. 15, 2008.

(51) Int. Cl.
*A61K 31/4355* (2006.01)
*C07D 491/048* (2006.01)

(52) U.S. Cl. .......................... 546/115; 514/302

(58) Field of Classification Search .................. None
See application file for complete search history.

(56) References Cited

U.S. PATENT DOCUMENTS

2005/0059655 A1    3/2005    Garvey et al.

FOREIGN PATENT DOCUMENTS

| WO | WO2004110432 | 12/2004 |
| WO | WO2005023182 | 3/2005 |
| WO | WO2008075245 | 6/2008 |

OTHER PUBLICATIONS

Fodor et al.; "Review of Three Studies to Determine the Efficacy and Tolerance of Cicletanine in the Short- and Long-Term Treatment of Essential Hypertension"; Drugs Under Expirimental and Clinical Research, Bioscience Ediprint Inc, XX, vol. 14, No. 2-3; Jan. 1, 1988; pp. 195 -204, XP008101555; p. 195.
EPO Search Report for WO2010/014516; Completed, Oct. 6, 2009; Performed by Authorized officer Elena Marzi.

*Primary Examiner* — David K O Dell
(74) *Attorney, Agent, or Firm* — Richard S. Parr; Catherine D. Fitch; Mark R. Daniel

(57) ABSTRACT

A compound having the structure wherein
X is selected from the group consisting of:
a bond, $-NHCH_2(CH_2)_nCH_2OC(O)-$, $-CH_2NHC(O)$ $CH_2NHC(O)-$, $-CH_2OC(O)-$, $-OCH(CH_3)OC(O)-$, $-OCH_2OC(O)-$,
$-O-$, $-NR^1-$, $-CR^1R^3-$, $-(CH_2)_p-$, $-(CH_2)_qNR^1C(O)-$, $-CHR^5NR^2C(O)-$, $-(CH_2)_qC(O)-$, $-(CH_2)_qC(O)NR^1-$, or a pharmaceutically acceptable salt thereof, and methods of using the compounds for treating hypertension.

12 Claims, No Drawings

CICLETANINE DERIVATIVES

PRIORITY CLAIM

This application claims the benefit of U.S. Provisional Application No. 61/137,250, filed Jul. 29, 2008 and also claims benefit of U.S. Provisional Application No. 61/189,034 filed Aug. 15, 2008.

JOINT RESEARCH AGREEMENT

The claimed invention was made as a result of activities undertaken within the scope of a joint research agreement between Merck & Co., Inc. and NicOx SA. The agreement was executed on Mar. 20, 2006.

BACKGROUND OF THE INVENTION

US 2005/0059655 describes nitrosated and nitrosylated furosemide derivatives (examples 1-16) having one or two nitroxy groups attached. The compounds are described as useful for treating conditions resulting from excessive water retention, cardiovascular disease, diabetes, oxidative stress, endothelial dysfunction, cirrhosis, pre-eclampsia, osteoporosis, and nephropathy.

U.S. Pat. No. 4,383,998 genetically claims cicletanine. U.S. Pat. No. 5,026,855 claims the (+) enantiomer of cicletanine and compositions comprising the (+) enantiomer, and methods of preparation.

SUMMARY OF THE INVENTION

The present invention includes nitric oxide linked cicletanine, and derivatives thereof, including various pharmaceutically acceptable salts and hydrates of these forms, and pharmaceutical formulations for controlled and sustained delivery of these forms to a patient. The salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy, comprising administering a compounds of the invention to a patient having such a condition, or being at risk to having such condition.

DETAILED DESCRIPTION OF THE INVENTION AND PREFERRED EMBODIMENTS

Compounds of the invention have the general formula I:

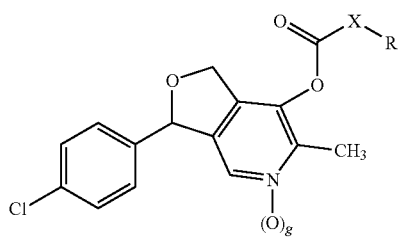

wherein
X is selected from the group consisting of:
a bond, —NHCH$_2$(CH$_2$)$_n$CH$_2$OC(O)—, —CH$_2$NHC(O)CH$_2$NHC(O)—, —CH$_2$OC(O)—, —OCH(CH$_3$)OC(O)—, —OCH$_2$OC(O)—,
—O—, —NR$^1$—, —CR$^1$R$^3$—, —(CH$_2$)$_p$—, —(CH$_2$)$_q$NR$^1$C(O)—, —CHR$^5$NR$^2$C(O)—, —(CH$_2$)$_q$C(O)—, —(CH$_2$)$_q$C(O)NR$^1$—,

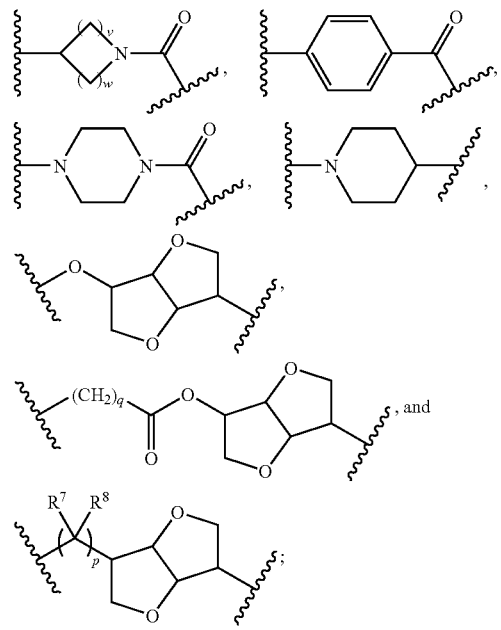

R$^1$, R$^2$, R$^7$ and R$^8$, each instance in which they occur, are independently selected from the group consisting of hydrogen and C$_{1-7}$ alkyl;
R$^3$ is hydrogen, C$_{1-4}$ alkyl, —CH$_2$ONO$_2$, or —ONO$_2$;
R$^5$ and R$^9$ are independently selected from the group consisting of hydrogen, —CH$_3$, —CH$_2$CH$_3$, —CH(CH$_3$)$_2$, —C(CH$_3$)$_3$, —CH$_2$OH, —CH(OH)CH$_3$, and —CH$_2$C$_6$H$_5$;
g is 0 or 1;

p is 0, 1, 2, 3, 4, 5, 6, or 7;
q is 1, 2, 3, 4, or 5;
v and w are independently selected from the group consisting of 0, 1, 2, and 3, provided that
v+w is 1, 2, 3 or 4;
R is selected from the group consisting of
—(CH$_2$)$_x$CH(ONO$_2$)(CH$_2$)$_y$CH$_3$,
—(CH$_2$)$_x$CH(ONO$_2$)(CH$_2$)$_y$CH(ONO$_2$)(CH$_2$)$_z$CH$_3$,
—(CH$_2$)$_x$CH(ONO$_2$)(CH$_2$)$_y$CH$_2$(ONO$_2$),
—(CH$_2$)$_x$CH(ONO$_2$)(CR$^1$R$^2$)CH$_2$(ONO$_2$),
—CR$^1$R$^2$R$^3$, with the proviso that R$^3$ is —CH$_2$ONO$_2$ or —ONO$_2$,
—(CH$_2$)$_x$(ONO$_2$),
—O—C(O)—(CH$_2$)$_x$CH(ONO$_2$)(CH$_2$)$_y$CH$_2$(ONO$_2$),

[structure]

with the proviso that X is CR$^1$R$^3$ and R$^3$ is —CH$_2$ONO$_2$ or —ONO$_2$,

[structures]

provided that when R is
—O—C(O)—(CH$_2$)$_x$CH(ONO$_2$)(CH$_2$)$_y$CH$_2$(ONO$_2$) or

[structure]

then X is selected from the group consisting of a bond,
—NR$^1$—, —CR$^1$R$^3$—, —(CH$_2$)$_p$—, —(CH$_2$)$_q$NR$^1$C(O)—,
—CHR$^5$NR$^2$C(O)—, —(CH$_2$)$_q$C(O)—, —(CH$_2$)$_q$C(O)NR$^1$,

[structures]

h, j, and k are independently selected from the group consisting of 0, 1, and 2;
m, n, x, y, and z are independently selected from the group consisting of 0, 1, 2, 3, and 4;
r and s are independently selected from the group consisting of 0, 1, 2, and 3, provided that
r+s is 1, 2, 3 or 4.

In one embodiment, formula I is selected from the group consisting of

[structures]

In another embodiment of the invention, X is selected from the group consisting of

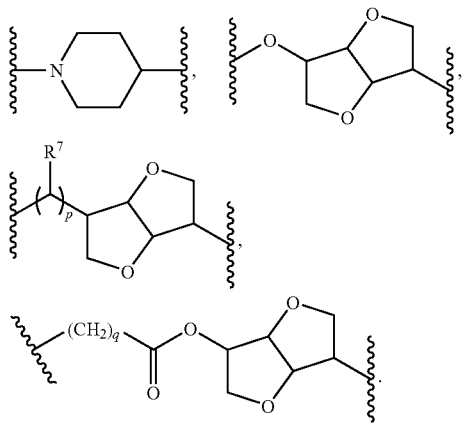

—NHCH₂(CH₂)ₙCH₂OC(O)—, wherein n is 0, 1, 2, or 3,
—CH₂NHC(O)CH₂NHC(O)—, —CH₂OC(O)—, —OCH(CH₃)OC(O)—, —OCH₂OC(O)—,
—CH₂CH₂C(O)NH—, —(CH₂)₅—, a bond, —C(CH₃)₂—, —CH(CH₃)—, —C(CH₃)(CH₂ONO₂)—, —(CH₂)₂—, —(CH₂)₃—,
—CH₂—, —CH₂CH₂NHC(O)—, —CH₂NHC(O)—, —CH(CH₂C₆H₅)NHC(O)—, —CH(CH₃)NHC(O)—,
—CH(CH(CH₃)₂NHC(O)—, —O—, —CH₂N(CH₃)C(O)—,

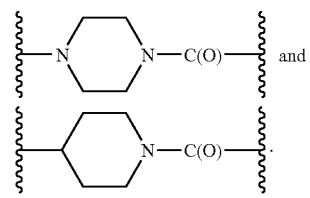

In another embodiment, R is selected from the group consisting of
—ONO₂, —O—CO—(CH₂)₃CH(ONO₂)CH₂(ONO₂),

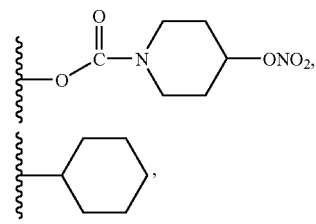

with the proviso that X is CR¹R³ and R³ is —CH₂ONO₂ or —ONO₂,
—(CH₂)₄ONO₂, —CH₂ONO₂, —(CH₂)₂ONO₂, —(CH₂)₃ONO₂, —(CH₂)₂CH(CH₃)ONO₂,
—CH₂—CH(ONO₂)—C(CH₃)₂—CH₂ONO₂,
—CH₂CH(ONO₂)CH(CH₃)ONO₂, —(CH₂)₂CH(ONO₂)CH₂ONO₂, —(CH₂)₃CH(ONO₂)CH₂(ONO₂),
—(CH₂)₄CH(ONO₂)CH₂(ONO₂),

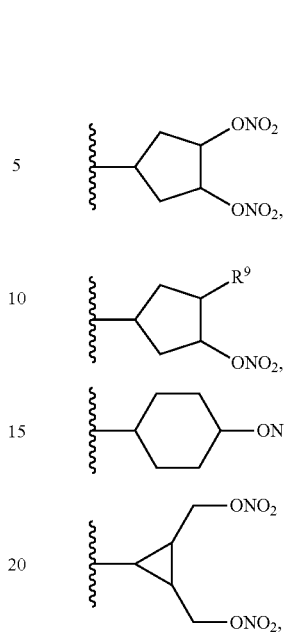

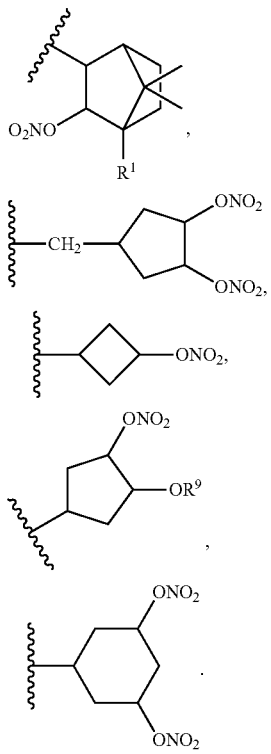

In another embodiment, —X—R is selected from the group consisting of

—(CH₂)₅ONO₂, —C(CH₃)₂CH₂ONO₂, —CH(CH₃)(CH₂)₂ONO₂, —C(CH₃)(CH₂ONO₂)CH₂ONO₂,
—C(CH₃)₂(CH₂)₃ONO₂, —(CH₂)₂CH(CH₃)ONO₂, —(CH₂)₂CH(ONO₂)CH(CH₃)ONO₂,
—CH₂NHC(O)(CH₂)₂CH(ONO₂)CH(ONO₂)CH₃, —CH₂NHC(O)(CH₂)₃CH(ONO₂)CH₂ONO₂,
—CH₂N(CH₃)C(O)(CH₂)₃CH(ONO₂)CH₂ONO₂, —O(CH₂)₄CH(ONO₂)CH₂ONO₂, —O(CH₂)₃ONO₂,

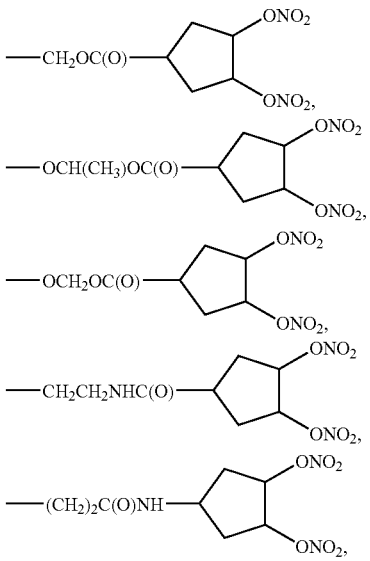

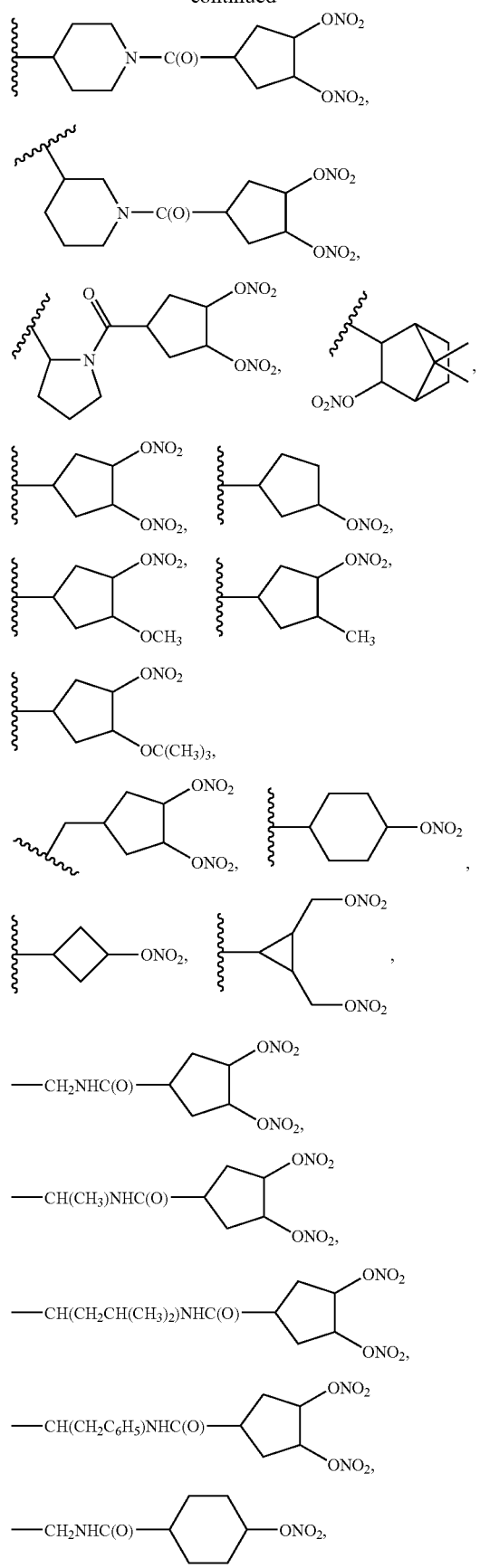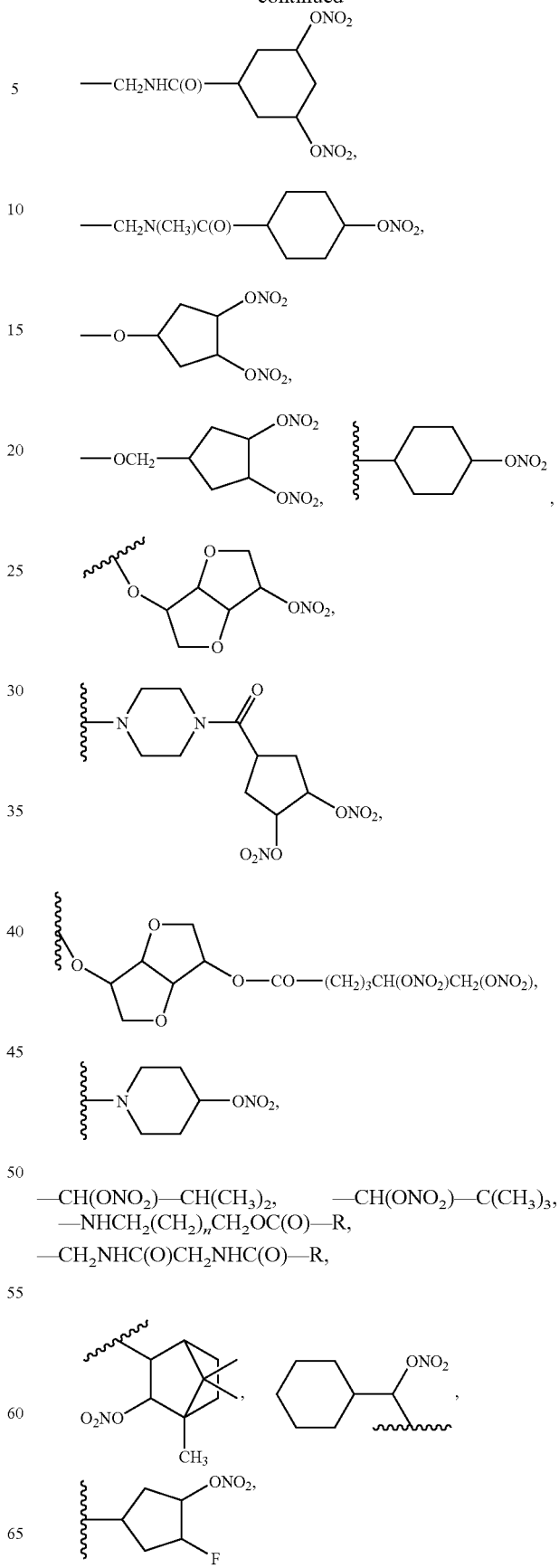

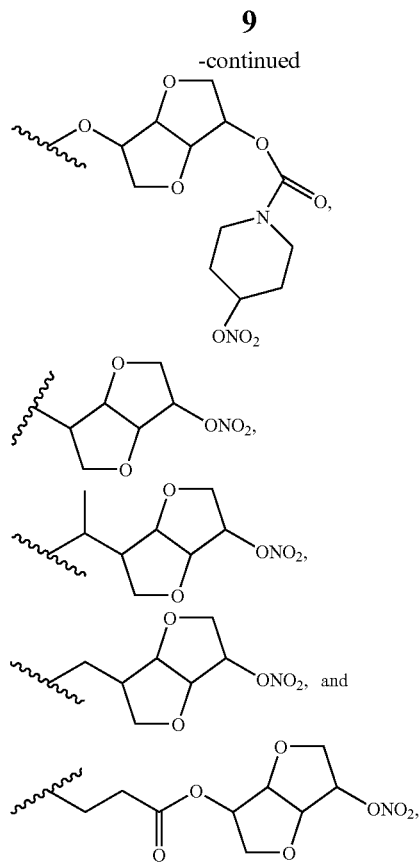
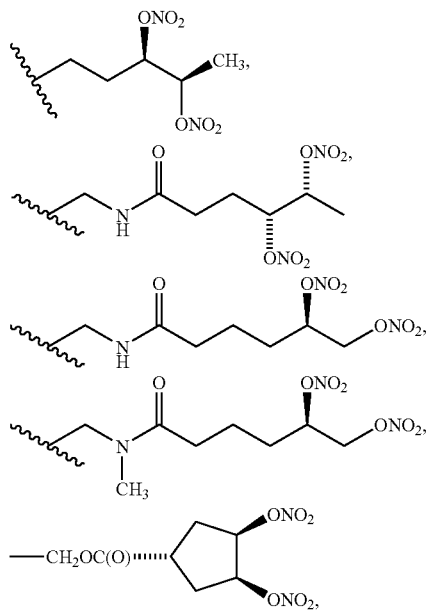
wherein n is 0, 1, 2 or 3.
In another embodiment, —X—R is selected from the group consisting of
—(CH$_2$)$_5$ONO$_2$, —C(CH$_3$)$_2$CH$_2$ONO$_2$, —CH(CH$_3$)(CH$_2$)$_2$ONO$_2$, —C(CH$_3$)(CH$_2$ONO$_2$)CH$_2$ONO$_2$,
—C(CH$_3$)$_2$(CH$_2$)$_3$ONO$_2$, —(CH$_2$)$_2$CH(CH$_3$)ONO$_2$, —O(CH$_2$)$_4$CH(ONO$_2$)CH$_2$ONO$_2$, —O(CH$_2$)$_3$ONO$_2$,
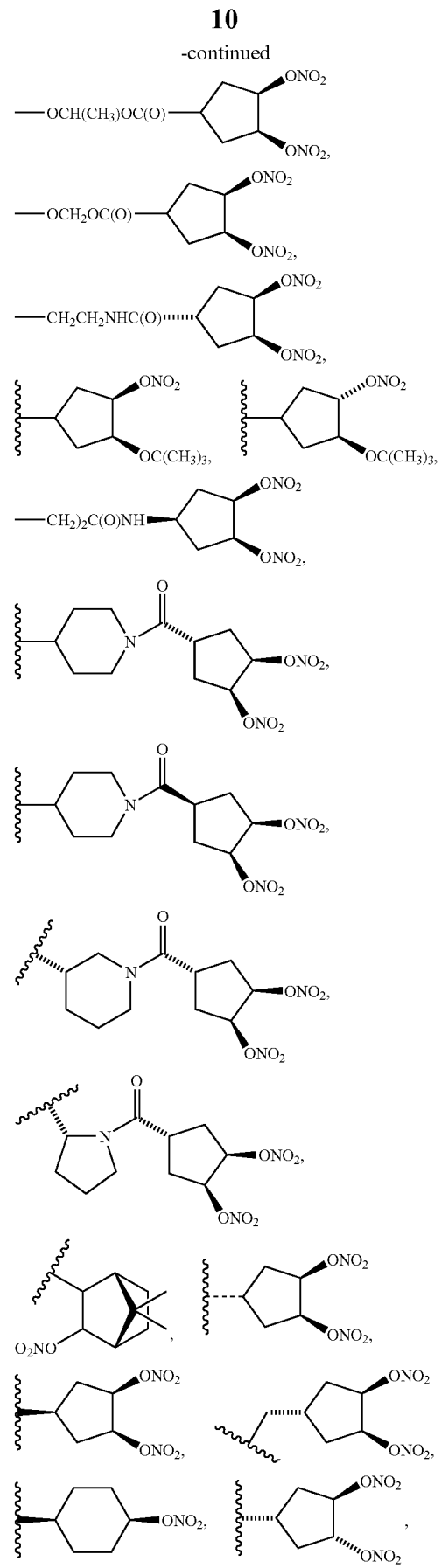

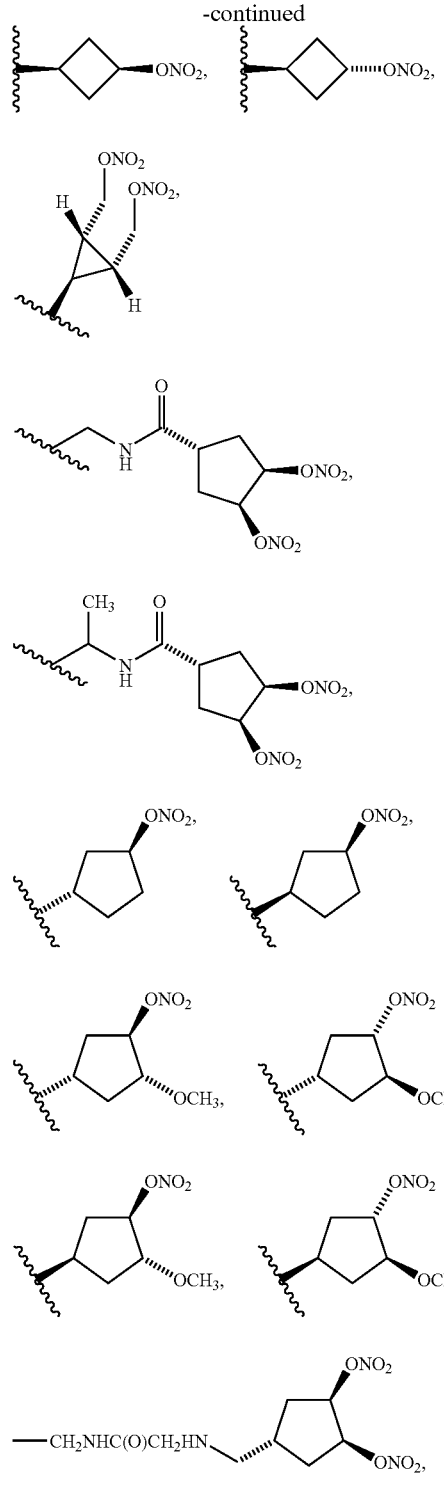
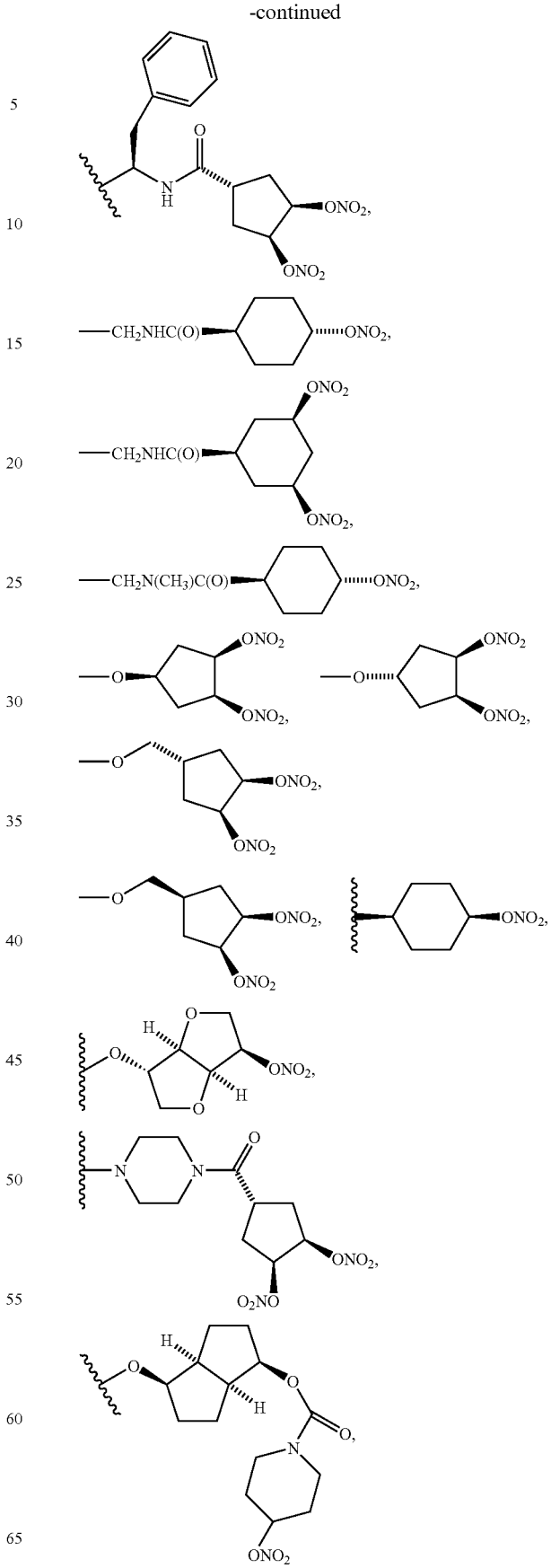

-continued

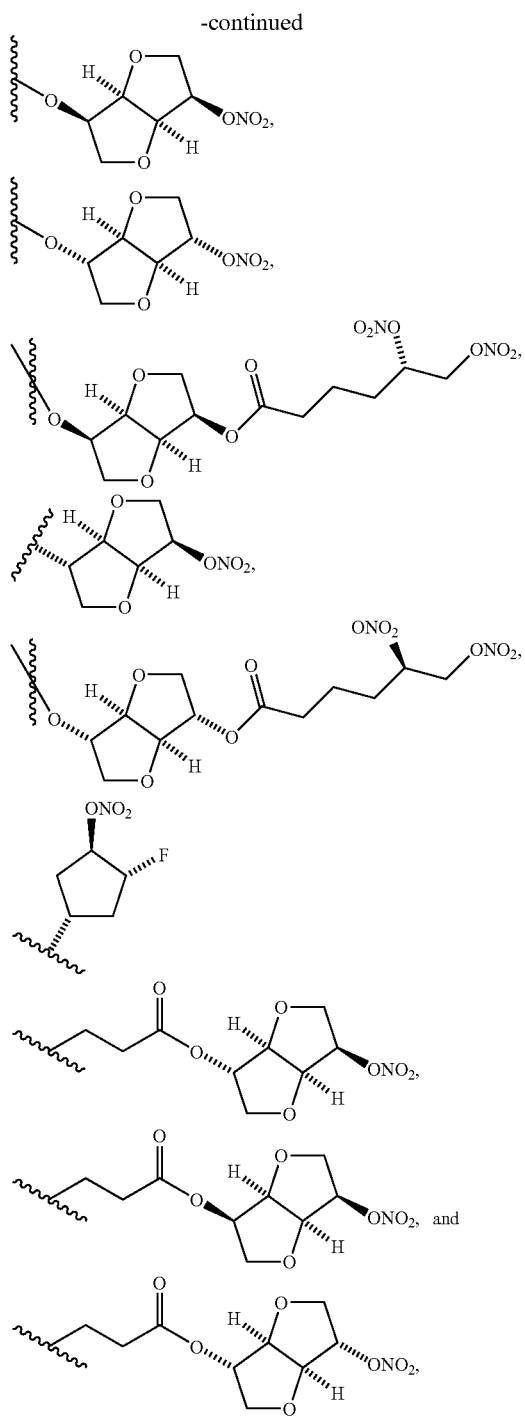

or a pharmaceutically acceptable salt thereof.

In another embodiment of the invention, the compound is selected from the group consisting of
(3S)-3-(4-Chlorophenyl)-6-methyl-1,3-dihydrofuro[3,4-c]pyridin-7-yl 4-{[(1r,3R,4S)-3,4-bis(nitrooxy)cyclopentyl]amino}-4-oxobutanoate,
3-(4-chlorophenyl)-6-methyl-1,3-dihydrofuro[3,4-c]pyridin-7-yl(1s,3R,4S)-3,4-bis(nitrooxy)cyclopentanecarboxylate,
3-(4-chlorophenyl)-6-methyl-1,3-dihydrofuro[3,4-c]pyridin-7-yl(1r,3R,4S)-3,4-bis(nitrooxy)cyclopentanecarboxylate,
(3S)-3-(4-chlorophenyl)-6-methyl-1,3-dihydrofuro[3,4-c]pyridin-7-yl(1s,3R,4S)-3,4-bis(nitrooxy)cyclopentanecarboxylate,
(3R)-3-(4-chlorophenyl)-6-methyl-1,3-dihydrofuro[3,4-c]pyridin-7-yl(1s,3R,4S)-3,4-bis(nitrooxy)cyclopentanecarboxylate,
(3S)-3-(4-chlorophenyl)-6-methyl-1,3-dihydrofuro[3,4-c]pyridin-7-yl(1s,3R,4S)-3,4-bis(nitrooxy)cyclopentanecarboxylate,
3-(4-chlorophenyl)-6-methyl-1,3-dihydrofuro[3,4-c]pyridin-7-yl 2,2-dimethyl-3-(nitrooxy)propanoate,
3-(4-chlorophenyl)-6-methyl-1,3-dihydrofuro[3,4-c]pyridin-7-yl 2-methyl-4-(nitrooxy)butanoate,
3-(4-chlorophenyl)-6-methyl-1,3-dihydrofuro[3,4-c]pyridin-7-yl 2-methyl-3-(nitrooxy)-2-[(nitrooxy)methyl]propanoate,
3-(4-chlorophenyl)-6-methyl-1,3-dihydrofuro[3,4-c]pyridin-7-yl 3-(nitrooxy)cyclopentanecarboxylate,
3-(4-chlorophenyl)-6-methyl-1,3-dihydrofuro[3,4-c]pyridin-7-yl 2,2-dimethyl-5-(nitrooxy)pentanoate,
3-(4-chlorophenyl)-6-methyl-1,3-dihydrofuro[3,4-c]pyridin-7-yl 4-(nitrooxy)pentanoate,
3-(4-chlorophenyl)-6-methyl-1,3-dihydrofuro[3,4-c]pyridin-7-yl[(1s,3R,4S)-3,4-bis(nitrooxy)cyclopentyl]acetate,
3-(4-chlorophenyl)-6-methyl-1,3-dihydrofuro[3,4-c]pyridin-7-yl cis-4-(nitrooxy)cyclohexanecarboxylate,
3-(4-chlorophenyl)-6-methyl-1,3-dihydrofuro[3,4-c]pyridin-7-yl 2,2-dimethyl-5-(nitrooxy)pentanoate,
3-(4-chlorophenyl)-6-methyl-1,3-dihydrofuro[3,4-c]pyridin-7-yl(3R,4R)-3,4-bis(nitrooxy)cyclopentanecarboxylate,
(3S)-3-(4-chlorophenyl)-6-methyl-1,3-dihydrofuro[3,4-c]pyridin-7-yl(4R,5R)-4,5-bis(nitrooxy)hexanoate,
3-(4-chlorophenyl)-6-methyl-1,3-dihydrofuro[3,4-c]pyridin-7-yl cis-3-(nitrooxy)cyclobutanecarboxylate,
3-(4-chlorophenyl)-6-methyl-1,3-dihydrofuro[3,4-c]pyridin-7-yl trans-3-(nitrooxy)cyclobutanecarboxylate,
(3S)-3-(4-chlorophenyl)-6-methyl-1,3-dihydrofuro[3,4-c]pyridin-7-yl(1r,2R,3S)-2,3-bis[(nitrooxy)methyl]cyclopropanecarboxylate,
(3S)-3-(4-chlorophenyl)-6-methyl-1,3-dihydrofuro[3,4-c]pyridin-7-yl N-{[(1s,3R,4S)-3,4-bis(nitrooxy)cyclopentyl]carbonyl}glycinate,
(3S)-3-(4-chlorophenyl)-6-methyl-1,3-dihydrofuro[3,4-c]pyridin-7-yl N-{[(1s,3R,4S)-3,4-bis(nitrooxy)cyclopentyl]carbonyl}-D-alaninate,
(3S)-3-(4-chlorophenyl)-6-methyl-1,3-dihydrofuro[3,4-c]pyridin-7-yl N-{[(1s,3R,4S)-3,4-bis(nitrooxy)cyclopentyl]carbonyl}-D-leucinate,
(3S)-3-(4-chlorophenyl)-6-methyl-1,3-dihydrofuro[3,4-c]pyridin-7-yl N-{[(1s,3R,4S)-3,4-bis(nitrooxy)cyclopentyl]carbonyl}-D-phenylalaninate,
(1r,3R,4S)-3,4-Bis(nitrooxy)cyclopentyl(3S)-3-(4-chlorophenyl)-6-methyl-1,3-dihydrofuro[3,4-c]pyridin-7-yl carbonate,
5,6-Bis(nitrooxy)hexyl 3-(4-chlorophenyl)-6-methyl-1,3-dihydrofuro[3,4-c]pyridin-7-yl carbonate,
3-(4-Chlorophenyl)-6-methyl-1,3-dihydrofuro[3,4-c]pyridin-7-yl 3-(nitrooxy)propyl carbonate,
(3S)-3-(4-Chlorophenyl)-6-methyl-1,3-dihydrofuro[3,4-c]pyridine-7-yl 4-{[(1s,3R,4S)-3,4-bis(nitrooxy)cyclopentyl]carbonyl}piperazine-1-carboxylate,
(S)—((S)-3-(4-chlorophenyl)-6-methyl-1,3-dihydrofuro[3,4-c]pyridin-7-yl)2-cyclohexyl-2-(nitrooxy)acetate,
(S)-3-(4-chlorophenyl)-6-methyl-1,3-dihydrofuro[3,4-c]pyridin-7-yl 2-(4,7,7-trimethyl-3-(nitrooxy)bicyclo[2.2.1]heptan-2-yl)acetate, (R)—((S)-3-(4-chlorophenyl)-6-methyl-1,3-dihydrofuro[3,4-c]pyridin-7-yl)3-methyl-2-(nitrooxy)butanoate,
(S)—((S)-3-(4-chlorophenyl)-6-methyl-1,3-dihydrofuro[3,4-c]pyridin-7-yl)3,3-dimethyl-2-(nitrooxy)butanoate,
(6R,6aS)-6-((3-(4-chlorophenyl)-6-methyl-1,3-dihydrofuro[3,4-c]pyridin-7-yloxy)carbonyloxy)hexahydrofuro[3,2-b]furan-3-yl 4-(nitrooxy)piperidine-1-carboxylate,
3-(4-chlorophenyl)-6-methyl-1,3-dihydrofuro[3,4-c]pyridin-7-yl 4-(nitrooxy)piperidine-1-carboxylate,
(S)-((3R,3aR,6R,6aR)-6-(((S)-3-(4-chlorophenyl)-6-methyl-1,3-dihydrofuro[3,4-c]pyridin-7-yloxy)carbonyloxy)hexahydrofuro[3,2-b]furan-3-yl)5,6-bis(nitrooxy)hexanoate,
(R)-((3S,3aR,6S,6aR)-6-(((S)-3-(4-chlorophenyl)-6-methyl-1,3-dihydrofuro[3,4-c]pyridin-7-yloxy)carbonyloxy)hexahydrofuro[3,2-b]furan-3-yl)5,6-bis(nitrooxy)hexanoate,
(S)-3-(4-chlorophenyl)-6-methyl-1,3-dihydrofuro[3,4-c]pyridin-7-yl(3R,3aR,6R,6aS)-6-(nitrooxy)hexahydrofuro[3,2-b]furan-3-yl carbonate,
(3S)-3-(4-chlorophenyl)-6-methyl-1,3-dihydrofuro[3,4-c]pyridine-7-yl(3S,3aR,6R,6aS)-6-(nitrooxy)hexahydrofuro[3,2-b]furan-3-yl carbonate,
(3S)-3-(4-chlorophenyl)-6-methyl-1,3-dihydrofuro[3,4-c]pyridin-7-yl(1R,3S,4S)-3-methoxy-4-(nitrooxy)cyclopentanecarboxylate,
(S)-3-(4-chlorophenyl)-6-methyl-1,3-dihydrofuro[3,4-c]pyridin-7-yl(3S,3aR,6S,6aS)-6-(nitrooxy)hexahydrofuro[3,2-b]furan-3-yl carbonate,
3-(4-Chlorophenyl)-6-methyl-1,3-dihydrofuro[3,4-c]pyridin-7-yl 4-(nitrooxy)butanoate,
(3S)-3-(4-Chlorophenyl)-6-methyl-1,3-dihydrofuro[3,4-c]pyridin-7-yl 4-(nitrooxy)butanoate,
(3R)-3-(4-Chlorophenyl)-6-methyl-1,3-dihydrofuro[3,4-c]pyridin-7-yl 4-(nitrooxy)butanoate,
1-[({[(3S)-3-(4-chlorophenyl)-6-methyl-1,3-dihydrofuro[3,4-c]pyridin-7-yl]oxy}carbonyl)oxy]ethyl (1s,3R,4S)-3,4-bis(nitrooxy)cyclopentanecarboxylate,
(3S)-3-(4-Chlorophenyl)-6-methyl-1,3-dihydrofuro[3,4-c]pyridin-7-yl-oxycarbonyloxymethyl(1s,3R,4S)-3,4-bis(nitrooxy)cyclopentanecarboxylate,
(3S)-3-(4-Chlorophenyl)-6-methyl-1,3-dihydrofuro[3,4-c]pyridin-7-yl-oxycarbonyl(1s,3R,4S)-3,4-bis(nitrooxy)cyclopentanecarboxylate,
[3-(4-chlorophenyl)-6-methyl-5-oxido-1,3-dihydrofuro[3,4-c]pyridin-5-ium-7-yl](3S,4R)-3,4-dinitrooxycyclopentanecarboxylate,
(3S)-3-(4-chlorophenyl)-6-methyl-1,3-dihydrofuro[3,4-c]pyridin-7-yl(1R,3R)-3-(nitrooxy)cyclopentanecarboxylate,
(3S)-3-(4-chlorophenyl)-6-methyl-1,3-dihydrofuro[3,4-c]pyridin-7-yl(1R,3R)-3-(nitrooxy)cyclopentanecarboxylate,
(3S)-3-(4-chlorophenyl)-6-methyl-1,3-dihydrofuro[3,4-c]pyridin-7-yl(1R,3S)-3-(nitrooxy)cyclopentanecarboxylate,
(3S)-3-(4-chlorophenyl)-6-methyl-1,3-dihydrofuro[3,4-c]pyridin-7-yl(1R,3S)-3-(nitrooxy)cyclopentanecarboxylate,
(3S)-3-(4-chlorophenyl)-6-methyl-1,3-dihydrofuro[3,4-c]pyridin-7-yl(1R,3R,4R)-3-methoxy-4-(nitrooxy)cyclopentanecarboxylate,
(3S)-3-(4-chlorophenyl)-6-methyl-1,3-dihydrofuro[3,4-c]pyridin-7-yl(1R,3R,4R)-3-methyoxy-4-(nitrooxy)cyclopentanecarboxylate,
(3S)-3-(4-chlorophenyl)-6-methyl-1,3-dihydrofuro[3,4-c]pyridin-7-yl(1R,3S,4S)-3-ethyoxy-4-(nitrooxy)cyclopentanecarboxylate,
(3S)-3-(4-chlorophenyl)-6-methyl-1,3-dihydrofuro[3,4-c]pyridin-7-yl(1R,3S,4S)-3-ethoxy-4-(nitrooxy)cyclopentanecarboxylate,
(3S)-3-(4-chlorophenyl)-6-methyl-1,3-dihydrofuro[3,4-c]pyridin-7-yl(1R,3S,4R)-3-methoxy-4-(nitrooxy)cyclopentanecarboxylate,
(3S)-3-(4-chlorophenyl)-6-methyl-1,3-dihydrofuro[3,4-c]pyridin-7-yl(1R,3S,4R)-3-methoxy-4-(nitrooxy)cyclopentanecarboxylate,
(3S)-3-(4-chlorophenyl)-6-methyl-1,3-dihydrofuro[3,4-c]pyridin-7-yl(1S,3R,4R)-3-tert-butoxy-4-(nitrooxy)cyclopentanecarboxylate,
(3S)-3-(4-chlorophenyl)-6-methyl-1,3-dihydrofuro[3,4-c]pyridin-7-yl(1S,3R,4R)-3-tert-butoxy-4-(nitrooxy)cyclopentanecarboxylate,
(3S)-3-(4-chlorophenyl)-6-methyl-1,3-dihydrofuro[3,4-c]pyridin-7-yl(1R,3R,4R)-3-fluoro-4-(nitrooxy)cyclopentanecarboxylate,
(3S)-3-(4-chlorophenyl)-6-methyl-1,3-dihydrofuro[3,4-c]pyridin-7-yl(1R,3R,4R)-3-fluoro-4-(nitrooxy)cyclopentanecarboxylate,
(3S)-3-(4-chlorophenyl)-6-methyl-1,3-dihydrofuro[3,4-c]pyridin-7-yl(1S,3S,4R)-3-methoxy-4-(nitrooxy)cyclopentanecarboxylate, and
(3S)-3-(4-chlorophenyl)-6-methyl-1,3-dihydrofuro[3,4-c]pyridin-7-yl(1S,3S,4R)-3-methoxy-4-(nitrooxy)cyclopentanecarboxylate,
(S)-3-(4-chlorophenyl)-6-methyl-1,3-dihydrofuro[3,4-c]pyridin-7-yl(R)-3,3-dimethyl-2,4-bis(nitrooxy)butyl carbonate,
(S)-3-(4-chlorophenyl)-6-methyl-1,3-dihydrofuro[3,4-c]pyridin-7-yl(3S,3aR,6R,6aS)-6-(nitrooxy)hexahydrofuro[3,2-b]furan-3-yl succinate,
(S)-3-(4-chlorophenyl)-6-methyl-1,3-dihydrofuro[3,4-c]pyridin-7-yl(3R,3aR,6R,6aS)-6-(nitrooxy)hexahydrofuro[3,2-b]furan-3-yl succinate,
(S)-3-(4-chlorophenyl)-6-methyl-1,3-dihydrofuro[3,4-c]pyridin-7-yl(3S,3aR,6S,6aS)-6-(nitrooxy)hexahydrofuro[3,2-b]furan-3-yl succinate,
2,3-bis(nitrooxy)propyl (S)-3-(4-chlorophenyl)-6-methyl-1,3-dihydrofuro[3,4-c]pyridin-7-yl succinate,
or a pharmaceutically acceptable salt thereof.

In another embodiment of the invention, the compound is (3S)-3-(4-chlorophenyl)-6-methyl-1,3-dihydrofuro[3,4-c]pyridin-7-yl(1R,3S,4S)-3-methoxy-4-(nitrooxy)cyclopentanecarboxylate.

In another embodiment of the invention, compounds have the general formula I:

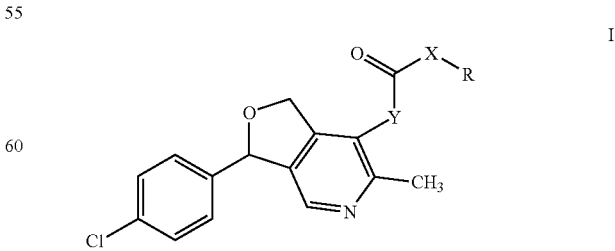

wherein
Y is —O— or a bond;

X is selected from the group consisting of:

a bond, —NHCH$_2$(CH$_2$)$_n$CH$_2$OC(O)—, —CH$_2$NHC(O)CH$_2$NHC(O)—,
—O—, —NR$^1$—, —CR$^1$R$^3$—, —(CH$_2$)$_p$—, —(CH$_2$)$_q$NR$^1$C(O)—, —CHR$^5$NR$^2$C(O)—, —(CH$_2$)$_q$C(O)—, —(CH$_2$)$_q$C(O)NR$^1$—,

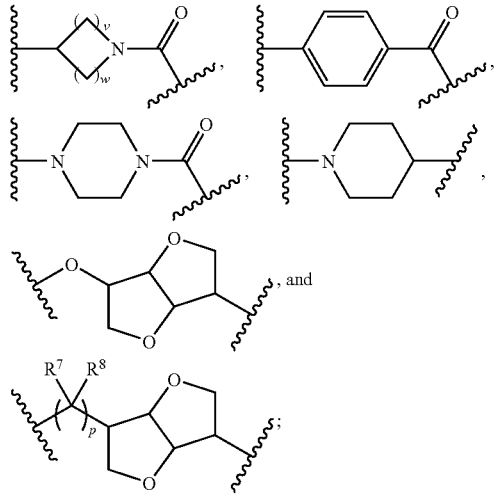

R$^1$, R$^2$, R$^4$, R$^7$ and R$^8$, each instance in which they occur, are independently selected from the group consisting of hydrogen and C$_{1-7}$ alkyl;

R$^3$ is hydrogen, C$_{1-4}$ alkyl or —CH$_2$ONO$_2$;

R$^5$ and R$^9$ are independently selected from the group consisting of hydrogen, —CH$_3$, —CH$_2$CH$_3$, —CH(CH$_3$)$_2$, —CH$_2$OH, —CH(OH)CH$_3$, and —CH$_2$C$_6$H$_5$;

p is 0, 1, 2, 3, 4, 5, 6, or 7;

q is 1, 2, 3, 4, or 5;

v and w are independently selected from the group consisting of 0, 1, 2, and 3, provided that v+w is 1, 2, 3 or 4;

R is selected from the group consisting of
—(CH$_2$)$_x$CH(ONO$_2$)(CH$_2$)$_y$CH$_3$,
—(CH$_2$)$_x$CH(ONO$_2$)(CH$_2$)$_y$CH(ONO$_2$)(CH$_2$)$_z$CH$_3$,
—(CH$_2$)$_x$CH(ONO$_2$)(CH$_2$)$_y$CH$_2$(ONO$_2$),
—CR$^1$R$^2$R$^3$,
—(CH$_2$)$_x$(ONO$_2$),
—O—C(O)—(CH$_2$)$_x$CH(ONO$_2$)(CH$_2$)$_y$CH$_2$(ONO$_2$),

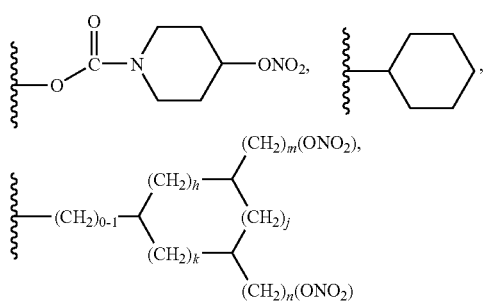

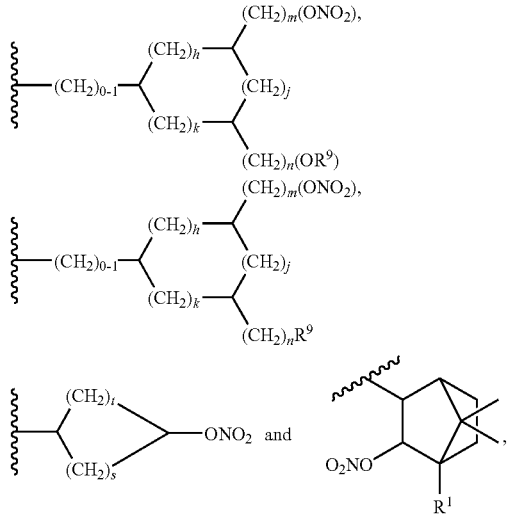

provided that when R is
—O—C(O)—(CH$_2$)$_x$CH(ONO$_2$)(CH$_2$)$_y$CH$_2$(ONO$_2$) or

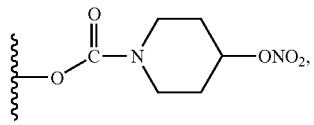

then X is selected from the group consisting of a bond,
—NR$^1$—, —CR$^1$R$^3$—, —(CH$_2$)$_p$—, —(CH$_2$)$_q$NR$^1$C(O)—,
—CHR$^5$NR$^2$C(O)—, —(CH$_2$)$_q$C(O)—, —(CH$_2$)$_q$C(O)NR$^1$—,

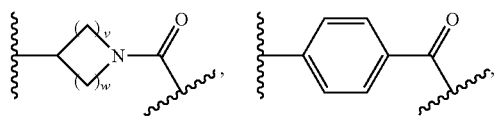

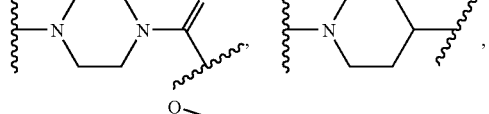

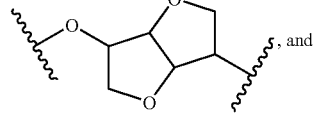

h, j, and k are independently selected from the group consisting of 0, 1, and 2;

m, n, x, y, and z are independently selected from the group consisting of 0, 1, 2, 3, and 4;

r and s are independently selected from the group consisting of 0, 1, 2, and 3, provided that r+s is 1, 2, 3 or 4.

In another embodiment of the invention, formula I is selected from the group consisting of

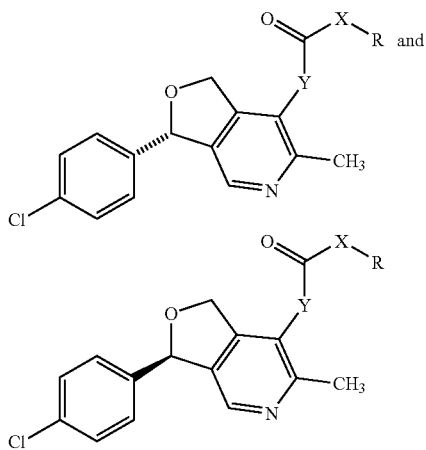 and

In another embodiment of the invention, Y is —O—.
In another embodiment of the invention, Y is a bond and X is

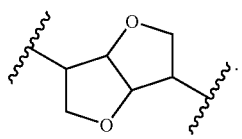

In another embodiment of the invention, X is selected from the group consisting of

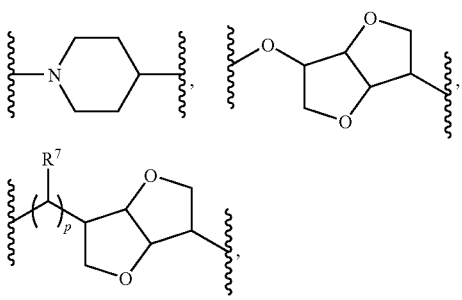

—NHCH₂(CH₂)ₙCH₂OC(O)—, wherein n is 0, 1, 2, or 3,
—CH₂NHC(O)CH₂NHC(O)—,
—CH₂CH₂C(O)NH—, —(CH₂)₅—, a bond, —C(CH₃)₂—,
—CH(CH₃)—, —C(CH₃)(CH₂ONO₂)—, —(CH₂)₂—,
—(CH₂)₃—,
—CH₂—, —CH₂NHC(O)—, —CH(CH₂C₆H₅)NHC(O)—,
—CH(CH₃)NHC(O)—, —CH(CH(CH₃))NHC(O)—,
—O—,
—CH₂N(CH₃)C(O)—,

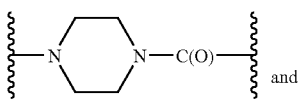 and

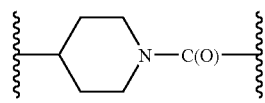

In another embodiment, R is selected from the group consisting of

—ONO₂, —O—CO—(CH₂)₃CH(ONO₂)CH₂(ONO₂),

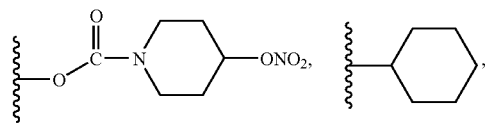

—(CH₂)₄ONO₂, —CH₂ONO₂, —(CH₂)₂ONO₂, —(CH₂)₃ONO₂, —(CH₂)₂CH(CH₃)ONO₂,
—CH₂CH(ONO₂)CH(CH₃)ONO₂, —(CH₂)₂CH(ONO₂)CH₂ONO₂, —(CH₂)₃CH(ONO₂)CH₂(ONO₂),
—(CH₂)₄CH(ONO₂)CH₂(ONO₂),

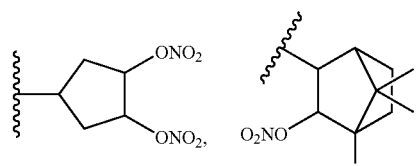

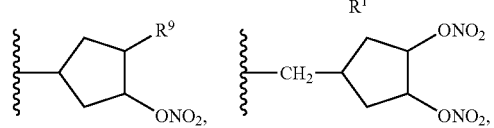

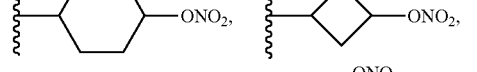

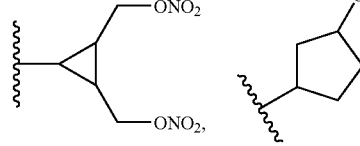 and

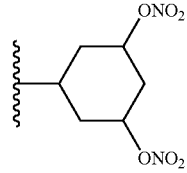

In another embodiment, —X—R is selected from the group consisting of
—(CH₂)₅ONO₂, —C(CH₃)₂CH₂ONO₂, —CH(CH₃)(CH₂)₂ONO₂, —C(CH₃)(CH₂ONO₂)CH₂ONO₂,
—C(CH₃)₂(CH₂)₃ONO₂, —(CH₂)₂CH(CH₃)ONO₂,
—(CH₂)₂CH(ONO₂)CH(CH₃)ONO₂,
—CH₂NHC(O)(CH₂)₂CH(ONO₂)CH(ONO₂)CH₃,
CH₂NHC(O)(CH₂)₃CH(ONO₂)CH₂ONO₂,
—CH₂N(CH₃)C(O)(CH₂)₃CH(ONO₂)CH₂ONO₂,
—O(CH₂)₄CH(ONO₂)CH₂ONO₂, —O(CH₂)₃ONO₂,

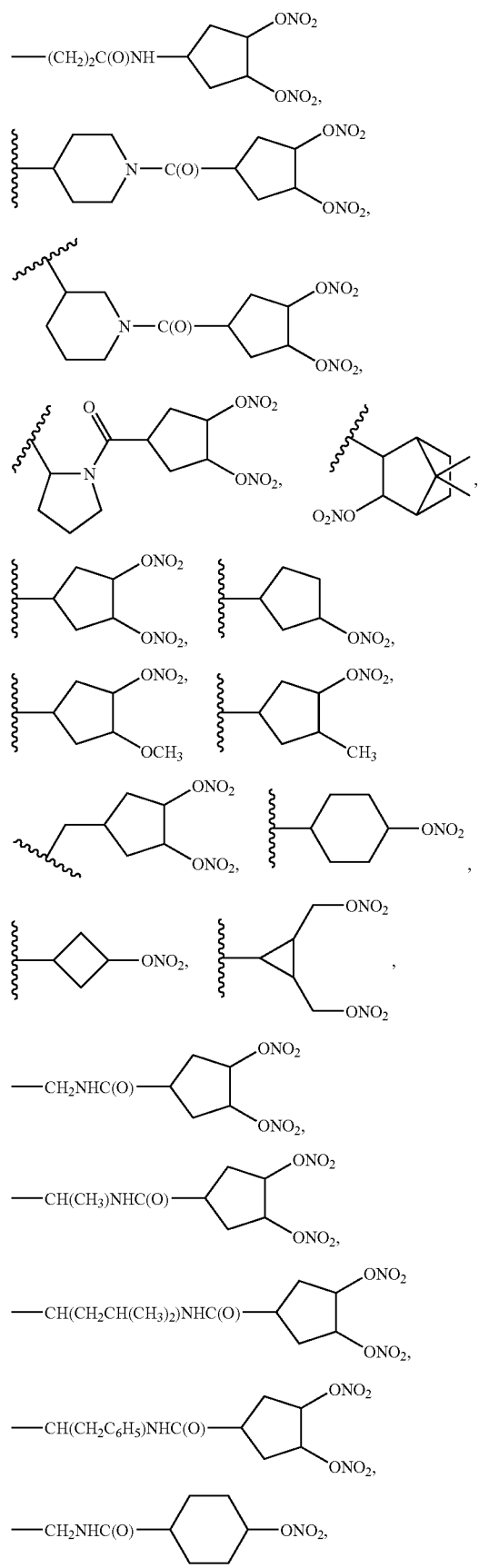
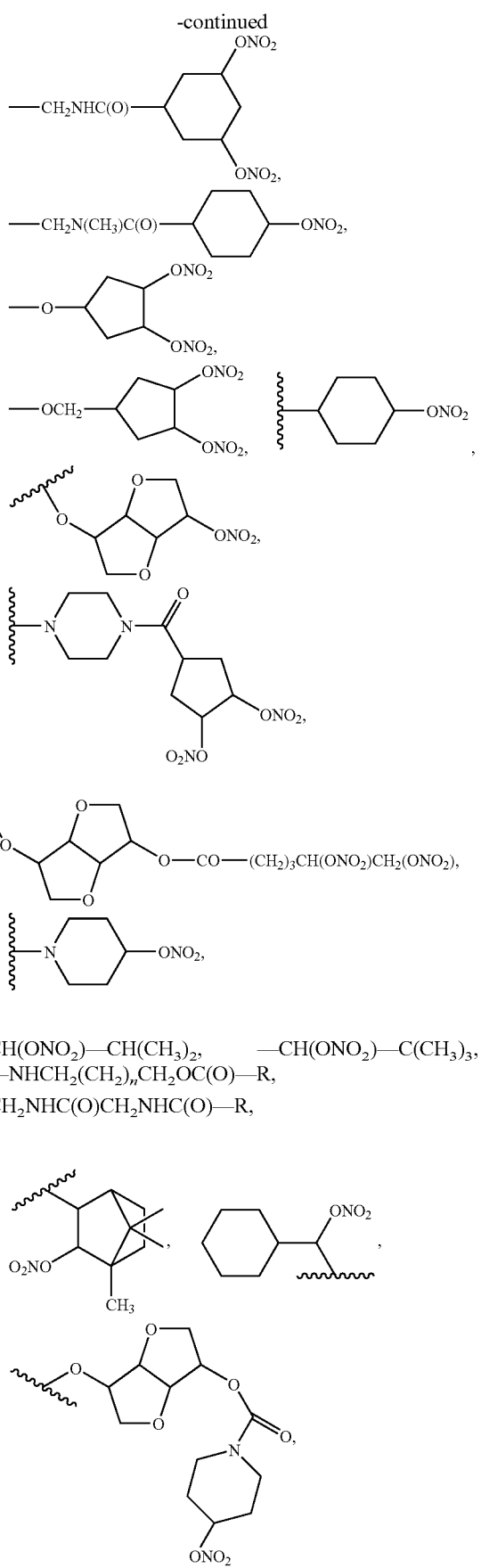

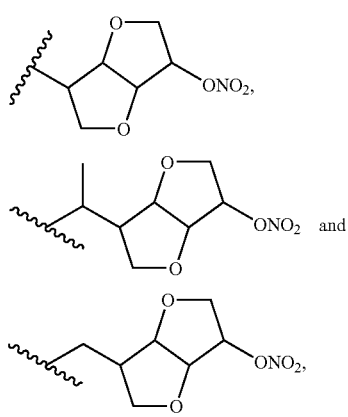
wherein n is 0, 1, 2 or 3.
In another embodiment, —X—R is selected from the group consisting of
—(CH$_2$)$_5$ONO$_2$, —C(CH$_3$)$_2$CH$_2$ONO$_2$, —CH(CH$_3$)(CH$_2$)$_2$ONO$_2$, —C(CH$_3$)(CH$_2$ONO$_2$)CH$_2$ONO$_2$, —C(CH$_3$)$_2$(CH$_2$)$_3$ONO$_2$, —(CH$_2$)$_2$CH(CH$_3$)ONO$_2$, —O(CH$_2$)$_4$CH(ONO$_2$)CH$_2$ONO$_2$, —O(CH$_2$)$_3$ONO$_2$,
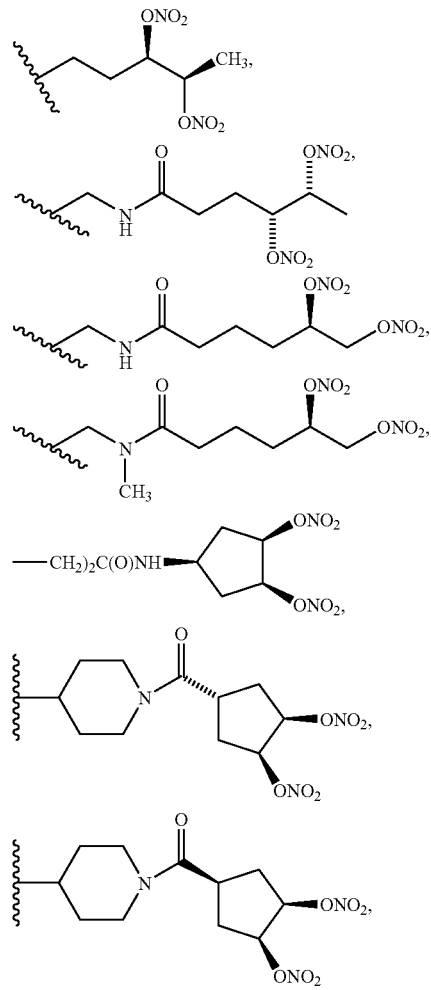
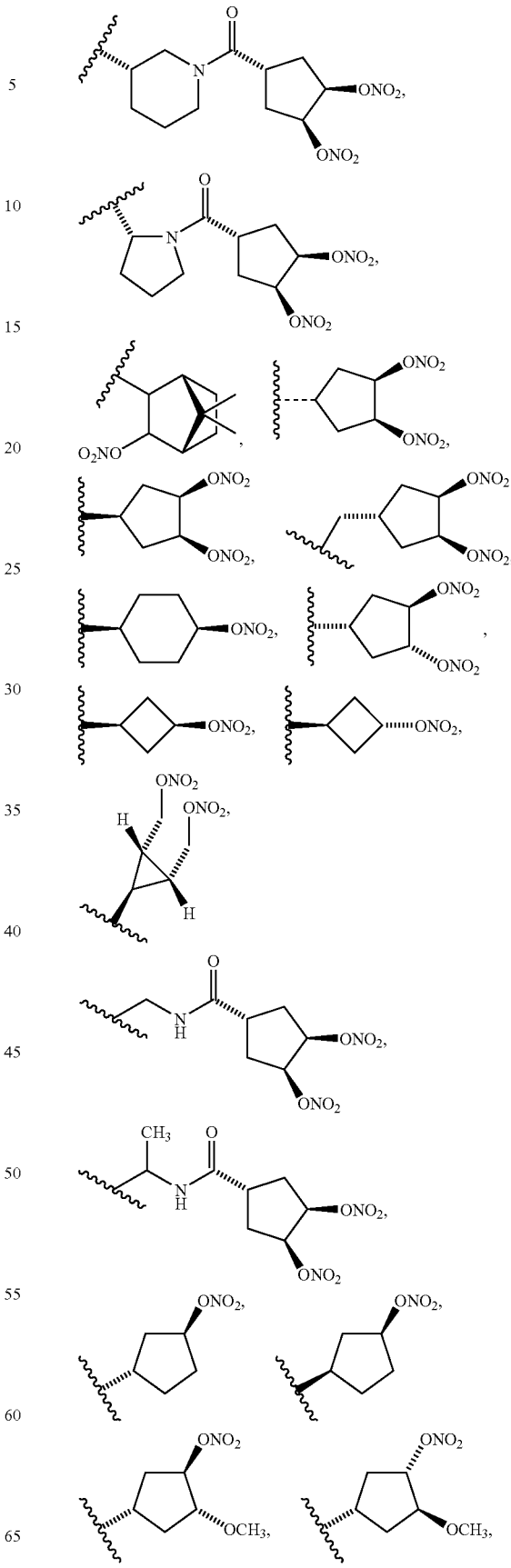

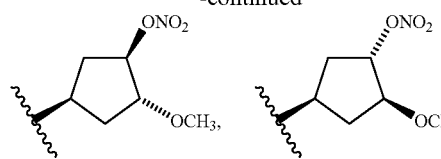
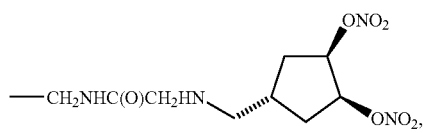
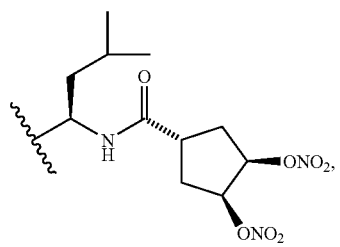
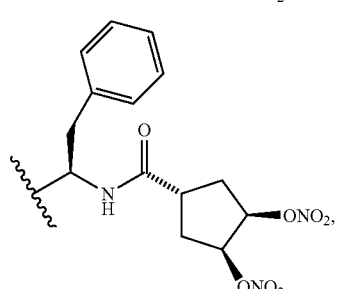
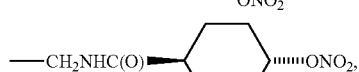
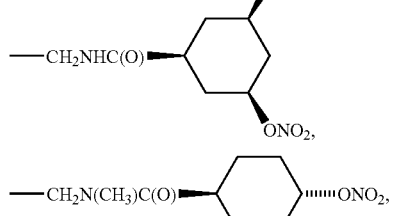
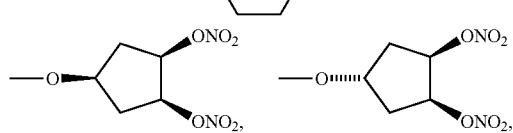
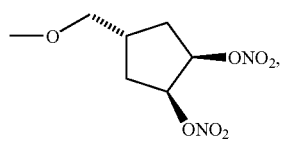
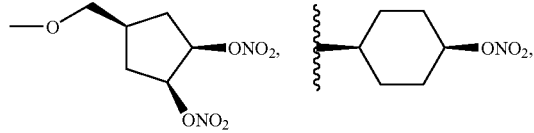
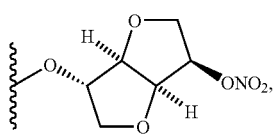

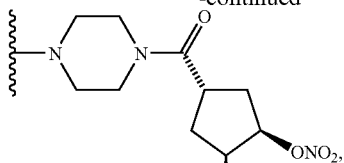
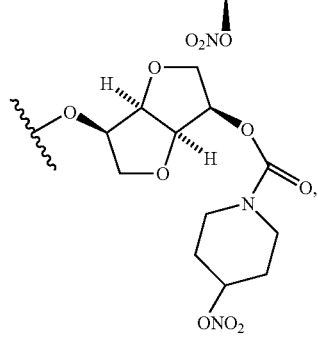
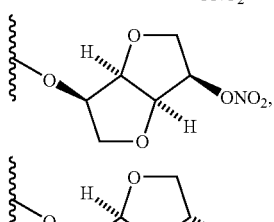
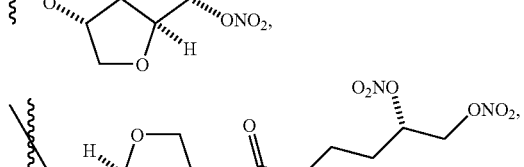
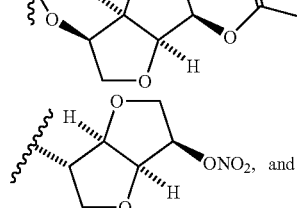
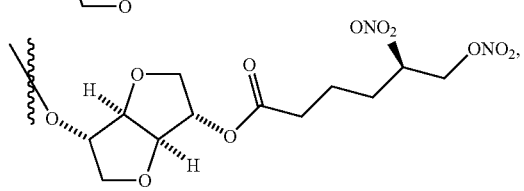

or a pharmaceutically acceptable salt thereof.

In another embodiment of the invention, the compound is selected from the group consisting of (3S)-3-(4-Chlorophenyl)-6-methyl-1,3-dihydrofuro[3,4-c]pyridin-7-yl 4-{[(1r,3R,4S)-3,4-bis(nitrooxy)cyclopentyl]amino}-4-oxobutanoate, 3-(4-chlorophenyl)-6-methyl-1,3-dihydrofuro[3,4-c]pyridin-7-yl(1s,3R,4S)-3,4-bis(nitrooxy)cyclopentanecarboxylate, 3-(4-chlorophenyl)-6-methyl-1,3-dihydrofuro[3,4-c]pyridin-7-yl(1r,3R,4S)-3,4-bis(nitrooxy)cyclopentanecarboxylate, (3S)-3-(4-chlorophenyl)-6-methyl-1,3-dihydrofuro[3,4-c]pyridin-7-yl(1s,3R,4S)-3,4-bis(nitrooxy)cyclopentanecarboxylate, (3R)-3-(4-chlorophenyl)-6-methyl-1,3-dihydrofuro[3,4-c]pyridin-7-yl(1s,3R,4S)-3,4-bis(nitrooxy)cyclopentanecarboxylate, (3S)-3-(4-chlorophenyl)-6-methyl-1,3-dihydrofuro[3,4-c]
  pyridin-7-yl(1s,3R,4S)-3,4-bis(nitrooxy)cyclopentan-
  ecarboxylate,
3-(4-chlorophenyl)-6-methyl-1,3-dihydrofuro[3,4-c]pyri-
  din-7-yl 2,2-dimethyl-3-(nitrooxy)propanoate,
3-(4-chlorophenyl)-6-methyl-1,3-dihydrofuro[3,4-c]pyri-
  din-7-yl 2-methyl-4-(nitrooxy)butanoate,
3-(4-chlorophenyl)-6-methyl-1,3-dihydrofuro[3,4-c]pyri-
  din-7-yl 2-methyl-3-(nitrooxy)-2-[(nitrooxy)methyl]pro-
  panoate,
3-(4-chlorophenyl)-6-methyl-1,3-dihydrofuro[3,4-c]pyri-
  din-7-yl 3-(nitrooxy)cyclopentanecarboxylate,
3-(4-chlorophenyl)-6-methyl-1,3-dihydrofuro[3,4-c]pyri-
  din-7-yl 2,2-dimethyl-5-(nitrooxy)pentanoate,
3-(4-chlorophenyl)-6-methyl-1,3-dihydrofuro[3,4-c]pyri-
  din-7-yl 4-(nitrooxy)pentanoate,
3-(4-chlorophenyl)-6-methyl-1,3-dihydrofuro[3,4-c]pyri-
  din-7-yl[(1s,3R,4S)-3,4-bis(nitrooxy)cyclopentyl]acetate,
3-(4-chlorophenyl)-6-methyl-1,3-dihydrofuro[3,4-c]pyri-
  din-7-yl cis-4-(nitrooxy)cyclohexanecarboxylate,
3-(4-chlorophenyl)-6-methyl-1,3-dihydrofuro[3,4-c]pyri-
  din-7-yl 2,2-dimethyl-5-(nitrooxy)pentanoate,
3-(4-chlorophenyl)-6-methyl-1,3-dihydrofuro[3,4-c]pyri-
  din-7-yl(3R,4R)-3,4-bis(nitrooxy)cyclopentanecarboxy-
  late,
(3S)-3-(4-chlorophenyl)-6-methyl-1,3-dihydrofuro[3,4-c]
  pyridin-7-yl(4R,5R)-4,5-bis(nitrooxy)hexanoate,
3-(4-chlorophenyl)-6-methyl-1,3-dihydrofuro[3,4-c]pyri-
  din-7-yl cis-3-(nitrooxy)cyclobutanecarboxylate,
3-(4-chlorophenyl)-6-methyl-1,3-dihydrofuro[3,4-c]pyri-
  din-7-yl trans-3-(nitrooxy)cyclobutanecarboxylate,
(3S)-3-(4-chlorophenyl)-6-methyl-1,3-dihydrofuro[3,4-c]
  pyridin-7-yl(1r,2R,3S)-2,3-bis[(nitrooxy)methyl]cyclo-
  propanecarboxylate,
(3S)-3-(4-chlorophenyl)-6-methyl-1,3-dihydrofuro[3,4-c]
  pyridin-7-yl N-{[(1s,3R,4S)-3,4-bis(nitrooxy)cyclopen-
  tyl]carbonyl}glycinate,
(3S)-3-(4-chlorophenyl)-6-methyl-1,3-dihydrofuro[3,4-c]
  pyridin-7-yl N-{[(1s,3R,4S)-3,4-bis(nitrooxy)cyclopen-
  tyl]carbonyl}-D-alaninate,
(3S)-3-(4-chlorophenyl)-6-methyl-1,3-dihydrofuro[3,4-c]
  pyridin-7-yl N-{[(1s,3R,4S)-3,4-bis(nitrooxy)cyclopen-
  tyl]carbonyl}-D-leucinate,
(3S)-3-(4-chlorophenyl)-6-methyl-1,3-dihydrofuro[3,4-c]
  pyridin-7-yl N-{[(1s,3R,4S)-3,4-bis(nitrooxy)cyclopen-
  tyl]carbonyl}-D-phenylalaninate,
(1r,3R,4S)-3,4-Bis(nitrooxy)cyclopentyl (3S)-3-(4-chlo-
  rophenyl)-6-methyl-1,3-dihydrofuro[3,4-c]pyridin-7-yl
  carbonate,
5,6-Bis(nitrooxy)hexyl 3-(4-chlorophenyl)-6-methyl-1,3-di-
  hydrofuro[3,4-c]pyridin-7-yl carbonate,
3-(4-Chlorophenyl)-6-methyl-1,3-dihydrofuro[3,4-c]pyri-
  din-7-yl 3-(nitrooxy)propyl carbonate,
(3S)-3-(4-Chlorophenyl)-6-methyl-1,3-dihydrofuro[3,4-c]
  pyridine-7-yl 4-{[(1s,3R,4S)-3,4-bis(nitrooxy)cyclopen-
  tyl]carbonyl}piperazine-1-carboxylate,
(S)—((S)-3-(4-chlorophenyl)-6-methyl-1,3-dihydrofuro
  [3,4-c]pyridin-7-yl)2-cyclohexyl-2-(nitrooxy)acetate,
(S)-3-(4-chlorophenyl)-6-methyl-1,3-dihydrofuro[3,4-c]py-
  ridin-7-yl 2-(4,7,7-trimethyl-3-(nitrooxy)bicyclo[2.2.1]
  heptan-2-yl)acetate,
(R)—((S)-3-(4-chlorophenyl)-6-methyl-1,3-dihydrofuro[3,
  4-c]pyridin-7-yl)3-methyl-2-(nitrooxy)butanoate,
(S)—((S)-3-(4-chlorophenyl)-6-methyl-1,3-dihydrofuro[3,
  4-c]pyridin-7-yl)3,3-dimethyl-2-(nitrooxy)butanoate,
(6R,6aS)-6-((3-(4-chlorophenyl)-6-methyl-1,3-dihydrofuro
  [3,4-c]pyridin-7-yloxy)carbonyloxy)hexahydrofuro[3,2-
  b]furan-3-yl 4-(nitrooxy)piperidine-1-carboxylate,
3-(4-chlorophenyl)-6-methyl-1,3-dihydrofuro[3,4-c]pyri-
  din-7-yl 4-(nitrooxy)piperidine-1-carboxylate,
(S)-((3R,3aR,6R,6aR)-6-(((S)-3-(4-chlorophenyl)-6-me-
  thyl-1,3-dihydrofuro[3,4-c]pyridin-7-yloxy)carbonyloxy)
  hexahydrofuro[3,2-b]furan-3-yl)5,6-bis(nitrooxy)hex-
  anoate,
(R)-((3S,3aR,6S,6aR)-6-(((S)-3-(4-chlorophenyl)-6-methyl-
  1,3-dihydrofuro[3,4-c]pyridin-7-yloxy)carbonyloxy)
  hexahydrofuro[3,2-b]furan-3-yl)5,6-bis(nitrooxy)hex-
  anoate,
(S)-3-(4-chlorophenyl)-6-methyl-1,3-dihydrofuro[3,4-c]py-
  ridin-7-yl(3R,3aR,6R,6aS)-6-(nitrooxy)hexahydrofuro[3,
  2-b]furan-3-yl carbonate,
(3S)-3-(4-chlorophenyl)-6-methyl-1,3-dihydrofuro[3,4-c]
  pyridine-7-yl(3S,3aR,6R,6aS)-6-(nitrooxy)hexahydro-
  furo[3,2-b]furan-3-yl carbonate,
(3S)-3-(4-chlorophenyl)-6-methyl-1,3-dihydrofuro[3,4-c]
  pyridin-7-yl(1R,3S,4S)-3-methoxy-4-(nitrooxy)cyclo-
  pentanecarboxylate
and
(S)-3-(4-chlorophenyl)-6-methyl-1,3-dihydrofuro[3,4-c]py-
  ridin-7-yl(3S,3aR,6S,6aS)-6-(nitrooxy)hexahydrofuro[3,
  2-b]furan-3-yl carbonate.

In another embodiment of the invention, the compound is (3S)-3-(4-chlorophenyl)-6-methyl-1,3-dihydrofuro[3,4-c] pyridin-7-yl(1R,3S,4S)-3-methoxy-4-(nitrooxy)cyclopentanecarboxylate.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof are represented. As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g. "$\text{\textcent}$—", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

Variable definitions which include representations such as the structure below,

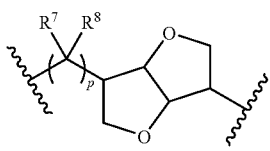

where p is 0, 1, 2, 3, 4, 5, 6, or 7, and where $R^7$ and $R^8$ are, for example, selected from the group consisting of hydrogen, —$CH_3$, and $CH_2CH_3$, are representative of moieties having the represented number of carbon atoms, to which are attached in each instance similar or different groups independently selected from the definitions of $R^7$ and $R^8$. Accordingly, the above structure and definitions of p, $R^7$ and $R^8$ include, for example, the following moieties:

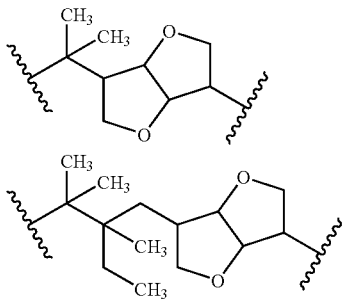

where $R^7$ and $R^8$ have different meanings on each carbon atom.

The diuretics of the invention are useful for treating hypertension. Pulmonary Arterial Hypertension, congestive heart failure, conditions resulting from excessive water retention, cardiovascular diseases, diabetes, oxidative stress, endothelial dysfunction, cirrhosis, pre-eclampsia, osteoporosis, or nephropathy, comprising administering a compounds of the invention to a patient having such a condition, or being at risk to having such condition The invention also relates to the use of diuretics of the invention for the preparation of a medicament for the treatment and/or prophylaxis of the above-mentioned diseases.

The above-mentioned diuretics of the invention are also of use in combination with other pharmacologically active compounds comprising angiotensin II receptor antagonists (e.g., losartan, valsartan, candesartan, irbesartan, olmesartan) angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104.869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S,5S,7S)-N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, verapamil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartatc), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

The dosage regimen utilizing the diuretics is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the diuretics, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the diuretics may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The diuretics of the invention can be administered in such oral forms as tablets, capsules and granules. The diuretics are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose acetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

Methods of Synthesis

Several methods for preparing the compounds of this invention are described in the following Schemes and Examples. Starting materials and intermediates are made from known procedures or as otherwise illustrated.

Scheme 1 describes a convenient method to prepare 3-(4-chlorophenyl)-6-methyl-1,3-dihydrofuro[3,4-c]pyridin-7-yl carboxylate ester compounds of the general structure 1-3 in this invention. Either racemic or enantiomeric phenol 1-1 is treated with an activated acid 1-2 at an appropriate temperature such as room temperature in the presence of a suitable base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone. Acid chloride 1-2 can be readily formed by treating an appropriate carboxylic acid with an chlorinating reagent such as thionyl chloride, phosphorus trichloride, phosphorus pentachloride, oxalyl chloride in the presence of catalyticat amount of Vilsmeier reagent, or triphenylphosphine and carbon tetrachloride or trichloroacetonitrile. Other forms of activated acid 1-2 can be prepared using methods known to those skilled in the art.

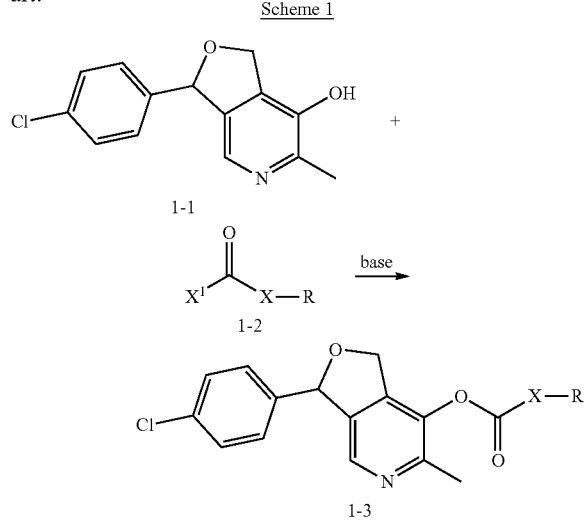

Scheme 1

$X^1$ = Cl, Br, F, OC$_6$F$_5$, N-hydroxysuccinimide
—X—R is as defined above

Scheme 2 delineates an alternative method to prepared 3-(4-chlorophenyl)-6-methyl-1,3-dihydrofuro[3,4-c]pyridin-7-yl carboxylate ester compounds of the general structure 1-3 in this invention. The carboxylic acid in this reaction can be activated for acylation at an appropriate temperature such as room temperature with a suitable coupling reagent such (benzotriazol-1-yl-oxy)tripyrrolidinophosphonium hexafluorophosphate (PyBOP), bis(2-oxo-3-oxazolidinyl) phosphinic chloride (BOP-Cl), or 1,1'-carbonyldiimidazole in the presence or absence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone.

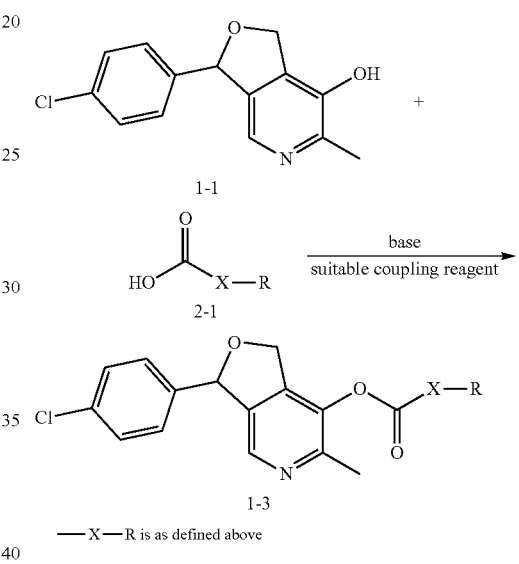

Scheme 2

—X—R is as defined above

Scheme 3 describes a straightforward method to prepare 3-(4-chlorophenyl)-6-methyl-1,3-dihydrofuro[3,4-c]pyridin-7-yl carbonate compounds of the general structure 3-2 in this invention. Either racemic or enantiomeric phenol 1-1 is treated with an activated formate 3-1 at an appropriate temperature such as room temperature in the presence of a suitable base such as N,N-diisopropylethylamine, triethylamine, N-methylmorpholine, pyridine, lutidine, potassium carbonate, sodium carbonate, cesium carbonate, or sodium hydride in an appropriate solvent such as dichloromethane, dichloroethane, chloroform, acetonitrile, tetrahydrofuran, dioxane, toluene, N,N-dimethylformamide, or N-methylpyrrolidinone. The activated formate 3-1 can be prepared by treating an appropriate alcohol at an appropriate temperature such as 0° C. or room temperature with a suitable reagent such as phosgene, trichloromethyl chloroformate, 1,1'-carbonyldiimidazole, p-nitrophenyl chloroformate, trichloroacetyl chloride, or 1-chloroethyl chloroformate in the presence of a suitable base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone.

Scheme 3

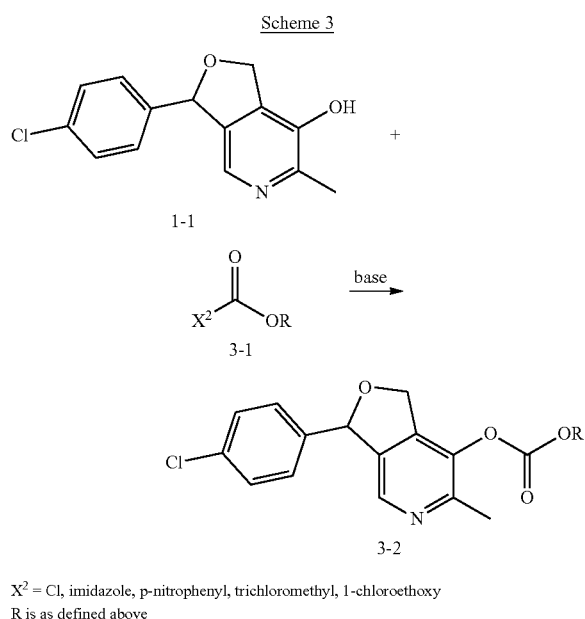

$X^2$ = Cl, imidazole, p-nitrophenyl, trichloromethyl, 1-chloroethoxy
R is as defined above Scheme 4 describes an alternative method to prepare 3-(4-chlorophenyl)-6-methyl-1,3-dihydrofuro[3,4-c]pyridin-7-yl carbonate compounds of the general structure 3-2 in this invention. In this reaction, an activated formate 4-1 of either racemic or enantiomeric 3-(4-chlorophenyl)-6-methyl-1,3-dihydrofuro[3,4-c]pyridin-7-ol is treated with an appropriate alcohol 4-2 at an appropriate temperature such as room temperature in the presence of a suitable base such as N,N-diisopropylethylamine, triethylamine, N-methylmorpholine, pyridine, lutidine, potassium carbonate, sodium carbonate, cesium carbonate, or sodium hydride in an appropriate solvent such as dichloromethane, dichloroethane, chloroform, acetonitrile, tetrahydrofuran, dioxane, toluene, N,N-dimethylformamide, or N-methylpyrrolidinone. The activated fromate 4-1 can be prepared by treating the phenol 1-1 at an appropriate temperature such as 0° C. or room temperature with a suitable reagent such as phosgene, trichloromethyl chloroformate, 1,1'-carbonyldiimidazole, p-nitrophenyl chloroformate, trichloroacetyl chloride, or 1-chloroethyl chloroformate in the presence of a suitable base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone.

Scheme 4

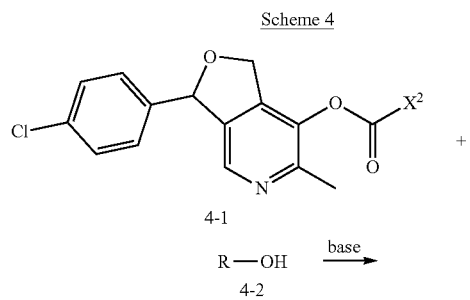

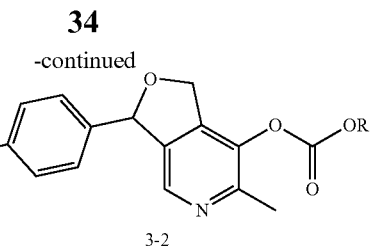

$X^2$ = Cl, imidazole, p-nitrophenyl, trichloromethyl, 1-chloroethoxy
R is as defined above Finally, Scheme 5 describes a convenient method to prepare 3-(4-chlorophenyl)-6-methyl-1,3-dihydrofuro[3,4-c]pyridin-7-yl carbamate compounds of the general structure 5-2 in this invention. Either racemic or enantiomeric phenol 1-1 is treated with an activated formamide 5-1 at an appropriate temperature such as room temperature in the presence of a suitable base such as N,N-diisopropylethylamine, triethylamine, N-methylmorpholine, pyridine, lutidine, potassium carbonate, sodium carbonate, cesium carbonate, or sodium hydride in an appropriate solvent such as dichloromethane, dichloroethane, chloroform, acetonitrile, tetrahydrofuran, dioxane, toluene, N-dimethylformamide, or N-methylpyrrolidinone. The activated formamide 5-1 can be prepared by treating an appropriate alcohol at an appropriate temperature such as 0° C. or room temperature with a suitable reagent such as phosgene, trichloromethyl chloroformate, 1,1'-carbonyldiimidazole, or p-nitrophenyl chloroformate in the presence of a suitable base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone.

Scheme 5

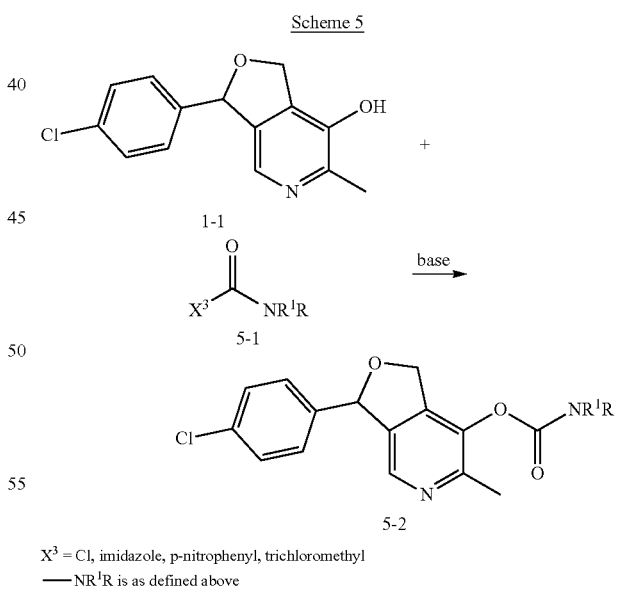

$X^3$ = Cl, imidazole, p-nitrophenyl, trichloromethyl
—$NR^1R$ is as defined above General Procedures.

Reactions sensitive to moisture or air were performed under nitrogen or argon using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC on Waters-C18 XTerra 3.5 μm 2.1×20 mm column with gradient 10:90-98:2 v/v CH$_3$CN/H$_2$O+v 0.05% TFA over 3.25 min then hold at 98:2 v/v CH$_3$CN/H$_2$O+v 0.05% TFA for 0.75 min; flow rate 1.5 mL/min, UV wavelength 254 nm (noted as LC-1) or on Waters C18 XTerra 3.5 μm 30×50 mm column with gradient 10:90-98:2 v/v CH$_3$CN/H$_2$O+v 0.05% TFA over 3.75 min then hold at 98:2 v/v CH$_3$CN/H$_2$O+v 0.05% TFA for 1.75 min; flow rate 1.0 mL/min, UV wavelength 254 nm (noted as LC-2). Concentration of solutions was carried out on a rotary evaporator under reduced pressure. Flash chromatography was performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was performed on one of Chiralpak AS, Chiralpak AD, Chiralcel OD, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, or Chiralcel OJ columns (20×250 mm) (Daicel Chemical Industries, Ltd.) with desired isocratic solvent systems identified on chiral analytical chromatography.

Abbreviations: acetic acid (AcOH), aqueous (aq), (benzotriazol-1-yloxy)tripyrrolidino-phosphonium hexafluorophosphate (PyDOP), ethyl acetate (EtOAc), diethyl ether (ether or Et$_2$O), N,N-diisopropylethylamine (DIEA), N,N-dimethylformamide (DMF), gram(s) (g), hour(s) (h or hr), microliter(s) (μL), milligram(s) (mg), milliliter(s) (mL), millimole (mmol), mass spectrum (ms or MS), 2-propanol (IPA), retention time (R$_t$), room temperature (rt), saturated aq sodium chloride solution (brine), trifluoroacetic acid (TFA), tetrahydrofuran (THF), and minute(s) (min).

Intermediate 1

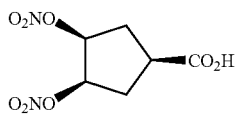

(1r,3R,4S)-3,4-Bis(nitrooxy)cyclopentanecarboxylic acid

Step A: Methyl (3R,4S)-3,4-dihydroxycyclopentanecarboxylate

To a stirred mixture of N-methylmorpholine N-oxide.H$_2$O (30 g, 228 mmol) in H$_2$O (45 mL) and THF (120 mL) was added OsO$_4$ (300 mg) in tert-butyl alcohol (80 mL) and methyl cyclopent-3-ene-1-carboxylate (20 g, 0.114 mol) under nitrogen and the resulting mixture was stirred overnight at room temperature. The reaction mixture was treated with NaHSO$_3$, extracted with CH$_2$Cl$_2$ (3×100 mL), washed with brine (50 mL), dried over Na$_2$SO$_4$, filtered and evaporated in vacuo to give a crude diol (20 g), which was employed in the next step without further purification.

Step B: Methyl (3aR,5r,6aS)-2,2-dimethyltetrahydro-3aH-cyclopenta[d][1,3]dioxole-5-carboxylate and methyl (3aR,5s,6aS)-2,2-dimethyltetrahydro-3aH-cyclopenta[d][1,3]dioxole-5-carboxylate To a solution of the diol (20 g, 0.12 mol) and 2,2-dimethoxypropane (10 mL, 90 mmol) in acetone (400 mL) was added p-toluenesulfonic acid monohydrate (1.5 g, cat.). After stirring at room temperature for 3 h, the mixture was concentrated. The residue was diluted with sodium bicarbonate (50 mL) and extracted with diethyl ether (100 mL×3). The ethereal extracts were washed with sodium bicarbonate (150 mL), water (100 mL) and brine (100 mL), dried over MgSO$_4$ and concentrated in vacuo. The residue was purified by column chromatography to give: (1) methyl (3aR,5r,6aS)-2,2-dimethyltetrahydro-3aH-cyclopenta[d][1,3]dioxole-5-carboxylate (4 g, yield: 16%). $^1$H NMR (400 MHz): δ 4.60-4.62 (m, 2H), 3.68 (s, 3H), 2.77-2.81 (m, 1H), 2.43-2.47 (m, 2H), 1.81-1.89 (m, 2H), 1.38 (s, 3H), 1.25 (s, 3H); and (2) methyl (3aR,5s,6aS)-2,2-dimethyltetrahydro-3aH-cyclopenta[d][1,3]dioxole-5-carboxylate (5 g, yield: 20%). $^1$H NMR (400 MHz): δ 4.64-4.67 (m, 2H), 3.66 (s, 3H), 2.97-3.03 (m, 1H), 2.08-2.13 (m, 2H), 1.66-1.75 (m, 2H), 1.41 (s, 3H), 1.26 (s, 3H).

Step C: Methyl (1r,3R,4S)-3,4-dihydroxycyclopentanecarboxylate

To a solution of methyl (3aR,5r,6aS)-2,2-dimethyltetrahydro-3aH-cyclopenta[d][1,3]dioxole-5-carboxylate (3.4 g, 16.98 mmol) in EtOH (40 mL) was added conc, aq HCl (5.0 mL, 12 M, 60.0 mmol) and the mixture was allowed to stir at room temperature overnight. The mixture was concentrated in vacuo and the residue was purified by column chromatography (Biotage 40+M, 40-100% EtOAc in hexanes) to give the title compound as a pale yellow oil (2.07 g, yield: 76%). $^1$H NMR: δ 4.00-4.20 (m, 2H), 3.60-3.72 (m, 2H), 3.21 (br. s, 1H), 2.80-3.0 (m, 1H), 2.10-2.30 (m, 2H), 1.90-2.00 (m, 2H).

Step D: Methyl (1r,3R,4S)-3,4-bis(nitrooxy)cyclopentanecarboxylate

To a solution of acetic anhydride (20 mL) at 0° C. was added fuming nitric acid (12.0 mL, 187 mmol). The resulting mixture was allowed to stir at 0° C. for 30 min and then to which a solution of the diol (3.0 g, 18.73 mmol) in acetic anhydride (10 mL). After stirring at 0° C. for 3 hrs, the mixture was poured onto ice and neutralized using solid NaHCO$_3$. The mixture was extracted with Et$_2$O (100 mL×3). The organic layers were combined, washed with sat. NaHCO$_3$ and brine, dried over MgSO$_4$, and concentrated. The residue was purified by column chromatography (Biotage 40+M, 15% EtOAc in hexanes) to give the title compound as a colorless oil (2.2 g, yield: 47%): $^1$H NMR: δ 5.40-5.44 (m, 2H), 3.75 (s, 3H), 2.90-2.96 (m, 1H), 2.44-2.50 (m, 2H), 2.33-2.39 (m, 2H).

Step E: (1r,3R,4S)-3,4-Bis(nitrooxy)cyclopentanecarboxylic acid

To a solution of the dinitrate methyl ester (2.2 g, 8.79 mmol) in EtOH (20 mL) was added NaOH (5.3 mL, 5.0 N, 26.4 mmol). After stirring at room temperature for 1 hr, the mixture was acidified using 5.0 N HCl until pH=3 and then extracted with Et₂O (100 mL×3). The organic layers were combined, washed with brine, dried over MgSO₄, and concentrated to give the title compound as a white solid: ¹H NMR: δ 5.40-5.44 (m, 2H), 2.97-3.04 (m, 1H), 2.45-2.53 (m, 2H), 2.37-2.43 (m, 2H).

Intermediate 2

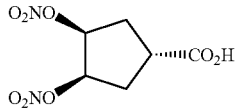

(1s,3R,4S)-3,4-Bis(nitrooxy)cyclopentanecarboxylic acid

The title compound was prepared by following the procedure for INTERMEDIATE 1, except that in Step C, the reagent methyl (3aR,5r,6aS)-2,2-dimethyltetrahydro-3aH-cyclopenta[d][1,3]dioxole-5-carboxylate was replaced by methyl (3aR,5s,6aS)-2,2-dimethyltetrahydro-3aH-cyclopenta[d][1,3]dioxole-5-carboxylate: ¹H NMR: δ 5.56-5.59 (m, 2H), 3.20-3.26 (m, 1H), 2.44-2.50 (m, 2H), 2.29-2.35 (m, 2H).

Intermediate 3

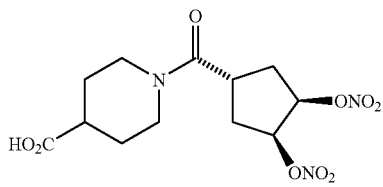

1-{[(1s,3R,4S)-3,4-Bis(nitrooxy)cyclopentyl]carbonyl}piperidine-4-carboxylic acid Step A: Ethyl 1-{[(1s,3R,4S)-3,4-bis(nitrooxy)cyclopentyl]carbonyl}piperidine-4-carboxylate To a solution of INTERMEDIATE 2 (52 mg, 0.22 mmol), ethyl piperidine-4-carboxylate (38 mg, 0.24 mmol), and Et₃N (61 μL, 0.44 mmol) in CH₂Cl₂ at room temperature was added PyBOP (172 mg, 0.33 mmol). After stirring at room temperature for 3 hrs, the mixture was purified using flash chromatography (Biotage 40+S, 35% EtOAc in hexanes) to give the title compound (83 mg, yield: 100%): ¹H NMR δ 5.59-5.64 (m, 2H), 4.35-4.39 (m, 1H), 4.16 (q, J=7.1 Hz, 2H), 3.79-3.84 (m, 1H), 3.33-3.40 (m, 1H), 3.14-3.20 (m, 1H), 2.86-2.91 (m, 1H), 2.54-2.60 (m, 1H), 2.40-2.46 (m, 2H), 2.14-2.21 (m, 2H), 1.94-2.00 (m, 2H), 1.61-1.72 (m, 2H), 1.27 (t, J=7.1 Hz, 3H).

Step B: 1-{[(1s,3R,4S)-3,4-Bis(nitrooxy)cyclopentyl]carbonyl}piperidine-4-carboxylic acid To a solution of the ester (95 mg, 0.25 mmol) in EtOH (5.0 mL) at room temperature was added NaOH (100 μL, 5.0 N, 0.50 mmol). After stirring at room temperature for 3 hrs. the mixture was acidified using 5.0 N HCl until pH~3 and extracted with Et₂O (50 mL×2). The organic layers were combined, washed with brine, dried over MgSO₄, and concentrated to give the title compound: ¹H NMR δ 5.59-5.64 (m, 2H), 4.36-4.40 (m, 1H), 3.81-3.86 (m, 1H), 3.34-3.41 (m, 1H), 3.17-3.23 (m, 1H), 2.89-2.95 (m, 1H), 2.60-2.66 (m, 1H), 2.41-2.47 (m, 2H), 2.15-2.21 (m, 2H), 1.98-2.05 (m, 2H), 1.63-1.74 (m, 2H).

Intermediates 4-6

The following intermediates were prepared using procedures analogous to those described for INTERMEDIATE 3 substituting appropriate amino esters for ethyl piperidine-4-carboxylate and substituting appropriate dinitro carboxylic acids for INTERMEDIATE 2 in Step A.

| Intermediate | HO₂C—R | ¹H NMR (500 MHz, CD₃OD) δ (ppm) |
|---|---|---|
| 4 | ![structure] | 5.70-5.65 (m, 2 H), 4.35-4.32 (m, 1 H), 3.97-3.94 (m, 1 H), 3.57-3.51 (m, 1 H), 3.26-3.20 (m, 1 H), 2.93-2.88 (m, 1 H), 2.64-2.58 (m, 1 H), 2.42-2.34 (m, 2 H), 2.25-2.18 (m, 2 H), 2.02-1.93 (m, 2 H), 1.69-1.53 (m, 2 H). |
| 5 | ![structure] | 5.65-5.59 (m, 2 H), 3.79-3.22 (m, 5 H), 2.60-2.34 (m, 3 H), 2.23-1.71 (m, 6 H), 1.59-1.52 (m, 1 H). |

| Intermediate | HO$_2$C—R | $^1$H NMR (500 MHz, CD$_3$OD) δ (ppm) |
|---|---|---|
| 6 | 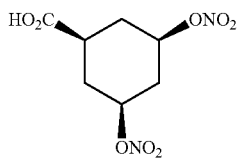 | 5.65 (m, 2 H), 4.51 (m, 1 H), 3.67 (m, 1 H), 3.59 (m, 1 H), 3.31 (m, 1 H), 2.54-2.07 (m, 8 H). |

Intermediate 7

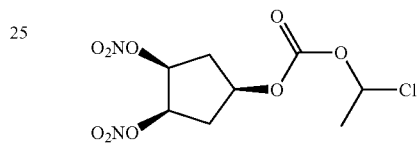

(1r,3R,5S)-3,5-Bis(nitrooxy)cyclohexylcarboxylic acid

Step A: Methyl (1r,3R,5S)-3,5-dihydroxycyclohexanecarboxylate

A solution of 3,5-dihydroxycyclohexanebenzoate (5.0 g, 29.7 mmol) and 5% Rh on alumina (800 mg) in EtOH (50 mL) was stirred at 165° C. under H$_2$ (1000 psi) for 3 days. The mixture was then filtered through Celite and the filtrate was concentrated. The residue was flush through Biotage (40+M) using 5-10% MeOH in CH$_2$Cl$_2$ to give the crude diol (2.4 g), containing some ethyl ester, as a yellow oil, which was used without further purification.

Step B: Methyl (1r,3R,5S)-3,5-bis(nitrooxy)cyclohexanecarboxylate

To a solution of acetic anhydride (28.5 mL) at 0° C. was added fuming nitric acid (8.7 mL, 136 mmol). The resulting mixture was allowed to stir at 0° C. for 30 min and then to which a solution of methyl (1r,3R,5S)-3,5-dihydroxycyclohexanecarboxylate (2.4 g, 13.6 mmol) in acetic anhydride (10 mL). After stirring at 0° C. for 3 hrs, the mixture was poured onto ice and neutralized using solid NaHCO$_3$. The mixture was extracted with Et$_2$O (100 mL×3). The organic layers were combined, washed with sat. NaHCO$_3$ and brine, dried over MgSO$_4$, and concentrated. The residue was purified by column chromatography (Biotage 40+M, 3-10% EtOAc in hexanes) to give the titled compound as a colorless oil (3.1 g, 86%): $^1$H NMR: δ 5.04-4.97 (m, 2H), 3.73 (s, 3H), 2.61-2.54 (m, 2H), 2.48-2.35 (m, 2H), 1.63-1.56 (m, 3H).

Step C: (1r,3R,5S)-3,5-Bis(nitrooxy)cyclohexylcarboxylic acid

To a solution of methyl 3,5-bis(nitrooxy)cyclohexanecarboxylate (3.1 g, 11.7 mmol) in EtOH (20 mL) at room temperature was added NaOH (5.0 N, 7.0 mL, 35 mmol). The mixture was allowed to stir at room temperature for 1 hr and then was acidified using 5.0 N HCl until pH~3. The resulting mixture was extracted with Et$_2$O (100 mL×2). The organic layers were combined, washed with brine (100 mL×2), dried over MgSO4, and concentrated to give the crude title compound as a white solid, which was used without further purification.

Intermediate 8

(1r,3R,4S)-3,4-Bis(nitrooxy)cyclopentyl 1-chloroethyl carbonate

Step A: Cyclopent-3-en-1-yl 4-nitrobenzoate

To a solution of 3-cyclopentene-1-ol (7.0 g, 83.0 mmol) and Et$_3$N (14.5 g, 143.0 mmol) in CH$_2$Cl$_2$ (200 mL) was added 4-nitrobenzoyl chloride (18.5 g, 100.0 mmol) as solid in several portions over a period of 30 min. The resulting suspension was stirred at rt over night. The precipitate was filtered off and the filtrate was washed with water and brine. The organic layer was dried over MgSO$_4$ and concentrated. The residue was purified by flash chromatography (Biotage SP1; column 40M; TLC method: n-hexane/ethyl acetate 9/1; R$_f$=0.50), affording the title product (15.6 g, yield 81%). $^1$H NMR δ 8.28 (d, J=8.9 Hz, 2H), 8.20 (d, J=8.9 Hz, 2H), 5.81 (m, 2H), 5.69 (m, 1H), 2.95 (m, 2H), 2.61 (m, 2H).

Step B: 3,4-Dihydroxycyclopentyl 4-nitrobenzoate

To a solution of cyclopent-3-en-1-yl 4-nitrobenzoate (8.5 g, 36.4 mmol) in the mix solvent of THF (100 mL) and H$_2$O (35 mL) was added 4-methylmorpholine N-oxide (5.12 g, 43.7 mmol) and followed by OsO$_4$ (2.5 wt % in tert-BuOH) (18.53 g, 1.8 mmol). After stirring at rt over night, the mixture was concentrated. The residue was diluted with H$_2$O and extracted with Et$_2$O. The organic layer was dried over MgSO$_4$ and concentrated. The residue was purified by flash chromatography (Biotage SP1; column 40M; TLC method: n-hexane/ethyl acetate 1/9; R$_f$=0.15), affording the title product (7.0 g, yield 72%).

Step C: (3aR,5r,6aS)-2,2-Dimethyltetrahydro-3aH-cyclopenta[d][1,3]dioxol-5-yl 4-nitrobenzoate and (3aR,5s,6aS)-2,2-dimethyltetrahydro-3aH-cyclopenta[d][1,3]dioxol-5-yl 4-nitrobenzoate To a solution of 3,4-dihydroxycyclopentyl 4-nitrobenzoate (7.0 g, 26.2 mmol) in acetone (150 mL) was added 2,2- dimethoxypropane (27.1 g, 260.0 mmol) and followed by TsOH (0.25 g, 1.3 mmol). After stirring at rt over night, the mixture was concentrated and the residue was purified by flash chromatography (Biotage SP1; column 40M; TLC method: n-hexane/ethyl acetate 7/3; $R_f$=0.25), affording the title product (3aR,5r,6aS)-2,2-dimethyltetrahydro-3aH-cyclopenta[d][1,3]dioxol-5-yl 4-nitrobenzoate (3.28 g, yield 41%). $^1$H NMR δ 8.15-8.21 (m, 4H), 5.33-5.35 (m, 1H), 4.71-4.74 (m, 2H), 2.28-2.32 (m, 2H), 1.96-2.03 (m, 2H), 1.36 (s, 3H), 1.20 (s, 3H); (3aR,5s,6aS)-2,2-dimethyltetrahydro-3aH-cyclopenta[d][1,3]dioxol-5-yl 4-nitrobenzoate (3.37 g, yield 42%). $^1$H NMR δ 8.30-8.18 (m, 4H), 5.60-5.52 (m, 1H), 4.77 (m, 2H), 2.48 (m, 2H), 1.84 (m, 2H), 1.50 (s, 3H), 1.32 (s, 3H).

Step D: (1r,3R,4S)-3,4-Dihydroxycyclopentyl 4-nitrobenzoate

To a solution of (3aR,5r,6aS)-2,2-dimethyltetrahydro-3aH-cyclopenta[d][1,3]dioxol-5-yl 4-nitrobenzoate (3.25 g, 10.6 mmol) in THF (25 mL) was added 6.0 N HCl (30 mL). After stirring at rt for 2 d, the mixture was diluted with brine and extracted with Et$_2$O. The organic layer was washed with brine, dried over MgSO$_4$ and concentrated. The residue was purified by flash chromatography (Biotage SP1; column 40M; TLC method: n-hexane/ethyl acetate 7/3; $R_f$=0.25), affording the title product (2.3 g, yield 81%). $^1$H NMR δ 8.31-8.22 (m, 4H), 5.33-5.38 (m, 1H), 4.20 (m, 2H), 2.52-2.46 (m, 4H), 2.11-2.06 (m, 2H).

Step E: (1r,3R,4S)-3,4-Bis(nitrooxy)cyclopentyl 4-nitrobenzoate

To Ac$_2$O (25 mL) cooled at 0° C. was added fuming HNO$_3$ (7.75 g, 86.0 mmol) dropwise. The resulting solution was added dropwise to a suspension of (1r,3R,4S)-3,4-dihydroxycyclopentyl 4-nitrobenzoate (2.31 g, 8.6 mmol) in Ac$_2$O (25 mL) at 0° C. After stirring at 0° C. for 2 hr, the mixture was poured onto ice, warm up to rt, and neutralized by added solid NaHCO$_3$ until pH~7. The mixture was extracted with Et$_2$O. The organic layer was washed with brine, dried over MgSO$_4$ and concentrated. The residue was purified by flash chromatography (Biotage SP1; column 40M; TLC method: n-hexane/ethyl acetate 7/3; $R_f$=0.50), affording the title product (2.91 g, yield 95%). $^1$H NMR δ 8.15-8.21 (m, 4H), 5.55 (m, 1H), 5.30-5.20 (m, 2H), 2.78-2.72 (m, 2H), 2.38-2.30 (m, 2H).

Step F: (1R,2S,4r)-4-Hydroxycyclopentane-1,2-diyl dinitrate

To the solution of (1r,3R,4S)-3,4-bis(nitrooxy)cyclopentyl 4-nitrobenzoate in CH$_3$OH (20 mL) was added 5.0 N NaOH (5 mL) at rt. After stirring for 1 hr, the mixture was partitioned between EtOAc and 1.0N HCl. The organic layer was washed with brine, dried over MgSO$_4$ and concentrated to give the title compound, which was subjected to next step reaction without further purification.

Step G: (1r,3R,4S)-3,4-Bis(nitrooxy)cyclopentyl 1-chloroethyl carbonate

To a solution of (1R,2S,4r)-4-hydroxycyclopentane-1,2-diyl dinitrate in CH$_2$Cl$_2$ (20 mL) at rt was added 1-chloroethyl chloroformate (1.32 g, 9.23 mmol) and followed by pyridine (1.82 g, 23.1 mmol). After stirring at rt over night, the mixture was diluted with H$_2$O and extracted with CH$_2$Cl$_2$. The organic layer was washed with brine, dried over MgSO$_4$ and concentrated. The residue was purified by flash chromatography (Biotage SP1; column 40M; TLC method: n-hexane/ethyl acetate 7/3; $R_f$=0.35), affording the title product. $^1$H NMR δ 6.4 (m, 1H), 5.47 (m, 2H), 5.16 (m, 1H), 2.73-2.68 (m, 2H), 2.31-2.22 (m, 2H), 1.87 (d, J=5.7 Hz, 2H).

Intermediate 9

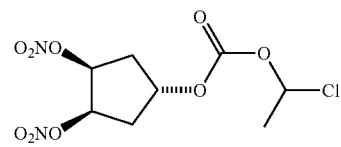

(1s,3R,4S)-3,4-Bis(nitrooxy)cyclopentyl 1-chloroethyl carbonate

The title compound was prepared by following the procedure for INTERMEDIATE 8, except that in Step D, the reagent (3aR,5r,6aS)-2,2-dimethyltetrahydro-3aH-cyclopenta[d][1,3]dioxol-5-yl 4-nitrobenzoate was replaced by (3aR,5s,6aS)-2,2-dimethyltetrahydro-3aH-cyclopenta[d][1,3]dioxol-5-yl 4-nitrobenzoate.

Intermediates 10-12

The following intermediates were prepared using procedures analogous to those described for INTERMEDIATE 8, except that in Step A substituting appropriate alcohols for 3-cyclopentene-1-ol.

| Intermediate | R—CHCH$_3$Cl | 1H NMR (500 MHz, CD$_3$OD) δ (ppm) |
|---|---|---|
| 10 | ![structure] | 6.44 (m, 1 H), 5.47 (m, 2 H), 4.25-4.17 (m, 2 H), 2.50 (m, 1 H), 2.39 (m, 2 H), 1.86-1.79 (m, 5 H) |

| Intermediate | R—CHCH₃Cl | 1H NMR (500 MHz, CD₃OD) δ (ppm) |
|---|---|---|
| 11 | O₂NO⟨cyclopentyl with two O₂NO⟩CH₂-O-C(=O)-O-CH(CH₃)-Cl | 6.42 (m, 1 H), 5.55 (m, 2 H), 4.19 (m, 2 H), 2.76 (m, 1 H), 2.20 (m, 2 H), 2.00 (m, 2 H), 1.86 (d, J = 4.3, 3 H) |
| 12 | O₂NO⟨cyclohexyl⟩-O-C(=O)-O-CH(CH₃)-Cl | 6.40 (m, 1 H), 5.00 (m, 1 H), 4.80 (m, 1 H), 1.99-1.80 (m, 1 H) |

Intermediate 13

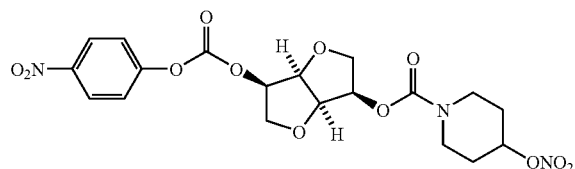

(3R,3aR,6R,6aR)-6-((4-nitrophenoxy)carbonyloxy)hexahydrofuro[3,2-b]furan-3-yl 4-(nitrooxy)piperidine-1-carboxylate

Step A: tert-butyl 4-(nitrooxy)piperidine-1-carboxylate

To a solution of tert-butyl 4-hydroxy-1-piperidinecarboxylate (2.00 g, 9.94 mmol), tetraethylammonium nitrate (3.82 g, 19.9 mmol) and 2,6-di-tert-butyl-4-methylpyridine (5.10 g, 24.9 mmol) in DCM (190 mL) cooled to −70° C. and under nitrogen, a solution of trifluoromethansulfonic anhydride (1.8 mL, 10.9 mmol) in DCM (62 ml) was added dropwise. The resulting mixture was stirred for 3 hrs at −65° C. Then the mixture was slowly warmed to room temperature, diluted with DCM and washed with 5% aqueous sodium dihydrogen phosphate. The organic layer was dried over sodium sulfate, filtered and concentrated, affording the title compound which was used in subsequent steps without further purification

Step B: Piperidin-4-yl nitrate hydrochloride

To a solution of tert-butyl 4-(nitrooxy)piperidine-1-carboxylate (2.10 g; 8.53 mmol) in DCM (15 mL) cooled to 0° C., HCl gas was bubbled for 2 hrs. The solvent was concentrated and the residue was treated with diethyl ether, affording the title compound which was used in subsequent steps without further purification.

Step C: (3R,3aR,6R,6aR)-6-hydroxyhexahydrofuro[3,2-b]furan-3-yl 4-nitrophenyl carbonate To a solution of 1,4:3,6-dianhydro-D-mannitol (3.00 g, 20.5 mmol) and triethylamine (3.15 mL, 22.6 mmol) in DCM (100 ml), 4-nitrophenyl chloroformate (4.55 g, 22.6 mmol) was added and the mixture was stirred at room temperature for 18 hrs. Then the mixture was washed with a 5% solution of sodium dihydrogen phosphate (2×50 mL). The organic layer was dried over sodium sulfate, filtered, concentrated and purified by flash chromatography (Biotage SP1, EtOAc/n-hexane from 20 to 80%), affording the title compound.

Step D: (3R,3aR,6R,6aR)-6-hydroxyhexahydrofuro[3,2-b]furan-3-yl 4-(nitrooxy)piperidine-1-carboxylate To a solution of piperidin-4-yl nitrate hydrochloride (0.620 g, 3.40 mmol), triethylamine (0.567 mL, 4.07 mmol) and 4-dimethylaminopyridine (0.083 g, 0.680 mmol) in DCM (23 mL), (3R,3aR,6R,6aR)-6-hydroxyhexahydrofuro[3,2-b]furan-3-yl 4-nitrophenyl carbonate (1.06 g, 3.40 mmol) was added; the mixture was stirred at room temperature for 18 hrs. Then the mixture was diluted with DCM and washed with a 5% solution of sodium dihydrogen phosphate (2×30 mL) and brine (1×30 mL). The organic layer was dried over sodium sulfate, filtered, concentrated and purified by flash chromatography (Biotage SP1, EtOAc/n-hexane from 30 to 100%), affording the title compound as a yellow oil.

Step E: (3R,3aR,6R,6aR)-4-nitrooxy-piperidine-1-carboxylic acid 6-(4-nitro-phenoxycarbonyloxy)-hexahydro-furo[3,2-b]furan-3-yl ester To a solution of (3R,3aR,6R,6aR)-6-hydroxyhexahydrofuro[3,2-b]furan-3-yl 4-(nitrooxy)piperidine-1-carboxylate (0.47 g, 1.48 mmol) and Et₃N (0.45 g, 4.44 mmol) in THF (25 mL) was added 4-Nitrophenyl chloroformate (0.30 g, 1.48 mmol) as solid. After stirring at rt over night, the mixture was concentrated. The residue was diluted with EtOAc and washed with NaH₂PO₄ 5%. The organic layer was dried over Na₂SO₄ and concentrated. The residue was purified by flash chromatography (Biotage SP1; column SNAP 50; 60% EtOAc in n-hexane), affording the title product as a white solid. ¹H-NMR (300 MHz, CDCl₃); δ 8.33-8.29 (2H, m), 7.45-7.40 (2H, m), 5.22-5.07 (3H, m), 4.88-4.80 (1H, m), 4.79-4.71 (1H, m), 4.20-3.71 (6H, m), 3.60-3.30 (2H, m), 2.12-1.98 (2H, m), 1.88-1.73 (2H, m).

Intermediate 14

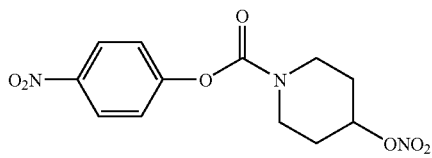

4-Nitrooxy-piperidine-1-carboxylic acid 4-nitro-phenyl ester

To a solution of Piperidin-4-yl nitrate hydrochloride (INTERMEDIATE 13, Step B) (0.40 g, 2.20 mmol) and $Et_3N$ (0.67 g, 6.60 mmol) in $THF/CH_3CN$ 2/1 (24 mL) was added 4-Nitrophenyl chloroformate (0.44 g, 2.20 mmol) as solid. After stirring at rt over night, the mixture was concentrated. The residue was diluted with EtOAc and washed with $NaH_2PO_4$ 5%. The organic layer was dried over $MgSO_4$ and concentrated. The residue was purified by flash chromatography (Biotage SP1; column SNAP 50; TLC method: n-hexane/ethyl acetate 7/3; $R_f$=0.37), affording the title product as a white solid. $^1$H-NMR (300 MHz, $CDCl_3$); δ 8.36-8.25 (2H, m), 7.39-7.28 (2H, m), 5.30-5.18 (1H, m), 4.00-3.50 (4H, m), 2.20-2.06 (2H, m), 2.02-1.86 (2H, m).

Intermediate 15

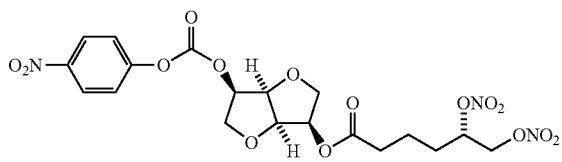

(S)-((3R,3aR,6R,6aR)-6-((4-nitrophenoxy)carbonyloxy)hexahydrofuro[3,2-b]furan-3-yl)5,6-bis(nitrooxy)hexanoate

Step A: tert-butyl hex-5-enoate

To a solution of 5-hexenoic acid (15.2 mL, 0.131 mol) in DCM (375 mL), cooled to 0° C., tert-butanol (176 mL, 1.84 mol) and then 4-dimethylaminopyridine (3.21 g, 26.3 mmol) were added. The mixture was stirred at room temperature for 22 hrs, filtered and concentrated. The residue was redissolved in DCM/n-hexane and concentrated under reduced pressure. The crude oil was purified by flash chromatography (Biotage SP1, EtOAc/n-hexane from 5 to 10%), affording the title product.

Step B: (S)-tert-butyl 5,6-dihydroxyhexanoate

To a suspension of AD-mix-α (70 g) in water/butanol 1:1 (512 mL) cooled to 0° C., tert-butyl hex-5-enoate (8.5 g, 49.92 mmol) was added. The reaction mixture was stirred at 4° C. for 70 hrs. Then the reaction mixture was cooled to 0° C. and EtOAc (280 mL), followed by continuous portionwise addition of sodium metabisulfite (20.6 g). The mixture was stirred for 30 min at 0° C. and at rt for 1 hour. The organic layer was separated and the aqueous phase extracted with ethyl acetate. The combined organic layers were dried over sodium sulfate and concentrated under reduced pressure. Chromatography over silica gel eluting with EtOAc 100% afforded the title compound as a pale yellow oil.

Step C: (S)-tert-butyl 5,6-di(nitrooxy)hexanoate

To a solution of fuming nitric acid (10.25 mL, 247.22 mmol) and acetic anhydride (37.6 mL) cooled to 0° C., a solution of (S)-tert-butyl 5,6-dihydroxyhexanoate (10.1 g, 49.44 mmol) in DCM (10 mL) was added dropwise. The reaction mixture was stirred at 0° C. for 1 hour, adjusted to pH 7 by addition of aqueous NaOH and extracted with DCM. The organic layer was separated and the aqueous phase extracted with ethyl acetate. The combined organic layers were dried over sodium sulfate and concentrated under reduced pressure. The crude residue was purified by flash chromatography (Biotage SP1, EtOAc/n-hexane from 10 to 50%), affording the title product as a pale yellow oil.

Step D: (S)-5,6-di(nitrooxy)hexanoic acid

To a solution of (S)-tert-butyl 5,6-di(nitrooxy)hexanoate (12.41 g, 42.155 mmol) in DCM (47 mL) cooled to 0° C. under $N_2$, boron trifluoride diethyl ether complex (5.82 mL, 46.37 mmol) was added. The reaction mixture was stirred at 0° C. for 10 minutes and at rt for 3 hrs. The solution was washed with brine, the organic layer was separated, dried over sodium sulfate and concentrated under reduced pressure. The crude brown oil was used in the next step without further purification.

Step E: (3R,3aR,6R,6aR)-6-(tetrahydro-2H-pyran-2-yloxy)hexahydrofuro[3,2-b]furan-3-ol To a solution of 1,4:3,6-dianhydro-D-mannitol (5.00 g, 34.2 mmol) in DCM (102 mL) 3,4-dihydro-2H-pyran (3.88 mL, 42.8 mmol) was added, followed by p-toluensulfonic acid (65 mg, 1.34 mmol). The reaction mixture was stirred at rt for 16 hrs. The solution was washed with brine, the organic layer was separated, dried over sodium sulfate and concentrated under reduced pressure. The crude residue was purified by flash chromatography (Biotage SP1, EtOAc/n-hexane from 30 to 100%), affording the title product as pale yellow oil.

Step F: (5S)-((3R,3aR,6R,6aR)-6-(tetrahydro-2H-pyran-2-yloxy)hexahydrofuro[3,2-b]furan-3-yl)5,6-bis(nitrooxy)hexanoate To a solution of (3R,3aR,6R,6aR)-6-(tetrahydro-2H-pyran-2-yloxy)-hexahydrofuro[3,2-b]furan-3-ol (2.96 g, 12.9 mmol) in DCM (40.8 mL) a solution of the crude (S)-5,6-di(nitrooxy)hexanoic acid (3.06 g, 12.85 mmol) (Step D) in DCM (9.15 mL) was added followed by EDAC (3.69 g, 19.28 mmol) and 4-dimethylaminopyridine (175 mg, 1.28 mmol). The reaction mixture was stirred at rt for 16.5 hrs. The solvent was removed under reduced pressure. The crude residue was purified by flash chromatography (Biotage SP1, EtOAc/n-hexane from 10 to 60%), affording the title product as pale yellow oil.

Step G: (S)-((3R,3aR,6R,6aR)-6-hydroxyhexahydrofuro[3,2-b]furan-3-yl)5,6bis(nitrooxy)hexanoate To a solution of (5S)-((3R,3aR,6R,6aR)-6-(tetrahydro-2H-pyran-2-yloxy)-hexahydrofuro[3,2-b]furan-3-yl)5,6-bis(nitrooxy)hexanoate (2.27 g, 5.04 mmol) in ethanol (40 mL) pyridinium p-toluensulfonate (127 mg, 0.504 mmol) was added The reaction mixture was stirred at 45° C. for 4 hrs. The reaction mixture was filtered, concentrated under reduced pressure. The crude residue was purified by flash chromatography (Biotage SP1, EtOAc/n-hexane from 10 to 60%), affording the title product as pale yellow oil. $^1$H-NMR (300 MHz, CDCl$_3$); δ 5.30 (1H, dd), 5.16 (1H, q), 4.77 (1H, d), 4.71 (1H, t), 4.50 (2H, m), 4.26 (1H, m), 4.12 (1H, dd), 3.94 (1H, dd), 3.85 (1H, dd), 3.58 (1H, dd), 2.61 (1H, d), 2.47 (2H, m), 1.83 (4H, m).

Step H: (S)-((3R,3aR,6R,6aR)-6-((4-nitrophenoxy)carbonyloxy)hexahydrofuro[3,2-b]furan-3-yl)5,6-bis(nitrooxy)hexanoate To a solution of (S)-((3R,3aR,6R,6aR)-6-hydroxyhexahydrofuro[3,2-b]furan-3-yl)5,6bis(nitrooxy)hexanoate (0.80 g, 2.18 mmol) and Et$_3$N (0.66 g, 6.54 mmol) in THF (30 mL) was added 4-Nitrophenyl chloroformate (0.44 g, 2.18 mmol) as solid. After stirring at rt over night, the mixture was concentrated. The residue was diluted with EtOAc and washed with NaH$_2$PO$_4$ 5%. The organic layer was dried over MgSO$_4$ and concentrated. The residue was purified by flash chromatography (Biotage SP1; column SNAP 50; TLC method: n-hexane/ethyl acetate 1/1; R$_f$=0.38), affording the title product as a pale yellow oil. $^1$H-NMR (300 MHz, CDCl$_3$); δ 8.32-8.29 (2H, m), 7.44-7.28 (2H, m), 5.33 (1H, m), 5.21-5.05 (2H, m), 4.89-4.65 (3H, m), 4.50 (1H, m), 4.20-3.95 (4H, m), 3.94-3.85 (1H, m), 2.50 (2H, m), 1.84 (4H, m).

Intermediate 16

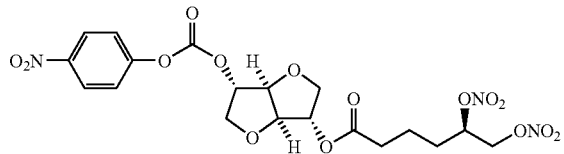

(R)-((3S,3aR,6S,6aR)-6-((4-nitrophenoxy)carbonyloxy)hexahydrofuro[3,2-b]furan-3-yl)5,6-bis(nitrooxy)hexanoate Step A:
(3S,3aR,6S,6aR)-hexahydrofuro[3,2-b]furan-3,6-diyl dibenzoate 1,4:3,6-dianhydro-D-mannitol (3.00 g, 20.53 mmol) was dissolved in THF (40 mL). The solution was cooled (0° C.), then triphenylphosphine (11.85 g, 45.17 mmol), benzoic acid (5.52 g, 45.17 mmol) and diisopropyl azodicarboxylate (8.75 mL, 45.17 mmol) were added. The reaction was allowed to warm to room temperature and stirred for 12 hrs. Then the solvent was removed under reduced pressure and the residue was purified by flash chromatography (Biotage SP1, EtOAc/n-hexane from 10 to 30%), affording of the title compound as a white solid.

Step B:
(3S,3aR,6S,6aR)-hexahydrofuro[3,2-b]furan-3,6-diol

To (3S,3aR,6S,6aR)-hexahydrofuro[3,2-b]furan-3,6-diyl dibenzoate (6.30 g, 17.8 mmol), a mix of NaOH 10%: MeOH=1:1 (60 mL) was added. After stirring at room temperature for 24 hrs, the solvent was evaporated under reduced pressure. Water (30 mL) was added and extraction with EtOAc (30 mL) was carried out. The aqueous layer (pH adjusted to 6 with H$_3$PO$_4$ 5%) was evaporated under reduced pressure to leave a white residue. Tetrahydrofuran was added in a large amount, then the suspension was filtered and the filtrate was concentrated to give the title product as a white solid.

Step C: (R)-((3S,3aR,6S,6aR)-6-((4-nitrophenoxy)carbonyloxy)hexahydrofuro[3,2-b]furan-3-yl)5,6-bis(nitrooxy)hexanoate The title compound was prepared by following the procedure for INTERMEDIATE 15, except that in Step B, the reagent AD-mix-α was replaced by AD-mix-β and in Step E, 1,4:3,6-dianhydro-D-mannitol was replaced by (3S,3aR,6S,6aR)-hexahydrofuro[3,2-b]furan-3,6-diol. $^1$H-NMR (300 MHz, CDCl$_3$); δ 8.33-8.29 (2H, m), 7.43-7.39 (2H, m), 5.38-5.22 (3H, m), 4.85-4.70 (3H, m), 4.58-4.46 (1H, m), 4.20-3.91 (4H, m), 2.50-2.39 (2H, m), 1.90-1.73 (4H, m).

Intermediate 17

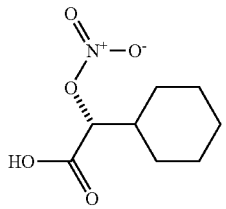

(R)-2-cyclohexyl-2-(nitrooxy)acetic acid

HNO$_3$ (3 mL, 67 mmol) and Ac$_2$O (10 mL) were mixed at 0° C. and after 10 minutes (R)-(−)-hexahydromandelic acid (750 mg, 4.74 mmol) was added. The reaction was stirred at 0° C. for 20 minutes, then poured into iced NaOH (10%) and stirred for 10 minutes.

The aqueous phase was acidified with HCl (3N) to pH 1-2 and extracted with CH$_2$Cl$_2$. The combined organic phases were washed with brine, dried over Na$_2$SO$_4$ and concentrated affording the title compound.

$^1$H-NMR (CDCl$_3$): 9.40 (1H, bs); 5.15 (1H, d, J=4.4 Hz); 1.91 (1H, m); 1.66 (5H, m); 1.20 (5H, m)

Intermediate 18

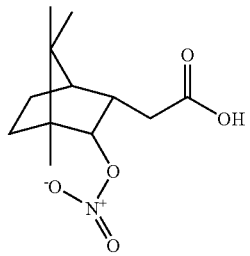

2-(4,7,7-trimethyl-3-(nitrooxy)bicyclo[2.2.1]heptan-2-yl)acetic acid

Title compound was prepared by following the same procedure given for INTERMEDIATE 17 using 2-(4,7,7-trimethyl-3-(hydroxy)bicyclo[2.2.1]heptan-2-yl)acetic acid as a starting material.

$^1$H-NMR (CDCl$_3$): 4.60 (1H, d, J=4.0 Hz); 2.75 (2H, m); 2.58 (1H, m); 1.91 (1H, m); 1.70 (2H, m); 1.38 (1H, m); 1.22 (1H, m); 1.04 (3H, s); 0.91 (6H, s)

Intermediate 19

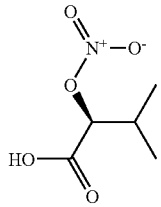

Step A: (S)-3-methyl-2-(nitrooxy)butanoic acid

Title compound was prepared by following the same procedure given for INTERMEDIATE 17 using (S)-(+)-2-hydroxy-3-methylbutyric acid as a starting material.

$^1$H-NMR (CDCl$_3$): 9.40 (1H, bs); 5.05 (1H, d, J=4.5 Hz); 2.39 (1H, m); 1.15 (3H, d, J=7.0 Hz); 1.09 (3H, d, J=7.0 Hz)

Intermediate 20

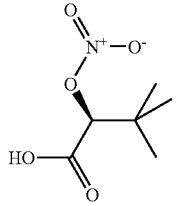

(S)-3,3-dimethyl-2-(nitrooxy)butanoic acid

Title compound was prepared by following the same procedure given for INTERMEDIATE 17 using (S)-(−)-2-hydroxy-3,3-dimethylbutyrric acid as a starting material.

$^1$H-NMR (CDCl$_3$): 9.96 (1H, bs); 4.83 (1H, s); 1.15 (9H, s); 1.15

Intermediate 21

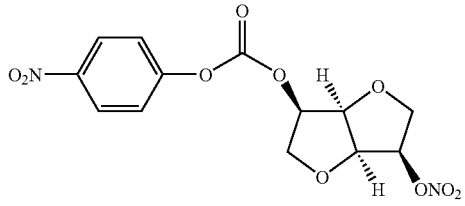

(3R,3aR,6R,6aS)-6-(nitrooxy)hexahydrofuro[3,2-b]furan-3-yl 4-nitrophenyl carbonate Step A: (3R,3aS,6R,6aR)-6-hydroxyhexahydrofuro[3,2-b]furan-3-yl nitrate To a solution of fuming nitric acid (0.92 mL, 22.2 mmol) in CH$_2$Cl$_2$ (44 mL) and acetic anhydride (2.10 mL, 22.2 mmol) cooled to −20° C., 1,4:3,6-dianhydro-D-mannitol (2.50 g, 17.1 mmol) was added as solid. After the reaction mixture was stirred at 0° C. for 3 hours, it was slowly poured into ice/NaHCO$_3$. The organic layer was separated, dried over Na$_2$SO$_4$ and concentrated under reduced pressure. The crude residue was purified by flash chromatography (Biotage SP1, column SNAP 100, EtOAc/n-hexane from 30 to 100%), affording the title product as a white solid (1.35 g, yield 41%).

$^1$H-NMR (300 MHz, CDCl$_3$); δ 5.39 (1H, q), 4.89 (1H, t), 4.49 (1H, t), 4.35-4.27 (1H, m), 4.10-4.04 (2H, m), 3.58 (2H, t), 2.40 (1H, d).

Step B: (3R,3aR,6R,6aS)-6-(nitrooxy)hexahydrofuro[3,2-b]furan-3-yl 4-nitrophenyl carbonate The title compound was prepared by following the procedure for INTERMEDIATE 13 Step H, except that the reagent (S)-((3R,3aR,6R,6aR)-6-hydroxyhexahydrofuro[3,2-b]furan-3-yl)5,6bis(nitrooxy)hexanoate was replaced by (3R,3aS,6R,6aR)-6-hydroxyhexahydrofuro[3,2-b]furan-3-yl nitrate. $^1$H-NMR (300 MHz, CDCl$_3$); δ 8.37-8.21 (2H, m), 7.46-7.33 (2H, m), 5.41-5.29 (1H, m), 5.20-5.05 (1H, m), 4.97-4.75 (2H, m), 4.25-3.91 (4H, m).

Intermediate 22

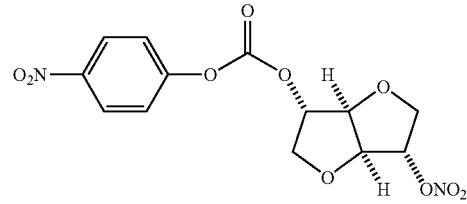

(3S,3aR,6S,6aS)-6-(nitrooxy)hexahydrofuro[3,2-b]furan-3-yl 4-nitrophenyl carbonate The title compound was prepared by following the procedure for INTERMEDIATE 21, except that the reagent 1,4:3,6-dianhydro-D-mannitol was replaced by (3S,3aR,6S,6aR)-hexahydrofuro[3,2-b]furan-3,6-diol (INTERMEDIATE 16 Step B). $^1$H-NMR (300 MHz, CDCl$_3$); δ 8.33-8.14 (2H, m), 7.43-7.38 (2H, m), 5.48-5.42 (1H, m), 5.30-5.24 (1H, m), 4.88-4.80 (2H, m), 4.20-4.00 (4H, m).

Intermediate 23

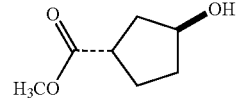

Methyl (1S,3S)-3-hydroxycyclopentanecarboxylate

A solution of methyl (1S,5R)-6-oxabicyclo[3.1.0]hexane-3-carboxylate (8 g, 56.3 mmol) in MTBE (100 ml) was hydrogenated at 3 atm on Parr shaker for 12 hrs. Filtered through celite evaporated followed by chromatagraphy on a 50 g silica gel Biotage Snap cartridge with 10-50% 6:3:1 Hexane-MTBE-MeCN/Hexane to give title compound. $^1$H NMR (500

MHz, CDCl₃) δ 1.63-1.74 (m, 3H), δ 1.78 (s, br, 1H), δ 1.82-2.07 (m, 4H), δ 2.11-2.19 (m, 1H), δ 3.09 (m, 1H), δ 3.70 (s, 3H), δ 4.48 (m, 1H)

Intermediate 24

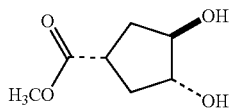

Methyl (3R,4R)-3,4-dihydroxycyclopentanecarboxylate

Methyl (1S,5R)-6-oxabicyclo[3.1.0]hexane-3-carboxylate (8 g, 56.3 mmol) and tetrabutylammonium bisulfate (1.911 g, 5.63 mmol) were suspended in THF (5 ml) and water (75 ml) and allowed to stir for 48 hrs. Added solid NaCl and extracted with three 250 ml portions of EtOAc. Added 100 ml Hexane washed with brine and dryed over sodium sulfate. Silca gel chromatography on a 50 g Biotage SNAP cartridge with 40-60% acetone-hexane to give title product as a clear oil. ¹H NMR (500 MHz, CDCl₃) δ 1.89-2.03 (m, 3H), δ 2.26-2.42 (m, 3H), δ 3.08-3.15 (m, 1H), δ 3.74 (s, 3H), δ 4.06 (m, 1H), δ 4.23 (m, 1H)

Intermediate 25

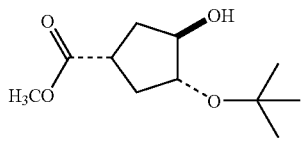

Methyl (1R,3R,4R)-3-tert-butoxy-4-hydroxy-cyclopentanecarboxylate

Methyl (3R,4R)-3,4-dihydroxycyclopentanecarboxylate (1.3 g, 8.12 mmol) was added to a suspension of magnesium perchlorate (0.181 g, 0.812 mmol) in with DCM (5 ml). A solution of di-tert-butyl dicarbonate (3.90 g, 17.86 mmol) in 10 ml DCM in an addition funnel was added dropwise to flask at 40° C. (oil bath) and stirred for 3 hr at which time the bubbling stopped. Silica gel TLC (8% IPA/hexane) showed reaction complete. Reaction was quenched with 50 ml water and extracted twice with DCM. Filtered DCM solution through a pad of silica then washed silica with 10% Acetone/DCM until all product eluted. Concentrated and silica gel chromatography on a 100 g SNAP cartridge with 5-20% IPA/Hex to give the faster eluting regioisomer and slower eluting title compound. ¹H NMR (500 MHz, CDCl₃) δ 1.23 (s, 9H), δ 1.74-1.88 (m, 3H), δ 2.25-2.34 (m, 1H), δ 2.92-2.99 (m, 1H), δ 3.71 (s, 3H), δ 3.76-3.80 (m, 1H), δ 4.05 (dd. J=5.1 Hz, 1H)

The racemic mixture was separated into its enantiomers by SFC chromatography on a Chiral Pak IA column using 15% CH₃OH and 85% CO2. Slower enantiomer [α]_D +38.6° (1.0, CHCl₃)α=. Faster enantiomer [α]_D −39.2° (1.0, CHCl₃)

Intermediate 26

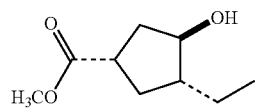

Methyl (1S,3R,4R)-3-ethyl-4-hydroxy-cyclopentanecarboxylate

To a suspension of copper(I) iodide (4.95 g, 26.0 mmol) in 50 ml ether at −25° C. was added ethyllithium (1.7M, 30.6 ml, 52.0 mmol) dropwise. The solution was stirred for 1 hr at −25° C. followed by dropwise addition of an ether solution (50 ml) of methyl (1S,5R)-6-oxabicyclo[3.1.0]hexane-3-carboxylate (1.848 g, 13 mmol) maintaining at −25° C. The reaction was allowed to warm to rt until TLC showed complete reaction. Cooled in ice and quenched with NH4Cl (sat)(5 ml) and stirred for 10 minutes. Filtered thru celite and washed with ether (3×10 ml) and the combined filtrates were washed with brine and dryed over sodium sulfate. Silica gel chromatagraphy on a 25 g Biotage SNAP column with 10-50% MTBE/Hexane afforded title compound. ¹H NMR (500 MHz, CDCl₃) δ 0.96 (t, J=7.3 Hz, 3H), δ 1.24-1.48 (m, 2H), δ 1.54-1.77 (m, 3H), δ 1.83-1.90 (m, 1H), δ 2.12-2.29 (m, 2H), δ 3.02 (m, 1H), δ 3.69 (s, 3H), δ 3.98 (m, 1H)

Intermediate 27

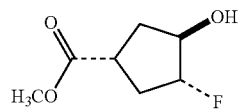

Methyl (1R,3R,4R)-3-fluoro-4-hydroxy-cyclopentanecarboxylate

To a solution of methyl (1S,5R)-6-oxabicyclo[3.1.0]hexane-3-carboxylate (300 mg, 2.110 mmol) in 3 ml of dichloroethane in a Teflon tube was added hydrogen fluoride-pyridine (0.190 ml, 2.110 mmol and allowed to stir at ambient for 6 hrs. Carefully poured onto 5 ml ice/NaHCO3 and extracted with three portions of DCM. Dried over sodium sulfate followed by Silica gel chromatgraphy with 30-50% Acetone-hexane to give title compound. ¹H NMR (500 MHz, CDCl₃) δ 1.96-2.03 (m, 1H), δ 2.12-2.32 (m, 3H), δ 2.38-2.52 (m, 1H), δ 3.12 (m, 1H), δ 3.72 (s, 3H), δ 4.34 (m, 1H), δ 4.86 (d of m, J=51.5 Hz, 1H)

Intermediate 28

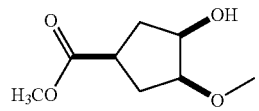

Methyl (1S,3R,4S)-3-hydroxy-4-methoxy-cyclopentanecarboxylate

Methyl (3S,4R)-3,4-dihydroxycyclopentanecarboxylate (0.481 g, 3 mmol), freshly prepared silver oxide (0.348 g, 1.500 mmol) and methyl iodide (0.375 ml, 6.00 mmol) were combined in DMF and allowed to stir for 3 hrs. The reaction mixture was filtered through celite and washed with 15 ml of ether. The organic filtrate was washed 2× with brine, dried over sodium sulfate and evaporated. Purification by silica gel chromatography eluting with 20-40% acetone hexane gave the title compound. $^1$H NMR (500 MHz, CDCl$_3$) δ 2.01-2.18 (m, 4H), δ 2.48 (s, br, 1H), δ 2.77 (m, 1H), δ 3.40 (s, 3H) δ 3.6-3.65 (m, 1H), δ 3.71 (s, 3H), δ 4.10 (m, 1H)

Intermediate 29

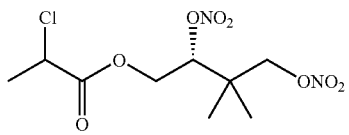

(R)-3,3-dimethyl-2,4-bis(nitrooxy)butyl 2-chloropropanoate

Step A: (2R)-3,3-dimethylbutane-1,2,4-triol

To a stirred suspension of lithium aluminium hydride (3.00 g, 79.1 mmol) in dry THF (100 mL) at 0° C. was added a solution of (R)-pantolactone (10.30 g, 79.14 mmol) in THF (100 mL). The mixture was stirred overnight at room temperature and was then heated to reflux for a further 2 h. The mixture was cooled to 0° C. and the reaction was quenched with saturated aqueous Na$_2$SO$_4$ until a white solid precipitated. The solid was filtered off, the filter cake was washed with THF (2×60 mL) and the filtrate was concentrated under reduced pressure to give the title compound as a pure colorless oil.

Step B: [(2R,4R)-2-(4-methoxyphenyl)-5,5-dimethyl-1,3-dioxan-4-yl]methanol

To a stirred solution of compound obtained in Step A (5.6 g, 41.76 mmol) in dry CH$_2$Cl$_2$ (115 mL) was added p-methoxybenzaldehyde dimethyl acetal (11.42 g, 62.64 mmol) and pyridinium p-toluenesulfonate (2.1 g, 8.35 mmol). The mixture was heated at reflux for 18 h, then was cooled to room temperature and the reaction was quenched with saturated aqueous NaHCO3 solution (50 mL). The separated aqueous layer was extracted with Et2O (3×75 mL) and the combined extracts were washed with saturated aqueous NaCl solution (100 mL) and dried (MgSO4). Filtration and concentration of the filtrate in vacuo left a residue which was purified by flash chromatography (silica gel, gradient elution from 20% Et2O in hexanes to 40% Et2O in hexanes) to give the title compound as a colorless oil.

Step C: [(2R,4R)-2-(4-methoxyphenyl)-5,5-dimethyl-1,3-dioxan-4-yl]methyl 4-nitrobenzoate To a stirred solution of compound obtained in Step B (3.59 g, 14.24 mmol) and TEA (1.98 ml, 14.24 mmol) in DCM (50 ml), 4-Nitrobenzoyl chloride (2.64 g, 14.24 mmol) was added and the reaction was stirred overnight at r.t. The organic phase was washed with a solution of NaH$_2$PO$_4$ 5% and brine, dried (MgSO$_4$) and evaporated under reduced pressure. The crude was crystallized from EtOAc at 0° C. adding n-hexane. The product was obtained as a pale yellow solid.

Step D: (2R)-2,4-dihydroxy-3,3-dimethylbutyl 4-nitrobenzoate

A solution of compound obtained in Step C (4.4 g, 10.96 mmol) in THF (5 ml) and acetic acid (70%) (50 ml) was heated at 60° C. for 4 hours. The solvent was concentrated under reduced pressure and dissolved in EtOAc. The organic layer was washed with NaHCO$_3$ and brine. The organic phase was concentrated under reduced pressure and the crude was crystallized from Et2O and n-Hexane at 0° C. to give a white solid.

Step E: (2R)-3,3-dimethyl-2,4-bis(nitrooxy)butyl 4-nitrobenzoate

A solution of compound obtained in Step D (2.11 g, 7.4 mmol) in DCM (3 ml) was added into a solution of nitric acid (1.8 ml, 44.4 mmol) in acetic anhydride (12 ml) at 0° C. under nitrogen atmosphere. The reaction was stirred for 30 min then was quenched adding it into a solution of ice/NaOH 10%. The aqueous phase was extracted with DCM and the organic phase was washed with brine, dried (MgSO4) and concentrated in vacuo.

Step F: (3R)-4-hydroxy-2,2-dimethyl-3-(nitrooxy)butyl nitrate

At 0° C., to a stirred solution of compound obtained in Step E (2.38 g, 6.37 mmol) in tetrahydrofuran/ethanol (5 mL of each) was added methanol (0.5 mL) and potassium carbonate (1 g, 7.64 mmol). The reaction was stirred for 2 h at 0° C. then diluted with EtOAc and water. The organic layer was separated and washed successively with water and brine, dried on Na$_2$SO$_4$, filtered and evaporated. The residue was purified by flash chromatography (Biotage System, SNAP Cartridge silica 100 g, eluent: n-hexane/ethyl acetate 75/25 to n-hexane/ethyl acetate 60/40 during 15 CV) to give compound F as an oil Step G: (R)-3,3-dimethyl-2,4-bis(nitrooxy)butyl 2-chloropropanoate The title compound was prepared by following the procedure described in INTERMEDIATE 8, Step G.
$^1$H NMR (CDCl$_3$): 5.41 (1H, m); 5.33 (1H, m); 4.61 (1H, m); 4.34 (3H, m); 1.85 (3H, dd); 1.18 (6H, dd).

Intermediate 30

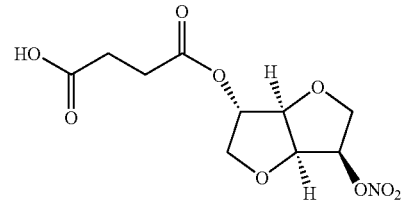

4-((3S,3aR,6R,6aS)-6-(nitrooxy)hexahydrofuro[3,2-b]furan-3-yloxy)-4-oxobutanoic acid To a solution of D-isosorbide-5-mononitrato (0.800 g, 4.19 mmol) in dichloromethane (25 mL), triethylamine (0.876 mL, 6.29 mmol) were added; then succinic anhydride (0.554 g, 5.44 mmol) was slowly added. The mixture was stirred at rt overnight. Then the mixture was diluted with dichloromethane and washed with 5% solution of NaH$_2$PO$_4$ (2×50 mL). The organic layer was dried over sodium sulfate, filtered and evaporated in vacuo, affording the desired product as a colourless oil.

$^1$H NMR (300 MHz, DMSO) δ: 5.48 (m, 1H), 5.09 (m, 1H), 4.97 (m, 1H), 4.40 (m, 1H), 4.02-3.77 (m, 4H), 2.56-2.43 (m, 4H).

Intermediates 31-32

The following intermediates were prepared using procedures analogous to that described for INTERMEDIATE 30, substituting appropriate alcohols for (3R,3aS,6S,6aR)-6-hydroxyhexahydrofuro[3,2-b]furan-3-yl nitrate

| Intermediate | | 1H NMR (300 MHz, DMSO) δ (ppm) |
|---|---|---|
| 31 | 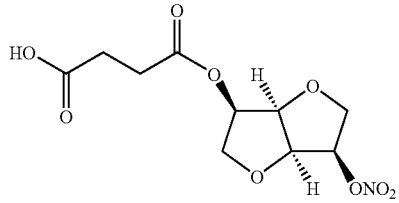 | 5.48 (m, 1 H), 4.99 (m, 1 H), 4.85 (m, 1 H), 4.60 (m, 1 H), 4.08-3.90 (m, 3 H), 3.52 (m, 1 H), 2.61-2.42 (m, 4 H) |
| 32 | 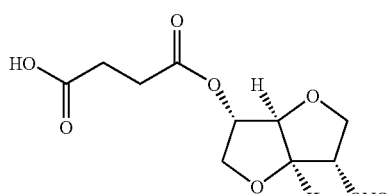 | 5.44 (m, 1 H), 5.08 (m, 1 H), 4.81 (m, 1 H), 4.56 (m, 1 H), 4.09-3.81 (m, 4 H), 2.55-2.23 (m, 4 H) |

INTERMEDIATES 31, 32 compound names:
4-((3R,3aR,6R,6aS)-6-(nitrooxy)hexahydrofuro[2,3-b]furan-2-yloxy)-4-oxobutanoic acid
4-((3S,3aR,6S,6aS)-6-(nitrooxy)hexahydrofuro[2,3-b]furan-2-yloxy)-4-oxobutanoic acid Example 1

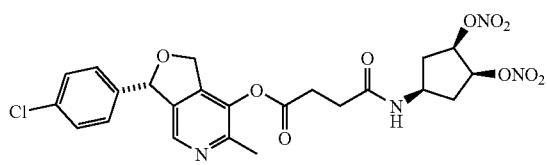

(3S)-3-(4-Chlorophenyl)-6-methyl-1,3-dihydrofuro[3,4-c]pyridin-7-yl 4-{[(1r,3R,4S)-3,4-bis(nitrooxy)cyclopentyl]amino}-4-oxobutanoate Step A: Cyclopent-3-en-1-yl 4-nitrobenzoate To a solution of 3-cyclopentene-1-ol (7.0 g, 83.0 mmol) and Et$_3$N (14.5 g, 143.0 mmol) in CH$_2$Cl$_2$ (200 mL) was added 4-nitrobenzoyl chloride (18.5 g, 100.0 mmol) as solid in several portions over a period of 30 min. The resulting suspension was stirred at room temperature over night. The precipitate was filtered off and the filtrate was washed with water and brine. The organic layer was dried over MgSO$_4$ and concentrated under reduced pressure. The residue was purified by flash chromatography (Biotage SP1; column 40M; TLC method: n-hexane/ethyl acetate 9/1; R$_f$=0.50), affording the title product (15.6 g, yield 81%): $^1$H NMR (500 MHz, CDCl$_3$) δ 8.28 (d, J=8.9 Hz, 2H), 8.20 (d, J=8.9 Hz, 2H), 5.81 (m, 2H), 5.69 (m, 1H), 2.95 (m, 2H), 2.61 (m, 2H).

Step B: (3R,4S)-Dihydroxycyclopentyl 4-nitrobenzoate

To a solution of cyclopent-3-en-1-yl 4-nitrobenzoate (8.5 g, 36.4 mmol) in the mix solvent of 100 mL THF and 35 mL water was added 4-methylmorpholine 4-oxide (5.12 g, 43.7 mmol), followed by osmium tetroxide (2.5% wt. solution in 2-methyl-2-propanol) (18.5 g, 1.8 mmol). The mixture was stirred at room temperature over night. The mixture was concentrated under reduced pressure. The residue was diluted with water and extracted with Et$_2$O. The organic layer was dried over MgSO$_4$ and concentrated under reduced pressure. The residue was purified by flash chromatography (Biotage SP1; column 40M; TLC method: n-hexane/ethyl acetate 1/9; R$_f$=0.15), affording the title product (7.0 g, yield 72%).

Step C: 2,2-(3aR,5r,6aS)-Dimethyltetrahydro-3aH-cyclopenta[d][1,3]dioxol-5-yl 4-nitrobenzoate and 2,2-(3aR,5s,6aS)-Dimethyltetrahydro-3aH-cyclopenta[d][1,3]dioxol-5-yl 4-nitrobenzoate To a solution of (3R,4S)-dihydroxycyclopentyl 4-nitrobenzoate (7.0 g, 26.2 mmol) in acetone (150 mL) was added 2,2-dimethoxypropane (27.1 g, 260.0 mmol), followed by p-toluenesulfonic acid (0.25 g, 1.3 mmol). The mixture was stirred at room temperature over night and then concentrated. The residue was purified by flash chromatography (Biotage SP1; column 40M; TLC method: n-hexane/ethyl acetate 7/3; R$_f$=0.25), affording: 2,2-(3aR,5r,6aS)-dimethyltetrahydro-3aH-cyclopenta[d][1,3]dioxol-5-yl 4-nitrobenzoate (3.28 g, yield 41%): $^1$H NMR (500 MHz, CDCl$_3$) δ 8.15-8.21 (m, 4H), 5.33-5.35 (m, 1H), 4.71-4.74 (m, 2H), 2.28-2.32 (m, 2H), 1.96-2.03 (m, 2H), 1.36 (s, 3H), 1.20 (s, 3H); 2,2-(3aR,5s,6aS)-dimethyltetrahydro-3aH-cyclopenta[d][1,3]dioxol-5-yl 4-nitrobenzoate (3.37 g, yield 42%): $^1$H NMR (500 MHz, CDCl$_3$) δ 8.30-8.18 (m, 4H), 5.60-5.52 (m, 1H), 4.77 (m, 2H), 2.48 (m, 2H), 1.84 (m, 2H), 1.50 (s, 3H), 1.32 (s, 3H).

Step D: (1s,3R,4S)-3,4-Dihydroxycyclopentyl 4-nitrobenzoate

To a solution of (3aR,5s,6aS)-2,2-dimethyltetrahydro-3aH-cyclopenta[d][1,3]dioxol-5-yl 4-nitrobenzoate (3.25 g, 10.6 mmol) in THF (25 m) was added HCl (30 mL, 6.0 N). After stirring at room temperature for 2 days, the mixture was diluted with brine, and extracted with Et$_2$O. The organic layer was washed with brine, dried over MgSO$_4$ and concentrated under reduced pressure. The residue was purified by flash chromatography (Biotage SP1; column 40M; TLC method: n-hexane/ethyl acetate 7/3; R$_f$=0.25), affording the title product (2.3 g, yield 81%): $^1$H NMR (500 MHz, CDCl$_3$) δ 8.31-8.22 (m, 4H), 5.33-5.38 (m, 1H), 4.20 (m, 2H), 2.52-2.46 (m, 4H), 2.11-2.06 (m, 2H).

Step E: (1s,3R,4S)-3,4-Bis(nitrooxy)cyclopentyl 4-nitrobenzoate

To a cooled at 0° C. 25 mL acetic anhydride was added nitric acid (fuming) (7.75 g, 86.0 mmol) dropwise. The resulting solution was added dropwise to a cooled at 0° C. suspension of (1r,3R,4S)-3,4-dihydroxycyclopentyl 4-nitrobenzoate (2.31 g, 8.6 mmol) in acetic anhydride (25 mL). After stirring at 0° C. for 2 hours, the mixture was poured onto ice. It was allowed to warm up to room temperature and neutralized by added solid sodium bicarbonate until pH=7, then it was extracted with Et$_2$O. The organic layer was washed with brine, dried over MgSO$_4$ and concentrated under reduced pressure. The residue was purified by flash chromatography (Biotage SP1; column 40M; TLC method: n-hexane/ethyl acetate 7/3; R$_f$=0.50), affording the title product (2.91 g, yield 95%): $^1$H NMR (500 MHz, CDCl$_3$) δ 8.15-8.21 (m, 4H), 5.55 (m, 1H), 5.30-5.20 (m, 2H), 2.78-2.72 (m, 2H), 2.38-2.30 (m, 2H).

Step F: (1R,2S,4s)-4-Hydroxycyclopentane-1,2-diyl dinitrate

To a solution of (1r,3R,4S)-3,4-bis(nitrooxy)cyclopentyl 4-nitrobenzoate in MeOH (20 mL) was added NaOH (5 mL, 5.0 N) at room temperature. After stirring for 1 hr, the mixture was partitioned between EtOAc and 1.0N HCl. The organic layer was separated, washed with brine, dried over MgSO$_4$ and concentrated under reduced pressure to give the title compound, which was subjected to next step reaction without further purification.

Step G: (1R,2S,4r)-4-Azidocyclopentane-1,2-diyl dinitrate

To a suspension of (1R,2S,4r)-4-hydroxycyclopentane-1,2-diyl dinitrate (230 mg, 1.11 mmol), triphenylphosphine (580 mg, 2.21 mmol), imidazole (301 mg, 4.42 mmol, and pyridine-bis(triaza-1,2-dien-2-ium-1,3-diide-κN$^1$)zinc (2:1) complex (680 mg, 2.21 mmol) in CH$_2$Cl$_2$ (10 mL) at room temperature was added diisopropyl azodicarboxylate (447 m, 2.21 mmol) dropwise. The mixture was allowed to stir at room temperature over night. The supernatant was diluted with Et$_2$O/EtOAc (1:1, 100 mL), washed with diluted HCl (0.1 N, 50 mL×3), sat. NaHCO$_3$ (50 mL×3), and brine. The organic layer was separated, dried over MgSO$_4$ and concentrated under reduced pressure. The residue was purified by flash chromatography (Biotage 40+M using 20% EtOAc in hexanes), affording the title product (250 mg, yield 97%): $^1$H NMR (500 MHz, CDCl$_3$) δ 5.44-5.40 (m, 2H), 4.04-4.01 (m, 1H), 2.60-2.54 (m, 2H), 2.10-2.04 (m, 2H).

Step H: (1R,2S,4r)-4-Aminocyclopentane-1,2-diyl dinitrate

To a solution of (1R,2S,4r)-4-azidocyclopentane-1,2-diyl dinitrate (250 mg, 1.07 mmol) in THF (10 mL) at room temperature was added H$_2$O (0.5 mL) and trimethylphosphine (1.0 M, 1.6 mL, 1.6 mmol). After stirring at room temperature for 3 hrs, the reaction mixture was concentrated in vacuo to give the crude title compound (222 mg), which was used without further purification.

Step I: 4-{[(1r,3R,4S)-3,4-bis(nitrooxy)cyclopentyl]amino}-4-oxobutanoic acid

A mixture of (1R,2S,4r)-4-aminocyclopentane-1,2-diyl dinitrate (222 mg, 1.07 mmol), succinic anhydride (129 mg, 1.29 mmol), and triethylamine (299 μL, 2.14 mmol) in CH$_2$Cl$_2$ (10 mL) was allowed to stir at room temperature over night. The reaction mixture was then partitioned between Et$_2$O (50 mL) and HCl (0.1 N, 50 mL). The organic layer was separated, washed with HCl (0.1 N, 50 mL) and brine, dried over MgSO$_4$, and concentrated in vacuo to give the crude title compound, which was used without further purification.

Step J: (3S)-3-(4-Chlorophenyl)-6-methyl-1,3-dihydrofuro[3,4-c]pyridin-7-yl 4-{[(1r,3R,4S)-3,4-bis(nitrooxy)cyclopentyl]amino}-4-oxobutanoate To a solution of 4-{[(1r,3R,4S)-3,4-bis(nitrooxy)cyclopentyl]amino}-4-oxobutanoic acid (173 mg, 0.56 mmol) and (+)-cicletanine (73.7 mg, 0.28 mmol) in CH$_2$Cl$_2$ (10 mL) at room temperature was added triethylamine (157 μL, 1.12 mmol) and BOP-Cl (172 mg, 0.68 mmol). The mixture was allowed to stir at room temperature over night. The reaction mixture was purified using preparative thin layer chromatography (using 80% EtOAc in hexanes), affording the title product as a white solid: $^1$H NMR (500 MHz, CDCl$_3$) δ 8.05 (s, 1H), 7.34 (d, J=8.4 Hz, 2H), 7.26 (d, J=8.2 Hz, 2H), 6.19 (s, 1H), 5.96 (d, J=8.0 Hz, 1H), 5.19-5.16 (m, 2H), 5.17 (dd, J=2.2, 14.0 Hz, 1H), 5.04 (dd, J=1.6, 14.0 Hz, 1H), 4.54-4.50 (m, 1H), 2.96-2.93 (m, 2H), 2.64-2.58 (m, 4H), 2.46 (s, 3H), 1.89-1.84 (m, 2H);); LC-MS: m/z 551.2 (M+H). (R$_t$=1.84 min).

Examples 2-5

The following EXAMPLES were prepared using procedures analogous to those described for EXAMPLE 1 substituting appropriate acid for 4-{[(1r,3R,4S)-3,4-bis(nitrooxy)cyclopentyl]amino}-4-oxobutanoic acid in Step J.

| EXAMPLE | —X—R | HPLC R₁ (min) | MS (M + H) |
|---|---|---|---|
| 2 | [4-methylpiperidine-1-carbonyl linked to cyclopentyl with two ONO₂ groups] | 2.07 (LC-1) | 591.2 |
| 3 | [piperidine-4-yl carbonyl linked to cyclopentyl with two ONO₂ groups] | 1.96 (LC-1) | 591.0 |
| 4 | [piperidine-3-yl carbonyl linked to cyclopentyl with two ONO₂ groups] | 2.11 (LC-1) | 591.3 |
| 5 | [pyrrolidine-2-yl carbonyl linked to cyclopentyl with two ONO₂ groups] | 3.35 (LC-2) | 577.3 |

Examples 6-7

The following EXAMPLES were prepared using procedures analogous to those described for EXAMPLE 1 substituting appropriate acid for 4-{[(1r,3R,4S)-3,4-bis(nitrooxy)cyclopentyl]amino}-4-oxobutanoic acid in Step J.

| EXAMPLE | —X—R | HPLC R₁ (min) | MS (M + H) |
|---|---|---|---|
| 6 | [alkyl chain with ONO₂] | 3.30 (LC-2) | 421.3 |
| 7 | [norbornyl with ONO₂] | 3.82 (LC-2) | 501.0 |

Example 8

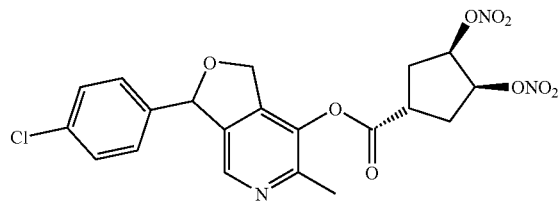

3-(4-chlorophenyl)-6-methyl-1,3-dihydrofuro[3,4-c]
pyridin-7-yl(1s,3R,4S)-3,4-bis(nitrooxy)cyclopen-
tanecarboxylate

Step A: Methyl (1s,3R,4S)-3,4-dihydroxycyclopentanecarboxylate and methyl (1r,3R,4S)-3,4-dihydroxycyclopentanecarboxylate To a stirred solution of methyl cyclopent-3-ene-1-carboxylate (26 g, 206 mmol) and 4-methylmorpholine-N-oxide (26.6 g, 227 mmol) in 500 ml t-Butanol was added a 4% aqueous solution of osmium tetroxide (25.2 ml, 4.12 mmol), dropwise, and the mixture was stirred at rt. After 8 h, NMR of an aliquot showed no more starting olefin. The solution was concentrated to about 200 ml and then diluted with 300 mg sodium bisulfite and 250 ml water. The aqueous solution was extracted with three 300 mL portions of a 9:1 ether-dichloromethane mixture and the combined organic layers were washed NaHCO3, water and brine. The organic extract was dried over Na2SO4, filtered and concentrated. The oily residue was applied to column of silica gel in a 2 l fritted funnel that was packed in hexane. The column was eluted with step gradient of ether-hexane (500 mL portions of 10%, 20%, 30%, 40% and 50% ether-hexane), then with a step gradient of acetone-hexane (1 L portions of 5%, 10% and 15%). The column was then washed with 15% acetone-hexane to afford methyl (1s,3R,4S)-3,4-dihydroxycyclopentanecarboxylate; $^1$H NMR (500 MHz, CDCl$_3$) δ 1.9-2.06 (m, 2H), 2.08-2.16 (m, 2H), 2.58 (s, br, 2H), 3.18 (m, 1H), 3.50 (s, 3H), 4.20 (m, 2H).

Further elution of the column afforded methyl (1r,3R,4S)-3,4-dihydroxycyclopentanecarboxylate;
$^1$H NMR (500 MHz, CDCl$_3$) δ 1.85-2.0 (m, 2H), 2.18-2.26 (m, 2H), 2.84 (m, 1H), 2.92 (s, br, 2H), 3.73 (s, 3H), 4.06 (m, 2H).

Step B: Methyl (1s,3R,4S)-3,4-bis(nitrooxy)cyclopentanecarboxylate

A solution of acetic anhydride (20 ml, 212 mmol) was cooled to 0° C. in an ice bath and then fuming nitric acid (10 ml, 270 mmol) was added dropwise with stirring. The solution was stirred at 0° C. for 10 min and then a solution of methyl (1s,3R,4S)-3,4-dihydroxycyclopentanecarboxylate (8.01 g, 50 mmol) in 20 ml dichloromethane was added dropwise at such a rate that the temperature of the solution remained below 10° C. After addition was complete, the mixture was stirred at 0° C. for 30 min.

The cold solution was poured onto 500 mL of ice water and the mixture was stirred for 10 min. Then 300 mL of dichloromethane was added and the layers were separated. The aqueous layer was washed with 200 mL dichloromethane and the organic extracts were washed with two 200 mL portions of aqueous NaHCO3 solution, 200 mL water and 200 mL brine. The organic layer was dried over Na2SO4, filtered, concentrated and dried under vacuum to give the title compound as a clear oil: $^1$H NMR (500 MHz, CDCl$_3$) δ 2.2-2.3 (m, 2H), 2.4-2.5 (m, 2H), 3.20 (m, 1H), 3.76 (s, 3H), 5.60 (m, 2H).

Step C: (1s,3R,4S)-3,4-bis(nitrooxy)cyclopentanecarboxylic acid

A solution of methyl (1s,3R,4S)-3,4-bis(nitrooxy)cyclopentanecarboxylate in 300 mL methanol was cooled to 0° C. A sample of KOH (6.17 g, 110 mmol) was dissolved in 25 ml water and this solution was added dropwise. The solution was stirred for 2 hr, until hydrolysis was complete. The pH of the solution was adjusted to 7 by addition of 6 M HCl and the methanol was removed under vacuum. The aqueous residue was acidified to pH 4 with 6M HCl and 200 mL chloroform was added. The layers were separated and the aqueous layer was washed with two more 200 mL portions of chloroform. The combined organic extracts were dried over Na2SO4, filtered and concentrated to afford the title compound as a solid; $^1$H NMR (500 MHz, CDCl$_3$) δ 2.2-2.3 (m, 2H), 2.4-2.5 (m, 2H), 3.20 (m, 1H), 5.60 (m, 2H).

Step D: (1R,2S,4S)-4-(chlorocarbonyl)cyclopentane-1,2-diyl dinitrate

A 2M solution of oxalyl chloride in dichloromethane (80 ml, 160 mmol) was added dropwise to a stirred solution of (1s,3R,4S)-3,4-bis(nitrooxy)cyclopentanecarboxylic acid (9.45 g, 40 mmol) in 50 mL dichloroethane that had been cooled to 0° C. in an ice bath. Then 100 uL DMF was added and the solution was stirred at 0° C. for 2 h. The reaction was concentrated and dried under vacuum to afford the title compound, which was used in the next step without purification.

Step E: 3-(4-chlorophenyl)-6-methyl-1,3-dihydrofuro[3,4-c]pyridin-7-yl(1s,3R,4S)-3,4-bis(nitrooxy)cyclopentanecarboxylate A solution of (1R,2S,4s)-4-(chlorocarbonyl)cyclopentane-1,2-diyl dinitrate (40 mmol) from Step D in 150 mL dichloromethane was cooled to 0° C. To this was added 3-(4-chlorophenyl)-6-methyl-1,3-dihydrofuro[3,4-c]pyridin-7-ol (9.63 g, 36.8 mmol) and pyridine (3.88 ml, 48.0 mmol) and the cloudy mixture was stirred at rt for 6 hrs. The reaction mixture was partitioned between 200 mL of water and 200 mL of dichloromethane. The layers were separated and the combined organic layers were washed with 200 mL water, 200 mL brine, dried over Na2SO4, filtered and concentrated. The residue was purified by silica gel chromatography using a 5-15% acetone-hexane to afford the title compound; $^1$H NMR (500 MHz, CDCl$_3$) δ 2.48 (s, 3H), 2.5-2.53 (m, 2H), 2.56-2.62 (m, 2H), 3.55 (m, 1H), 5.05 (dd, J=14 Hz, 3 Hz, 1H), 5.17 (dd, J=14 Hz, 3Hz, 1H), 5.67 (m, 2H), 6.24 (s, 1H), 7.29 (d, J=8 Hz, 2H), 7.38 (d, J=8 Hz, 2H), 8.12 (s, 1H); LC-MS: m/z 480 ($^{33}$Cl M+1), 482 ($^{37}$Cl M+1).

Example 9

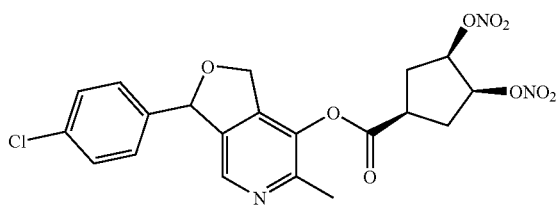

3-(4-chlorophenyl)-6-methyl-1,3-dihydrofuro[3,4-c]pyridin-7-yl(1r,3R,4S)-3,4-bis(nitrooxy)cyclopentanecarboxylate The title compound was prepared following the procedure for EXAMPLE 8, steps B-E, except that the reagent methyl (1s,3R,4S)-3,4-dihydroxycyclopentanecarboxylate was replaced by methyl (1r,3R,4S)-3,4-dihydroxycyclopentanecarboxylate (EXAMPLE 1, Step A); $^1$H NMR (500 MHz, CDCl$_3$) δ 2.56 (s, 3H), 2.57-2.62 (m, 2H), 2.64-2.71 (m, 2H), 3.35 (m, 1H), 5.11 (dd, J=14 Hz, 2.5 Hz, 1H), 5.23 (dd, J=14 Hz, 2.5 Hz, 1H), 5.56 (m, 2H), 6.25 (s, 1H), 7.29 (d, J=8 Hz, 2H), 7.38 (d, J=8 Hz, 2H), 8.14 (s, 1H); LC-MS: m/z 480 ($^{35}$Cl M+1), 482 ($^{37}$Cl M+1).

Example 10

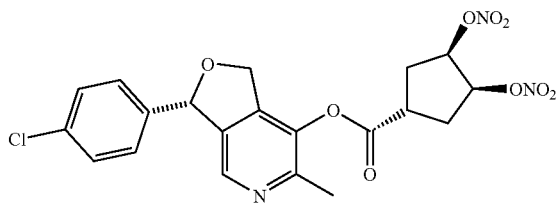

(3S)-3-(4-chlorophenyl)-6-methyl-1,3-dihydrofuro[3,4-c]pyridin-7-yl(1s,3R,4S)-3,4-bis(nitrooxy)cyclopentanecarboxylate The title compound was prepared following the procedure for EXAMPLE 8, step E, except that the reagent 3-(4-chlorophenyl)-6-methyl-1,3-dihydrofuro[3,4-c]pyridin-7-ol was replaced by (3S)-3-(4-chlorophenyl)-6-methyl-1,3-dihydrofuro[3,4-c]pyridin-7-ol; $^1$H NMR (500 MHz, CDCl$_3$) δ 2.48 (s, 3H), 2.5-2.53 (m, 2H), 2.56-2.62 (m, 2H), 3.55 (m, 1H), 5.05 (dd, J=14 Hz, 3 Hz, 1H), 5.17 (dd, J=14 Hz, 3 Hz, 1H), 5.67 (m, 2H), 6.24 (s, 1H), 7.29 (d, J=8 Hz, 2H), 7.38 (d, J=8 Hz, 2H), 8.12 (s, 1H); LC-MS: m/z 480 ($^{35}$Cl M+1), 482 ($^{37}$Cl M+1).

Example 11

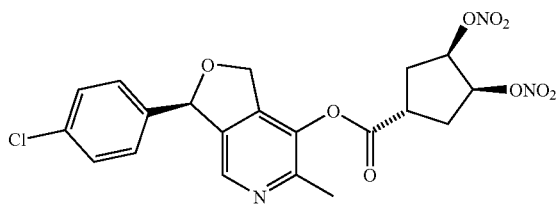

(3R)-3-(4-chlorophenyl)-6-methyl-1,3-dihydrofuro[3,4-c]pyridin-7-yl(1s,3R,4S)-3,4-bis(nitrooxy)cyclopentanecarboxylate The title compound was prepared following the procedure for EXAMPLE 8, step E, except that the reagent 3-(4-chlorophenyl)-6-methyl-1,3-dihydrofuro[3,4-c]pyridin-7-ol was replaced by (3R)-3-(4-chlorophenyl)-6-methyl-1,3-dihydrofuro[3,4-c]pyridin-7-ol; $^1$H NMR (500 MHz, CDCl$_3$) δ 2.48 (s, 3H), 2.5-2.53 (m, 2H), 2.56-2.62 (m, 2H), 3.55 (m, 1H), 5.05 (dd, J=14 Hz, 3 Hz, 1H), 5.17 (dd, J=14 Hz, 3 Hz, 1H), 5.67 (m, 2H), 6.24 (s, 1H), 7.29 (d, J=8 Hz, 2H), 7.38 (d, J=8 Hz, 2H), 8.12 (s, 1H); LC-MS: m/z 480 ($^{35}$Cl M+1), 482 ($^{37}$Cl M+1).

Example 12

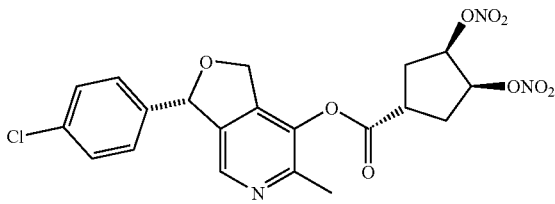

(3S)-3-(4-chlorophenyl-6-methyl-1,3-dihydrofuro[3,4-c]pyridin-7-yl(1s,3R,4S)-3,4-bis(nitrooxy)cyclopentanecarboxylate To a solution of (1s,3R,4S)-3,4-bis(nitrooxy)cyclopentanecarboxylic acid (476 mg, 2.014 mmol) and 4-N,N-dimethylaminopyridine (3 mg, 0.025 mmol) in acetonitrile (12 ml) and N,N'-dimethylformamide (2 mL) was added PyBOP (1384 mg, 2.66 mmol) and the mixture was stirred at rt for 5 min. To this was added (3R)-3-(4-chlorophenyl)-6-methyl-1,3-dihydrofuro[3,4-c]pyridin-7-ol (497 mg, 1.9 mmol) followed by triethylamine (0.397 ml, 2.85 mmol) in 1 mL acetonitrile. The reaction was stirred at rt for 1 h, until LC-MS indicated reaction was complete. The solution was concentrated under vacuum and the residue was dissolved in 20 ml dichloromethane and 10 ml water. An additional 20 mL of ether was added and the layers were separated. The organic layer was washed with two 10 mL portions of water and a 10 mL portion of brine, then was dried over Na$_2$SO$_4$, filtered through a pad of silica gel and concentrated. The residue was purified by HPLC on a 50 g Biotage SNAP silica gel column using a linear gradient of hexane-methyl t-butyl ether-acetonitrile and hexane, 20% to 80%, to afford the title compound; $^1$H NMR (500 MHz, CDCl$_3$) δ 2.48 (s, 3H), 2.5-2.53 (m, 2H), 2.56-2.62 (m, 2H), 3.55 (m, 1H), 5.05 (dd, J=14 Hz, 3 Hz, 1H), 5.17 (dd, J=14 Hz, 3 Hz, 1H), 5.67 (m, 2H), 6.24 (s, 1H), 7.29 (d, J=8 Hz, 2H), 7.38 (d, J=8 Hz, 2H), 8.12 (s, 1H), LC-MS: m/z 480 ($^{35}$Cl M+1), 482 ($^{37}$Cl M+1)

Examples 13-27

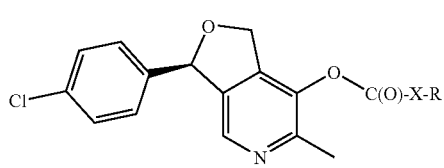

The following EXAMPLES 13-27 were prepared using the procedures described in EXAMPLES 8 and 12:

| EXAMPLE | Name | —C(O)—X—R | Mass Spectrum m/e |
|---|---|---|---|
| 13 | 3-(4-chlorophenyl)-6-methyl-1,3-dihydrofuro[3,4-c]pyridin-7-yl 2,2-dimethyl-3-(nitrooxy-)propanoate | | 407 (M + 1, $^{35}$Cl); 409 (M + 1, $^{37}$Cl) |
| 14 | 3-(4-chlorophenyl)-6-methyl-1,3-dihydrofuro[3,4-c]pyridin-7-yl 2-methyl-4-(nitrooxy-butanoate | | 407 (M + 1, $^{35}$Cl); 409 (M + 1, $^{37}$Cl) |
| 15 | 3-(4-chlorophenyl)-6-methyl-1,3-dihydrofuro[3,4-c]pyridin-7-yl 2-methyl-3-(nitrooxy)-2-[(nitrooxy)methyl]propanoate | | 468 (M + 1, $^{35}$Cl); 470 (M + 1, $^{37}$Cl) |
| 16 | 3-(4-chlorophenyl)-6-methyl-1,3-dihydrofuro[3,4-c]pyridin-7-yl 3-(nitrooxy)cyclopentane-carboxylate | | 419 (M + 1, $^{35}$Cl); 421 (M + 1, $^{37}$Cl) |
| 17 | 3-(4-chlorophenyl)-6-methyl-1,3-dihydrofuro[3,4-c]pyridin-7-yl 2,2-dimethyl-5-(nitrooxy)-pentanoate | | 435 (M + 1, $^{35}$Cl); 437 (M + 1, $^{37}$Cl) |
| 18 | 3-(4-chlorophenyl)-6-methyl-1,3-dihydrofuro[3,4-c]pyridin-7-yl 4-(nitrooxy)pentanoate | | 407 (M + 1, $^{35}$Cl); 409 (M + 1, $^{37}$Cl) |
| 19 | 3-(4-chlorophenyl)-6-methyl-1,3-dihydrofuro[3,4-c]pyridin-7-yl [(1s,3R,4S)-3,4-bis(nitrooxy)-cyclopentyl]acetate | | 494 (M + 1, $^{35}$Cl); 496 (M + 1, $^{37}$Cl) |
| 20 | 3-(4-chlorophenyl)-6-methyl-1,3-dihydrofuro[3,4-c]pyridin-7-yl cis-4-(nitrooxy)cyclohexane-carboxylate | | 433 (M + 1, $^{35}$Cl); 435 (M + 1, $^{37}$Cl) |
| 21 | 3-(4-chlorophenyl)-6-methyl-1,3-dihydrofuro[3,4-c]pyridin-7-yl 2,2-dimethyl-5-(nitrooxy)-pentanoate | | 435 (M + 1, $^{35}$Cl); 437 (M + 1, $^{37}$Cl) |
| 22 | 3-(4-chlorophenyl)-6-methyl-1,3-dihydrofuro[3,4-c]pyridin-7-yl (3R,4R)-3,4-bis(nitrooxy)-cyclopentanecarboxylate | | 480 (M + 1, $^{35}$Cl); 482 (M + 1, $^{37}$Cl) |

| EXAMPLE | Name | —C(O)—X—R | Mass Spectrum m/e |
|---|---|---|---|
| 23 | (3S)-3-(4-chlorophenyl)-6-methyl-1,3-dihydrofuro[3,4-c]pyridin-7-yl (4R,5R)-4,5-bis(nitrooxy)hexanoate | | 482 (M + 1, ³⁵Cl); 484 (M + 1, ³⁷Cl) |
| 24 | 3-(4-chlorophenyl)-6-methyl-1,3-dihydrofuro[3,4-c]pyridin-7-yl cis-3-(nitrooxy)cyclobutanecarboxylate | | 405 (M + 1, ³⁵Cl); 407 (M + 1, ³⁷Cl) |
| 25 | 3-(4-chlorophenyl)-6-methyl-1,3-dihydrofuro[3,4-c]pyridin-7-yl trans-3-(nitrooxy)cyclobutanecarboxylate | | 405 (M + 1, ³⁵Cl); 407 (M + 1, ³⁷Cl) |
| 26 | (3S)-3-(4-chlorophenyl)-6-methyl-1,3-dihydrofuro[3,4-c]pyridin-7-yl (1r,2R,3S)-2,3-bis(nitrooxy)methyl]cyclopropanecarboxylate | | 480 (M + 1, ³⁵Cl); 482 (M + 1, ³⁷Cl) |

Example 27

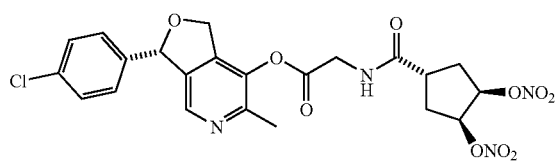

(3S)-3-(4-chlorophenyl)-6-methyl-1,3-dihydrofuro[3,4-c]pyridin-7-yl N-{[(1s,3R,4S)-3,4-bis(nitrooxy)cyclopentyl]carbonyl}glycinate

Step A: Ethyl N-{[(1s,3R,4S)-3,4-bis(nitrooxy)cyclopentyl]carbonyl}glycinate To a solution of (1s,3R,4S)-3,4-bis(nitrooxy)cyclopentanecarboxylic acid (1.889 g, 8 mmol) in 25 mL dichloromethane was added N-ethyl-N-(1,1-dimethylamino)propylcarbodiimide hydrochloride (2.454 g, 12.80 mmol). After 15 minutes glycine ethyl ester hydrochloride (1.340 g, 9.60 mmol) and pyridine (0.78 mL (9.60 mmole) were added and the solution was stirred at rt. After 2 h, the solution was diluted with 100 mL ether and 50 mL water and the layers were separated. The aqueous layer was washed with 50 mL ethyl acetate and the combined organic layers were washed with brine, dried over Na2SO4, filtered through a pad of silica gel and concentrated. The residue was purified by chromatography on a Biotage SNAP-50 cartridge using a linear gradient of (3:6:1 hexane-methyl tert-butyl ether-acetonitrile):hexane, 20% to 50%, to give the title compound: ¹H NMR (500 MHz, CDCl₃) δ 1.33 (t, J=7 Hz, 3H), 2.2-2.25 (m, 2H), 2.42-2.48 (m, 2H), 2.58 (s, br, 2H), 3.03 (m, 1H), 3.50 (s, 3H), 4.06 (d, J=6 Hz, 2H) 4.26 (q, J=7 Hz, 2H), 5.65 (m, 2H), 6.05 (t, br, J=6 Hz, 1H); LC-MS: m/z 322.

Step B: N-{[(1s,3R,4S)-3,4-bis(nitrooxy)cyclopentyl]carbonyl}glycine

A solution of 2.0 g (6.23 mmole) of ethyl N-{[(1s,3R,4S)-3,4-bis(nitrooxy)cyclopentyl]carbonyl}glycinate in 10 mL methanol was cooled to 0° C. in an ice bath. To this was added 3.27 mL of 4M KOH solution and the solution was stirred at 0° C. for 2 h, then warmed to rt over 30 min. The solution was acidified to pH 7 with 6M HCl and then the methanol was removed under vacuum. The aqueous solution was acidified to pH 3 with 6M HCl and title compound was collected by filtration; LC-MS: m/z 322.

Step C: (3S)-3-(4-chlorophenyl)-6-methyl-1,3-dihydrofuro[3,4-c]pyridin-7-yl N-{[(1s,3R,4S)-3,4-bis(nitrooxy)cyclopentyl]carbonyl}glycinate To a solution of N-{[(1s,3R,4S)-3,4-bis(nitrooxy)cyclopentyl]carbonyl}glycine (5.88 mg, 2.67 mmol) and 4-N,N-dimethylaminopyridine (7 mg, 0.057 mmol) in acetonitrile (12 ml) and N,N'-dimethylformamide (2 mL) was added PyBOP (1392 mg, 2.67 mmol) and the mixture was stirred at rt for 5 min. To this was added (3R)-3-(4-chlorophenyl)-6-methyl-1,3-dihydrofuro[3,4-c]pyridin-7-ol (500 mg, 1.91 mmol) followed by triethylamine (0.399 ml, 2.85 mmol) in 1 mL acetonitrile. The reaction was stirred at rt for 1 h, until LC-MS indicated reaction was complete. The solution was diluted with water and the solid product was collected by filtration. The solid was washed with 80% acetonitrile-ether and air-dried to afford the title compound; $^1$H NMR (500 MHz, acetone-d6) δ 2.2-2.25 (m, 2H), 2.41 (s, 3H), 2.48-2.56 (m, 2H), 3.3 (m, 1H), 4.3 (d, J=6 Hz, 2H), 5.04 (dd, J=14 Hz, 1.5 Hz, 1H), 5.21 (dd, J=14 Hz, 3 Hz, 1H), 5.8 (m, 2H), 6.32 (s, 1H), 7.44 (dd, J=7 Hz, J=3 Hz, 4H), 8.03 (t, br, J=6 Hz, 1H), 8.13 (s, 1H); LC-MS: m/z 537 ($^{35}$Cl M+1), 539 ($^{37}$Cl M+1)

Examples 28-30

The following EXAMPLES 28-30 were prepared as described in EXAMPLE 27 except that esters of L-alanine, L-leucine or L-phenylalanine were used instead of glycine ethyl ester hydrochloride:

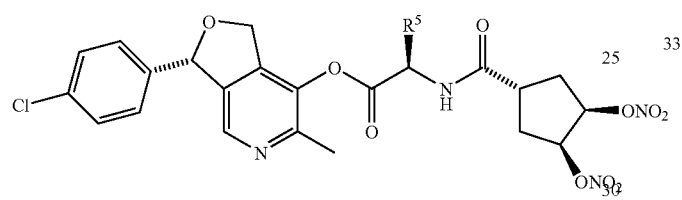

| EX-AMPLE | Name | R$^5$ | Mass Spectrum m/e |
|---|---|---|---|
| 28 | (3S)-3-(4-chlorophenyl)-6-methyl-1,3-dihydrofuro[3,4-c]pyridin-7-yl N-{[(1s,3R,4S)-3,4-bis(nitrooxy)cyclopentyl]-carbonyl}-D-alaninate | —CH$_3$ | 480 (M + 1, $^{35}$Cl); 482 (M + 1, $^{37}$Cl) |
| 29 | (3S)-3-(4-chlorophenyl)-6-methyl-1,3-dihydrofuro[3,4-c]pyridin-7-yl N-{[(1s,3R,4S)-3,4-bis(nitrooxy)cyclopentyl]-carbonyl}-D-leucinate |  | 593 (M + 1, $^{35}$Cl); 595 (M + 1, $^{37}$Cl) |
| 30 | (3S)-3-(4-chlorophenyl)-6-methyl-1,3-dihydrofuro[3,4-c]pyridin-7-yl N-{[(1s,3R,4S)-3,4-bis(nitrooxy)cyclopentyl]-carbonyl}-D-phenylalaninate |  | 627 (M + 1, $^{35}$Cl); 629 (M + 1, $^{37}$Cl) |

Examples 31-34

The following EXAMPLES were prepared using procedures analogous to those described for EXAMPLE 27 substituting appropriate acids for (1s,3R,4S)-3,4-bis(nitrooxy)cyclopentanecarboxylic acid in Step A.

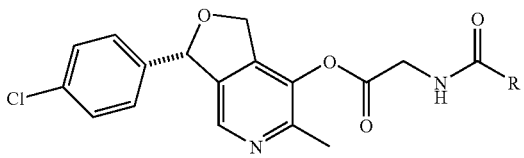

| EX-AMPLE | R | HPLC R$_1$ (min) | MS (M + H) |
|---|---|---|---|
| 31 | 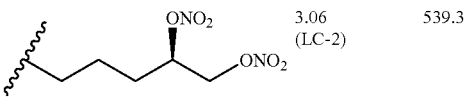 | 3.12 (LC-2) | 539.3 |
| 32 | 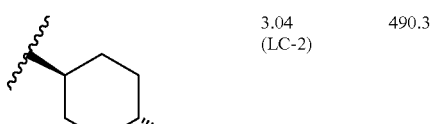 | 3.06 (LC-2) | 539.3 |
| 33 | 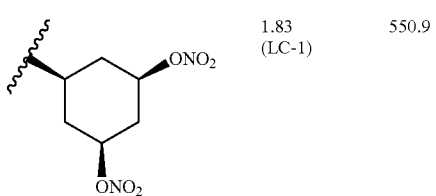 | 3.04 (LC-2) | 490.3 |
| 34 |  | 1.83 (LC-1) | 550.9 |

Examples 35-36

The following EXAMPLES were prepared using procedures analogous to those described for EXAMPLE 27 substituting appropriate acid and sarcosine ethyl ester hydrochloride for (1s,3R,4S)-3,4-bis(nitrooxy)cyclopentanecarboxylic acid and glycine ethyl ester hydrochloride, respectively, in Step A.

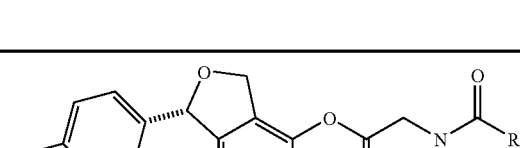

| EX-AMPLE | R | HPLC R$_1$ (min) | MS (M + H) |
|---|---|---|---|
| 35 | 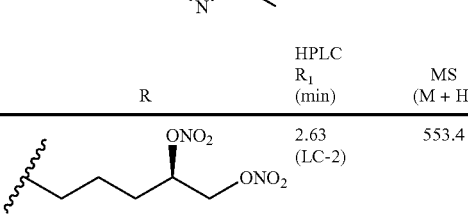 | 2.63 (LC-2) | 553.4 |

-continued

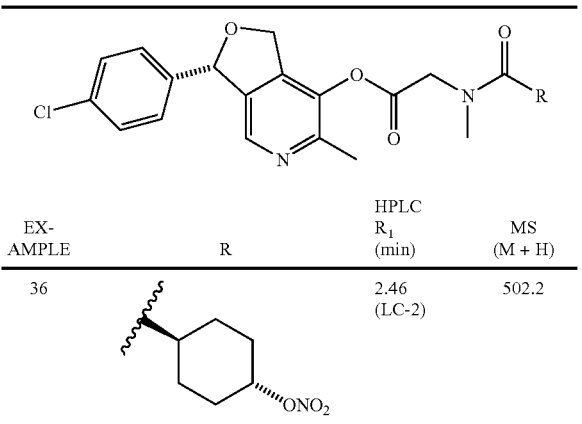

| EXAMPLE | R | HPLC R₁ (min) | MS (M + H) |
|---|---|---|---|
| 36 | 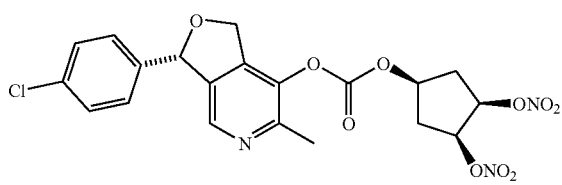 | 2.46 (LC-2) | 502.2 |

Example 37

(1r,3R,4S)-3,4-Bis(nitrooxy)cyclopentyl (3S)-3-(4-chlorophenyl)-6-methyl-1,3-dihydrofuro[3,4-c]pyridin-7-yl carbonate To a solution of (+)-cicletanine (1.4 g, 5.35 mmol) in DMF (20 mL) at 0° C. was added NaH (60 wt %, 0.32 g, 8.02 mmol). After 20 min at 0° C., (1r,3R,4S)-3,4-bis(nitrooxy)-cyclopentyl 1-chloroethyl carbonate (2.02 g, 6.42 mmol) was added. The mixture was allowed to warm up to rt and stirred over night. The mixture was then partitioned between EtOAc and H₂O. The organic layer was washed with brine, dried over MgSO₄ and concentrated. The residue was purified by flash chromatography (Biotage SP1; column 40M; TLC method: n-hexane/ethyl acetate 5/5; $R_f$=0.35), affording the title product (1.71 g, yield 64%). ¹H NMR (500 MHz, CDCl₃) δ 8.08 (s, 1H), 7.36-7.26 (m, 4H), 6.20 (s, 1H), 5.50 (m, 2H), 5.23-5.10 (m, 2H), 2.73-2.68 (m, 2H), 2.50 (s, 3H), 2.34-2.04 (m, 2H); LC-MS: m/z 496.3 (M+H). (t=3.39).

Examples 38-46

The following EXAMPLES were prepared using procedures analogous to those described for EXAMPLE 37 substituting appropriate acids for (1s,3R,4S)-3,4-bis(nitrooxy)cyclopentanecarboxylic acid in Step A.

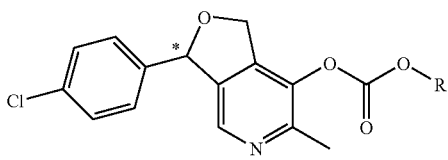

| EXAMPLE | Chirality | R | HPLC R₁ (min) | MS (M + H) |
|---|---|---|---|---|
| 38 | S | 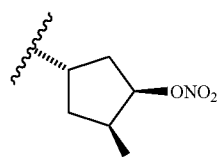 | 3.39 (LC-2) | 496.3 |
| 39 | S | 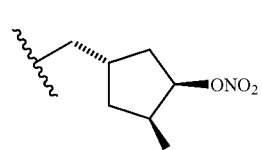 | 3.50 (LC-2) | 510.2 |
| 40 | S | 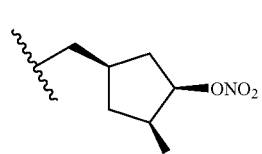 | 3.47 (LC-2) | 510.2 |

-continued
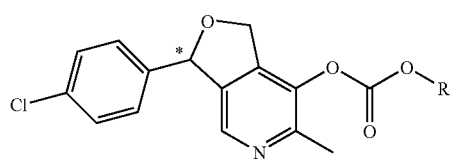
| EXAMPLE | Chirality | R | HPLC R₁ (min) | MS (M + H) |
|---|---|---|---|---|
| 41 | R | 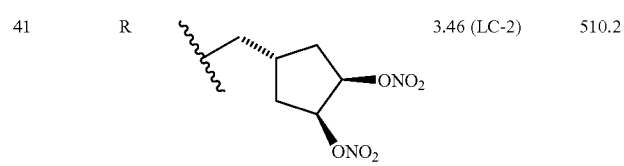 | 3.46 (LC-2) | 510.2 |
| 42 | R | 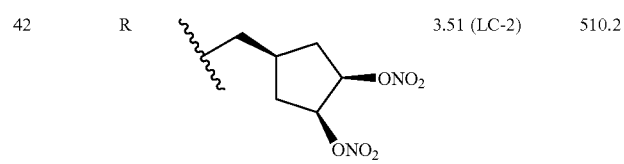 | 3.51 (LC-2) | 510.2 |
| 43 | S | 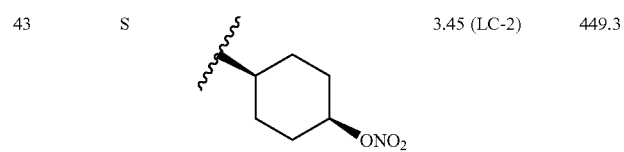 | 3.45 (LC-2) | 449.3 |
| 44 | racemic | 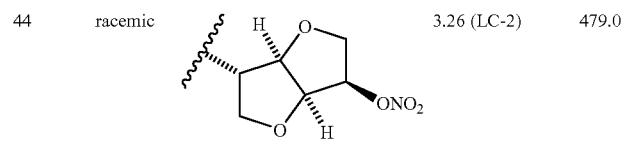 | 3.26 (LC-2) | 479.0 |
| 45 | R | 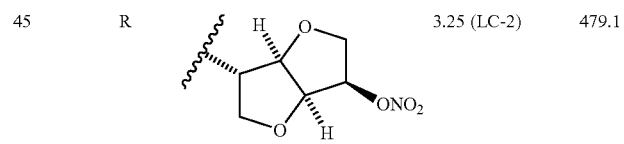 | 3.25 (LC-2) | 479.1 |
| 46 | S | 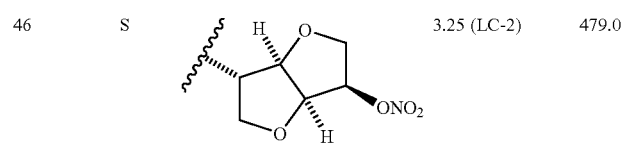 | 3.25 (LC-2) | 479.0 |

Example 47

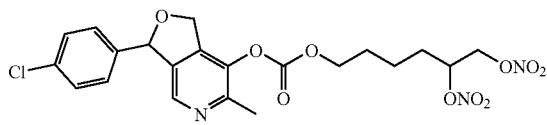

5,6-Bis(nitrooxy)hexyl 3-(4-chlorophenyl)-6-methyl-1,3-dihydrofuro[3,4-c]pyridin-7-yl carbonate

Step A: 5,6-Bis(nitrooxy)hexyl 4-nitrophenyl carbonate

To the solution of 6-hydroxyhexane-1,2-diyl dinitrate (150 mg, 0.67 mmol) in CH$_2$Cl$_2$ (15 mL) at rt was added 4-nitrophenyl chloroformate (202 mg, 1.00 mmol) and followed by pyridine (159 mg, 2.01 mmol). The mixture was stirred at rt over night and diluted with H$_2$O. The mixture was extracted with CH$_2$Cl$_2$ and the organic layer was washed with brine, dried over MgSO$_4$ and concentrated. The residue was purified by flash chromatography (Biotage SP1; column 25M; TLC method: n-hexane/ethyl acetate 7/3; R$_f$=0.35), affording product (210 mg, yield 81%).

Step B: 5,6-bis(nitrooxy)hexyl 3-(4-chlorophenyl)-6-methyl-1,3-dihydrofuro[3,4-c]pyridin-7-yl carbonate To a solution of cicletanine (120 mg, 0.55 mmol) in DMF (10 mL) was added Cs$_2$CO$_3$ (373 mg, 1.15 mmol) and followed by 5,6-bis(nitrooxy)hexyl 4-nitrophenyl carbonate (210 mg, 0.54 mmol). The mixture was stirred at rt over night and diluted with H$_2$O, extracted with CH$_2$Cl$_2$ and the organic layer was washed with brine, dried over MgSO$_4$ and concentrated. The residue was purified by flash chromatography (Biotage SP1; column 25M; TLC method: n-hexane/ethyl acetate 5/5; R$_f$=0.35), affording product. $^1$H NMR (500 MHz, CDCl$_3$) δ 8.08 (s, 1H), 7.36-7.27 (m, 4H), 6.21 (s, 1H), 5.34 (m, 1H), 5.26 (m, 1H), 5.13 (m, 1H), 4.77 (m, 1H), 4.48 (m, 1H), 4.32 (m, 2H), 2.51 (s, 3H), 1.84 (m, 4H), 1.69-1.55 (m, 2H).

Example 48

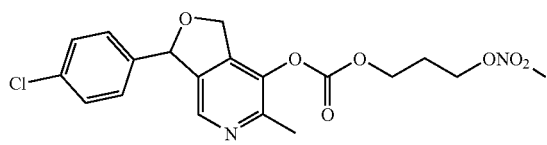

3-(4-Chlorophenyl)-6-methyl-1,3-dihydrofuro[3,4-c]pyridin-7-yl 3-(nitrooxy)propyl carbonate To a solution of 3-hydroxypropyl nitrate (100 mg, 0.83 mmol) in THF (10 mL) at 0° C. was added phosgene (20% in toluene, 425 mg, 0.86 mmol). After stirring at 0° C. for 45 min, the mixture was allowed to warm to rt. After stirring at rt for 2 hr, the mixture was concentrated. The residue was dissolved in 10 mL CH$_2$Cl$_2$, which was added to a suspension of cicletanine (150 mg, 0.57 mmol) and diisopropylethylamine (185 mg, 1.43 mmol). After stirring at rt over night, the mixture was diluted with H$_2$O and extracted with CH$_2$Cl$_2$. The organic layer was washed with brine, dried over MgSO$_4$ and concentrated. The residue was purified by flash chromatography (Biotage SP1; column 25M; TLC method: n-hexane/ethyl acetate 7/3; R$_f$=0.35), affording the title product. $^1$H NMR (500 MHz, CDCl$_3$) δ 8.37 (s, 1H), 7.40-7.28 (m, 4H), 6.29 (s, 1H), 5.42-5.25 (m, 2H), 4.66 (m, 2H), 4.49 (m, 2H), 2.71 (s, 3H), 2.28-2.23 (m, 2H).

Example 49

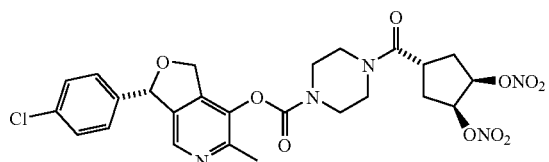

(3S)-3-(4-Chlorophenyl)-6-methyl-1,3-dihydrofuro[3,4-c]pyridine-7-yl 4-{[(1s,3R,4S)-3,4-bis(nitrooxy)cyclopentyl]carbonyl}piperazine-1-carboxylate

Step A: tert-Butyl 4-{[(1s,3R,4S)-3,4-bis(nitrooxy)cyclopentyl]carbonyl}piperazine-1-carboxylate To a solution of (1s,3R,4S)-3,4-bis(nitrooxy)cyclopentanecarboxylic acid (103.2 mg, 0.44 mmol), tert-butyl piperazine-1-carboxylate (81 mg, 0.44 mmol), and Et$_3$N (122 µL, 0.87 mmol) in CH$_2$Cl$_2$ (20 mL) at rt was added PyBOP (341 mg, 0.66 mmol). After stirring for 3 hr, the reaction mixture was purified by flash chromatography (Biotage 40+S; hexane/EtOAc 7/3), affording the title product (167 mg, yield 94%). $^1$H NMR (500 MHz, CDCl$_3$) δ 5.62 (m, 2H), 3.62-3.60 (m, 2H), 3.47-3.34 (m, 7H), 2.45-2.41 (m, 2H), 2.22-2.16 (m, 2H), 1.48 (s, 9H).

Step B: (1R,2S,4s)-4-(Piperazin-1-ylcarbonyl)cyclopenatane-1,2-diyl dinitrate To a solution of tert-butyl 4-{[(1s,3R,4S)-3,4-bis(nitrooxy)cyclopentyl]-carbonyl}piperazine-1-carboxylate (167 mg, 0.42 mmol) in CH$_2$Cl$_2$ (5 mL) at rt was added trifluoroacelic acid (1.0 mL, 13.0 mmol). After stirring for 3 hr, the reaction mixture was concentrated, affording the title product (90 mg, yield 71%). $^1$H NMR (500 MHz, CDCl$_3$) δ 5.63-5.60 (m, 2H), 3.62-3.60 (m, 2H), 3.47-3.44 (m, 2H), 3.37-3.32 (m, 1H), 2.89-2.84 (m, 4H), 2.47-2.41 (m, 2H), 2.20-2.14 (m, 2H).

Step C: (1R,2S,4s)-4-{[4-(4-Nitrobenzoyl)piperazin-1-yl]carbonyl}cyclopenatane-1,2-diyl dinitrate To a solution of (1R,2S,4s)-4-(piperazin-1-ylcarbonyl)cyclopenatane-1,2-diyl dinitrate (90 mg, 0.30 mmol) and Et$_3$N (41 µL, 0.30 mmol) in Et$_2$O (10 mL) at 0° C. was added 4-nitrophenyl chloroformate (1.0 mL, 13.0 mmol). The mixture was allowed to warm up to rt and stirred for overnight.

The reaction mixture was diluted with Et$_2$O (20 mL) and washed with brine (3×50 mL), dried over MgSO$_4$, and concentrated. The residue was purified by flash chromatography (Biotage 40+S; hexane/EtOAc 6/4), affording the title product (51 mg, yield 37%). $^1$H NMR (500 MHz, CDCl$_3$) δ 8.27 (d, J=9.2, 2H), 7.31 (d, J=9.2, 2H), 5.65-5.62 (m, 2H), 3.74-3.61 (m, 8H), 3.43-3.38 (m, 1H), 2.49-2.44 (m, 2H), 2.25-2.19 (m, 2H).

Step D: (3S)-3-(4-Chlorophenyl)-6-methyl-1,3-dihydrofuro[3,4-c]pyridine-7-yl 4-{[(1s,3R,4S)-3,4-bis(nitrooxy)cyclopentyl]carbonyl}piperazine-1-carboxylate To a suspension of (+)-cicletanine (28.4 mg, 0.11 mmol) and (1R,2S,4s)-4-{[4-(4-nitrobenzoyl)piperazin-1-yl]carbonyl}cyclopenatane-1,2-diyl dinitrate (51 mg, 0.11 mmol) in DMF (5 mL) at rt was added Cs$_2$CO$_3$ (70.8 mg, 0.22 mmol). After stirring for overnight, the mixture was diluted with Et$_2$O (20 mL) and washed with brine (3×50 mL), dried over MgSO$_4$, and concentrated. The residue was purified by preparative thin layer chromatography (hexane/EtOAc 4/6), affording the title product. $^1$H NMR (500 MHz, CDCl$_3$) δ 8.05 (s, 1H), 7.34 (d, J=8.5, 2H), 7.26 (d, J=8.5, 2H), 6.20 (s, 1H), 5.64-5.62 (m, 2H), 5.22 (dd, J=2.3, 13.7, 1H), 5.11 (dd, J=1.6, 13.7, 1H), 3.75-3.40 (m, 8H), 3.40 (m, 1H), 2.47-2.44 (m, 5H), 2.25-2.19 (m, 2H); LC-MS: m/z 592.26 (M+H), R$_t$=1.94 min.

Example 50

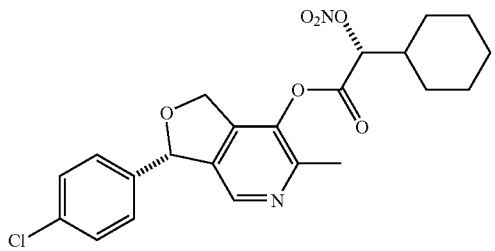

(R)—((S)-3-(4-chlorophenyl)-6-methyl-1,3-dihydrofuro[3,4-c]pyridin-7-yl)2-cyclohexyl-2-(nitrooxy)acetate INTERMEDIATE 17 (660 mg, 3.25 mmol) was dissolved in CH$_2$Cl$_2$ (5 mL). To the solution cooled to 0° C. (COCl)$_2$ (1.12 mL, 12.8 mmol) and few drops of DMF were added. The reaction was stirred at 0° C. for 1-2 hours, then the volatiles were removed and the mixture was taken up twice with CH$_2$Cl$_2$. The residue was dissolved in CH$_2$Cl$_2$ (30 mL). To the solution, cooled to 0° C., (+)-cicletanine (837 mg, 3.2 mmol) and pyridine (387 μL, 4.8 mmol) were added. The reaction was stirred overnight at room temperature, quenched with brine, dried over Na$_2$SO$_4$ and concentrated. The crude material was purified by SP1 BIOTAGE (eluting with EtOAc/Hexane from 10 to 40%) affording the title compound as a white solid.

$^1$H-NMR (CDCl$_3$): 8.11 (1H, s); 7.32 (4H, m); 6.23 (1H, s); 5.26 (1H, d, J=4.7 Hz); 5.11 (2H, m); 2.49 (3H, s); 2.19 (1H, m); 1.87 (5H, m); 1.36 (5H, m)

Example 51

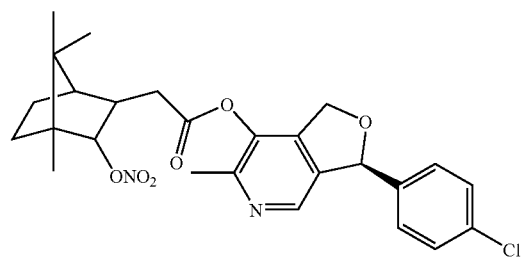

(S)-3-(4-chlorophenyl-6-methyl-1,3-dihydrofuro[3,4-c]pyridin-7-yl 2-(4,7,7-trimethyl-3-(nitrooxy)bicyclo[2.2.1]heptan-2-yl)acetate Title compound was prepared by following the same procedure given for EXAMPLE 50 using INTERMEDIATE 18 as a starting material.

$^1$H-NMR (DMSO): 8.12 (1H, s); 7.43 (4H, m); 6.34 (1H, s); 5.11 (2H, m); 4.83 (1H, d, J=4 Hz); 3.17 (1H, m); 2.86 (1H, m); 2.76 (1H, m); 2.35 (3H, s); 1.85 (1H, m); 1.62 (2H, m); 1.41 (2H, m); 0.98 (3H, s); 0.87 (3H, s); 0.85 (3H, s)

Example 52

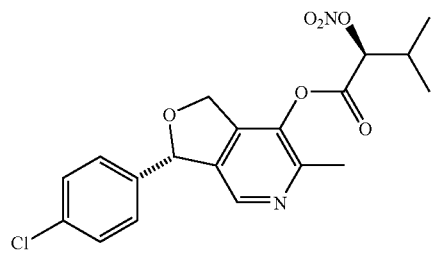

(S)—((S)-3-(4-chlorophenyl)-6-methyl-1,3-dihydrofuro[3,4-c]pyridin-7-yl)3-methyl-2-(nitrooxy)butanoate Title compound was prepared by following the same procedure given for EXAMPLE 50 using INTERMEDIATE 19 as a starting material.

$^1$H-NMR (CDCl$_3$): 8.11 (1H, s); 7.32 (4H, m); 6.22 (1H, s); 5.27 (1H, d, J=4.5 Hz); 5.11 (2H, m); 2.55 (1H, m); 2.49 (3H, s); 1.26 (3H, d, J=6.9 Hz); 1.20 (3H, d, J=6.9 Hz)

Example 53

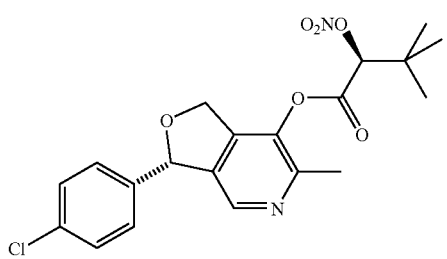

(S)—((S)-3-(4-chlorophenyl-6-methyl-1,3-dihydro-furo[3,4-c]pyridin-7-yl)3,3-dimethyl-2-(nitrooxy)butanoate Title compound was prepared by following the same procedure given for EXAMPLE 50 using INTERMEDIATE 20 as a starting material.

$^1$H-NMR (CDCl$_3$): 8.11 (1H, s); 7.33 (4H, m); 6.22 (1H, s); 5.10 (3H, s+m); 2.51 (3H, s); 1.26 (9H, s)

Example 54

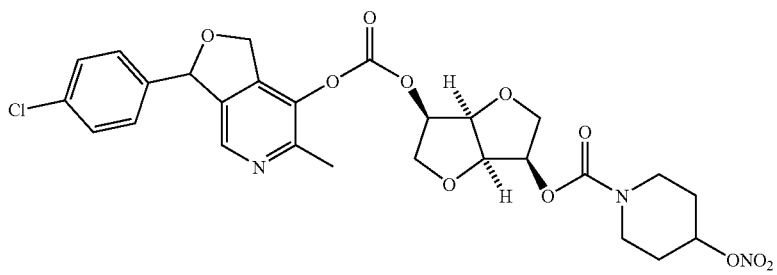

(3R,3aR,6R,6aR)-6-((3-(4-chlorophenyl-6-methyl-1,3-dihydrofuro[3,4-c]pyridin-7-yloxy)carbonyloxy)hexahydrofuro[3,2-b]furan-3-yl 4-(nitrooxy)piperidine-1-carboxylate To a solution of cicletanine (0.25 g, 0.97 mmol) and INTERMEDIATE 1.3 (0.47 g, 0.97 mmol) in DME (15 mL), was added DMAP (0.18 g, 1.46 mmol) as solid. After stirring at rt over night, the mixture was diluted with EtOAc and washed with NaH$_2$PO$_4$ 5%. The organic layer was dried over Na$_2$SO$_4$ and concentrated. The residue was purified by flash chromatography (Biotage SP1; column SNAP 50; 2% MeOH in CH$_2$Cl$_2$), affording the title product as a white solid.

$^1$H-NMR (300 MHz, DMSO-d$_6$); δ 8.12 (1H, s); 7.48-7.42 (4H, m); 6.35 (1H, s); 5.81-5.05 (4H, m); 5.0-4.9 (1H, m); 4.85-4.79 (1H, m); 4.6-4.52 (1H, m); 4.15-4.05 (1H, m); 4.09-4.9 (2H, m); 3.72-3.62 (3H, m); 3.4-3.2 (2H, m), 2.40 (3H, s); 2.05-1.92 (2H, m); 1.7-1.57 (2H, m).

Example 55

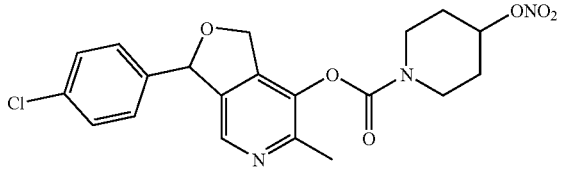

4-Nitrooxy-piperidine-1-carboxylic acid 3-(4-chlorophenyl)-6-methyl-1,3-dihydro-furo[3,4-c]pyridin-7-yl ester The title compound was prepared following the procedure for EXAMPLE 54, except that the reagent INTERMEDIATE 13 was replaced by INTERMEDIATE 14. $^1$H-NMR (300 MHz, CDCl$_3$); δ 8.06 (1H, s); 7.40-7.27 (4H, m); 6.22 (1H, s); 5.30-5.08 (3H, m); 4.05-3.50 (4H, m); 2.49 (3H, s); 2.20-2.08 (2H, m); 2.01-1.86 (2H, m).

Example 56

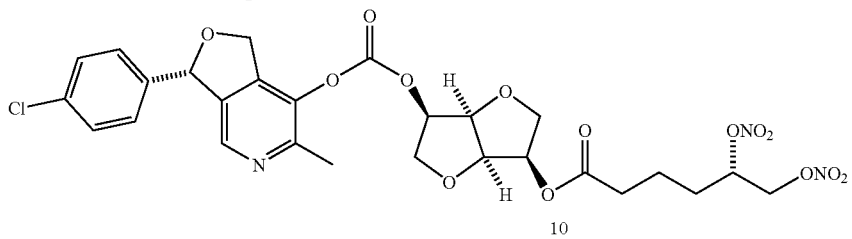

(S)-((3R,3aR,6R,6aR)-6-(((S)-3-(4-chlorophenyl)-6-methyl-1,3-dihydrofuro[3,4-c]pyridin-7-yloxy)carbonyloxy)hexahydrofuro[3,2-b]furan-3-yl)5,6-bis(nitrooxy)hexanoate The title compound was prepared following the procedure for EXAMPLE 54, except that the reagent INTERMEDIATE 13 was replaced by INTERMEDIATE 15 and the reagent cicletanine was replaced by (+)-cicletanine. $^1$H-NMR (300 MHz, CDCl$_3$); δ 8.11 (1H, s); 7.40-7.27 (4H, m); 6.22 (1H, s); 5.40-5.26 (2H, m); 5.20-5.17 (3H, m); 5.92-5.20 (3H, m); 4.59-4.46 (1H, m); 4.21-4.01 (3H, m); 3.95-3.85 (1H, m); 2.60-2.44 (5H, m); 1.93-1.78 (4H, m).

Example 57

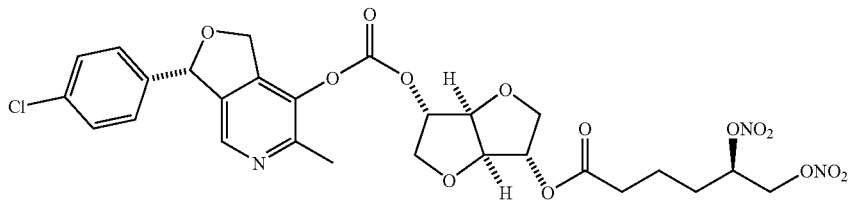

(R)-((3S,3aR,6S,6aR)-6-(((S)-3-(4-chlorophenyl)-6-methyl-1,3-dihydrofuro[3,4-c]pyridin-7-yloxy)carbonyloxy)hexahydrofuro[3,2-b]furan-3-yl)5,6-bis(nitrooxy)hexanoate The title compound was prepared following the procedure for EXAMPLE 54, except that the reagent INTERMEDIATE 13 was replaced by INTERMEDIATE 16 and the reagent cicletanine was replaced by (+)-cicletanine. $^1$H-NMR (300 MHz, CDCl$_3$); δ 8.10 (1H, s); 7.40-7.27 (4H, m); 6.22 (1H, s); 5.35-5.10 (4H, m); 4.81-4.74 (3H, m); 4.57-4.46 (1H, m); 4.15-3.92 (4H, m); 2.52 (3H, s); 2.50-2.40 (2H, m); 1.90-1.78 (4H, m).

Example 58

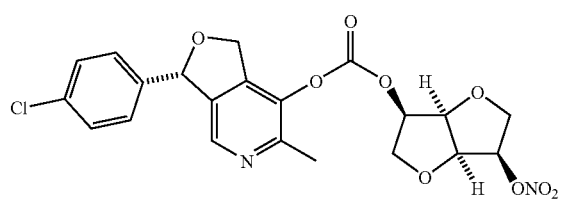

(S)-3-(4-chlorophenyl)-6-methyl-1,3-dihydrofuro[3,4-c]pyridin-7-yl(3R,3aR,6R,6aS)-6-(nitrooxy)hexahydrofuro[3,2-b]furan-3-yl carbonate The title compound was prepared following the procedure for EXAMPLE 54, except that the reagent INTERMEDIATE 13 was replaced by INTERMEDIATE 21 and the reagent cicletanine was replaced by (+)-cicletanine. $^1$H-NMR (300 MHz, DMSO-d$_6$): δ 8.17 (1H, s); 7.5-7.39 (4H, m); 6.35 (1H, s); 5.55-5.45 (1H, m); 5.3-5.05 (3H, m); 4.87-4.79 (2H, m); 4.18-4.05 (2H, m); 3.93-3.85 (2H, m); 2.40 (3H, s).

Example 59

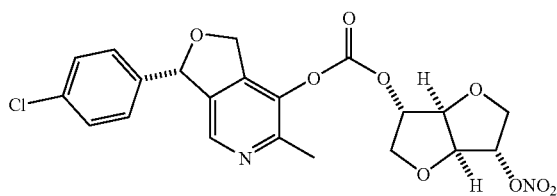

(S)-3-(4-chlorophenyl)-6-methyl-1,3-dihydrofuro[3,4-c]pyridin-7-yl(3S,3aR,6S,6aS)-6-(nitrooxy)hexahydrofuro[3,2-b]furan-3-yl carbonate The title compound was prepared following the procedure for EXAMPLE 54, except that the reagent INTERMEDIATE 13 was replaced by INTERMEDIATE 22 and the reagent cicletanine was replaced by (+)-cicletanine. $^1$H-NMR (300 MHz, DMSO-d$_6$): δ 8.16 (1H, s); 7.50-7.39 (4H, m); 6.34 (1H, s); 5.55-5.45 (1H, m); 5.35-5.10 (3H, m); 4.98-4.91 (1H, m); 4.88-4.81 (1H, m); 4.17-3.95 (4H, m); 2.40 (3H, s).

Example 60

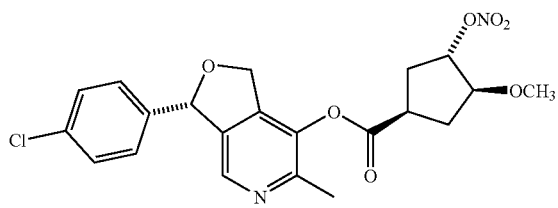

(3S)-3-(4-chlorophenyl)-6-methyl-1,3-dihydrofuro[3,4-c]pyridin-7-yl(1R,3S,4S)-3-methoxy-4-(nitrooxy)cyclopentanecarboxylate

Step A: Methyl (1R,3s,5S)-6-oxabicyclo[3.1.0]hexane-3-carboxylate and methyl (1R,3r,5S)-6-oxabicyclo[3.1.0]hexane-3-carboxylate To a solution of methyl cyclopent-3-ene-1-carboxylate (5.05 g, 40 mmol) in dichloromethane (400 ml) at 0° C. was added 3-chloroperbenzoic acid (10.58 g, 46.0 mmol) portionwise. The reaction was stirred ON at rt. The reaction was concentrated by half and then 300 mL of ether and 200 mL of aqueous potassium carbonate (sat) were added. The organic layer was washed with water, potassium carbonate, water then brine. The organic layer was dried over Na2SO4 and concentrated and the residual clear oil was purified by chromatography on a 100G Biotage Snap cartridge with 10 to 30% (6:3:1 Hex-MTBE-CH3CN)/Hex to give the trans epoxide, methyl (1R,3s,5S)-6-oxabicyclo[3.1.0]hexane-3-carboxylate; $^1$H NMR (500 MHz, CDCl$_3$) δ 1.90 (dd, J=14.0 Hz, J=9.0 Hz, 2H), 2.36 (dd, J=14.0 Hz, J=9.0 Hz, 2H), 2.66 (quintet, J=9.0 Hz, 1H), 3.53 (s, 2H), 3.68 (s, 3H).

Further elution of the column afforded the cis epoxide, methyl (1R,3r,5S)-6-oxabicyclo-[3.1.0]hexane-3-carboxylate; $^1$H NMR (500 MHz, CDCl$_3$) δ 1.87 (dd, J=14.1 Hz, J=9.1 Hz, 2H), 2.71 (d, J=14.1 Hz, 2H), 2.73 (t, J=9.0 Hz, 1H), 3.48 (s, 2H), 3.69 (s, 3H).

Step B: Methyl (1R,3S,4S)-3-hydroxy-4-methoxycyclopentanecarboxylate

To a solution of methyl (1R,3s,5S)-6-oxabicyclo[3.1.0]hexane-3-carboxylate (7.1 g, 49.9 mmol) in methanol (50 ml, 1236 mmol) was added concentrated sulfuric acid (0.023 ml, 0.431 mmol) and the solution was allowed to stir at rt. After 4 h, silica gel tlc (40% MTBE/Hex) showed reaction was complete. The reaction was neutralized with a few drops of saturated aqueous NaHCO3 and the methanol was removed under vacuum. The residue was dissolved in 200 ml dichloromethane, dryed over sodium sulfate and filtered thru a 2" thick pad of silica gel in a 600 mL fritted funnel. The pad was washed with 600 mL of dichloromethane (tlc showed no more product in eluate) and the combined filtrates were concentrated to give the racemic title compound (8.3 g, 47.6 mmol, 95% yield) as a clear oil: $^1$H NMR (500 MHz, CDCl$_3$) δ 1.9 (m, 3H), 2.26 (m, 1H), 2.36 (m, 1H), 3.03 (quintet, J=8.7 Hz, 1H), 3.37 (s, 3H), 3.62 (m, 2H), 3.71 (s, 3H), 4.24 (m, 2H).

Step C: (−)-Methyl (1R,3S,4S)-3-methoxy-4-(nitrooxy)cyclopentanecarboxylate and (+)-methyl (1R,3S,4S)-3-methoxy-4-nitrooxy)cyclopentanecarboxylate A sample of acetic anhydride (26.1 ml, 276 mmol) in a 1 L round bottom flask was cooled to 0° C. in an ice bath. To this was added fuming nitric acid (12.89 ml, 276 mmol), dropwise over a 10 minute period. The solution was stirred at 0° C. for 10 min more and then a solution of methyl (1R,3S,4S)-3-hydroxy-4-methoxycyclopentanecarboxylate (18.5 g, 106 mmol) in 150 ml dichloromethane was added dropwise over a 15 minute period. This solution was stirred at 0° C. After 30 min, tlc (silica gel, 30% MTBE-hexane) showed reaction was complete. The solution was diluted with 200 ml water and 500 ml dichloromethane and the layers were separated. The aqueous layer was washed with 100 ml dichloromethane and the combined organic layer was washed with three 200 mL portions of saturated NaHCO3 (watch out for pressure from CO2 production), then when no more gas was produced, with 300 mL brine. The organic layer was dried over sodium sulfate and filtered thru a 3" thick pad of silica gel in a 600 mL fritted funnel. The pad was washed with another 1 L of dichloromethane and the combined filtrates were concentrated to give the racemic nitrate ester as a clear liquid; $^1$H NMR (500 MHz, CDCl$_3$) δ 2.1 (m, 3H), 2.36 (m, 1H), 2.56 (m, 1H), 2.99 (quintet, J=8.7 Hz, 1H), 3.37 (s, 3H), 3.73 (s, 3H), 3.84 (m, 2H), 5.30 (m, 2H).

The racemic mixture was separated into its enantiomers by SFC chromatography on an OD column using 10% 3:1 Hexane:IPA and 90% CO2. Faster enantiomer [α]$_D$−14.5° (4.9, CHCl$_3$). Faster enantiomer [α]$_D$+14.4 (5.0, CHCl$_3$).

Step D: (+)-(1S,3R,4R)-3-Methoxy-4-(nitrooxy)cyclopentanecarboxylic acid

A solution of (+)-methyl (1R,3S,4S)-3-methoxy-4-(nitrooxy)cyclopentanecarboxylate (0.658 g, 3 mmol) in methanol (12 ml) was cooled to 0° C. To this was added 4N KOH (1.500 ml, 6.00 mmol) dropwise over 10 minutes and the solution was stirred and allowed to warm to 10° C. over 3 h. The reaction mixture was neutralized to pH 7 by addition of 0.5 mL concentrated HCl and then the solution was concentrated under vacuum to remove methanol. To the residue was added 10 ml CHCl3 and 2 mL water and the pH was adjusted to 3-4 by addition of 2M HCl. The layers were separated and the aqueous layer was washed with two 15 mL portions of CHCl3. The combined organic layers were washed with brine and dryed over Na2SO4 to give the title compound (0.566 g, 2.76 mmol, 92% yield) as a colorless oil; $^1$H NMR (500 MHz, CDCl$_3$) δ 2.08-2.18 (m, 2H), 2.32-2.4 (m, 1H), 2.52-2.58 (m, 1H), 3.05 (quintet, J=8.3 Hz, 1H), 3.40 (d, J=0.7 Hz, 3H), 5.31 (m, 2H).

Step E: (+)-(1R,3S,4S)-3-hydroxy-4-methoxycyclopentanecarbonyl chloride

A solution of (+)-(1S,3R,4R)-3-methoxy-4-(nitrooxy)cyclopentanecarboxylic acid (145 mg, 0.707 mmol) in dichloromethane (200 ml) and DMF (1.642 µl, 0.021 mmol) was cooled to 0° C. in an ice bath. To this was added oxalyl chloride (0.235 ml, 2.69 mmol) dropwise. After addition was complete, the solution was stirred at 0° C. for 1 hr. A tlc sample of the product was added to a mini test tube filled with 100 uL methanol. After 15 minutes, tlc showed complete conversion to the methyl ester. Then 1 ml of dichloroethane was added and the solution was evaporated to dryness to give Product 1 (160 mg, 0.716 mmol, 101% yield), which was used IMMEDIATELY without any further purification or characterization.

Step F: (3S)-3-(4-Chlorophenyl)-6-methyl-1,3-dihydrofuro[3,4-c]pyridin-7-yl(1S,3R,4R)-3-methoxy-4-(nitrooxy)cyclopentanecarboxylate To a solution of (+)-(1R,3S,4S)-3-hydroxy-4-methoxycyclopentanecarbonyl chloride (59.8 mg, 0.267 mmol) in 5 ml dichloromethane at rt was added (3S)-3-(4-chlorophenyl)-6-methyl-1,3-dihydrofuro[3,4-c]pyridin-7-ol (70 mg, 0.267 mmol) and pyridine (43.3 µl, 0.535 mmol). The solution was allowed to stir 2 hrs at rt, until tlc showed reaction complete. The solution was concentrated and dried for 30 minutes under vacuum to remove pyridine. Then the residue was dissolved in dichloromethane and filtered through a ¾" thick pad of silica in a 15 mL fritted funnel. The pad was washed with 20 mL portions of 5, 10, 15 and 20% MTBE/dichloromethane to give the title compound; optical rotation in chloroform at 589 nM, α=+1.951 (c=25.0 mg/1 ml CHCl3); $^1$H NMR (500 MHz, CDCl$_3$) δ 2.2-2.28 (m, 1H), 2.3-2.38 (m, 2H) 2.4-2.5 (m, 2H), 2.50 (s, 3H), 2.76-2.82 (m, 1H), 3.35 (m, 1H), 3.45 (s, 3H), 3.94 (m, 1H), 5.05 (d, J=14 Hz, 1H), 5.15 (dd, J=14 Hz, 1H), 5.641 (m, 1H), 6.23 (s, 1H), 7.29 (d, J=8 Hz, 2H), 7.38 (d, J=8 Hz, 2H), 8.10 (s, 1H); LC-MS: m/z 449 ($^{35}$Cl M+1), 451 ($^{37}$Cl M+1).

Example 61

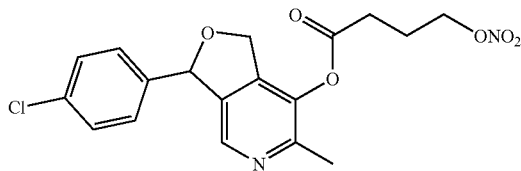

3-(4-Chlorophenyl)-6-methyl-1,3-dihydrofuro[3,4-c]pyridin-7-yl 4-(nitrooxy)butanoate N-Methylmorpholine (79 µL, 0.72 mmol) was added to a stirred solution of (±)-cicletanine (42 mg, 0.16 mmol), 4-(nitrooxy)butanoic acid (24 mg, 0.16 mmol), 1-ethyl-3-(3-dimethylaminopropyl)carbodiimide hydrochloride (37 mg, 0.19 mmol), and 4-dimethylaminopyridine (8 mg, 0.06 mmol) in dichloromethane (1.6 mL). The solution was stirred overnight at room temperature. The mixture was concentrated under reduced pressure. The residue was purified by HPLC reverse phase (C-18) eluting with acetonitrile/water with 0.05% TFA to afford the title compound as a colorless oil. $^1$H NMR (500 MHz, CDCl$_3$) δ 8.37 (s, 1H), 7.41 (d, J=8.5 Hz, 2H), 7.30 (d, J=8.5 Hz, 2H), 6.31 (s, 1H), 5.32 (dd, J=2.0, 15.5 Hz, 1H), 5.20 (dd, J=2.0, 15.5 Hz, 1H), 4.64 (t, J=6.0 Hz, 2H), 2.89 (t, J=7.0 Hz, 2H), 2.54 (s, 3H), 2.27 (pent, J=6.5 Hz, 2H); LC-MS: m/z 392.9 (M+H).

Example 62

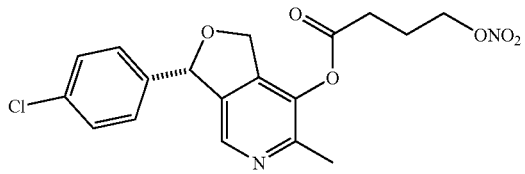

(3S)-3-(4-Chlorophenyl)-6-methyl-1,3-dihydrofuro[3,4-c]pyridin-7-yl 4-(nitrooxy)butanoate N-Methylmorpholine (79 µL, 0.72 mmol) was added to a stirred solution of (S)-(+)-cicletanine (42 mg, 0.16 mmol), 4-(nitrooxy)butanoic acid (24 mg, 0.16 mmol), 1-ethyl-3-(3-dimethylaminopropyl)carbodiimide hydrochloride (37 mg, 0.19 mmol), and 4-dimethylaminopyridine (8 mg, 0.06 mmol) in dichloromethane (1.6 mL). The solution was stirred overnight at room temperature. The mixture was concentrated under reduced pressure. The residue was purified by HPLC reverse phase (C-18) eluting with acetonitrile/water with 0.05% TFA to afford the title compound as a colorless oil. LC-MS: m/z 392.9 (M+H).

Example 63

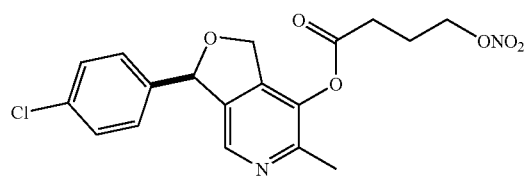

(3R)-3-(4-Chlorophenyl)-6-methyl-1,3-dihydrofuro[3,4-c]pyridin-7-yl 4-(nitrooxy)butanoate N-Methylmorpholine (90 µL, 0.82 mmol) was added to a stirred solution of (R)-(−)-cicletanine (48 mg, 0.18 mmol), 4-(nitrooxy)butanoic acid (27 mg, 0.18 mmol), 1-ethyl-3-(3-dimethylaminopropyl)carbodiimide hydrochloride (42 mg, 0.22 mmol), and 4-dimethylaminopyridine (9 mg, 0.07 mmol) in dichloromethane (1.8 mL). The solution was stirred overnight at room temperature. The mixture was concentrated under reduced pressure. The residue was purified by HPLC reverse phase (C-18) eluting with acetonitrile/water with 0.05% TFA to afford the title compound as a colorless oil. LC-MS: m/z 392.9 (M+H).

Example 64

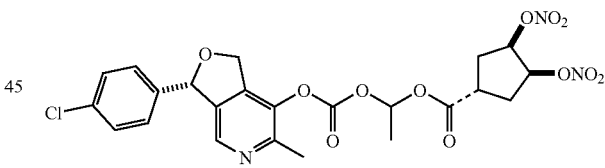

1-[({[(3S)-3-(4-chlorophenyl)-6-methyl-1,3-dihydrofuro[3,4-c]pyridin-7-yl]oxy}carbonyl)oxy]ethyl (1s,3R,4S)-3,4-bis(nitrooxy)cyclopentanecarboxylate Step A: 1-chloroethyl[3-(4-chlorophenyl)-6-methyl-1,3-dihydrofuro[3,4-c]pyridin-7-yl]carbonate To a suspension of 3-(4-chlorophenyl)-6-methyl-1,3-dihydrofuro[3,4-c]pyridin-7-ol (1.309 g, 5 mmol) in dichloromethane (20 ml) was added 1-chloroethylchloroformate (0.566 ml, 5.25 mmol) and pyridine (0.445 ml, 5.50 mmol) and allowed to stir 1 hr. Added 50 ml ether and washed orangic layer two 25 ml portions water and once with 25 ml brine, dryed over sodium sulfate and filtered through a pad of silica with 20% acetone/hexane to give title compound. $^1$H NMR (500 MHz, CDCl$_3$) δ 8.12 (d, J=4.5 Hz, 1H), 7.38 (d, J=8.5 Hz, 2H), 7.30 (d, J=8.5 Hz, 2H), 6.52 (q, J=6.0 Hz, 1H), 6.23 (s, 1H), 5.28 (ddd, J=2.5, 6.5, 14.0 Hz, 1H), 5.15 (ddd, J=14.0, 4.5, 2.0 Hz, 1H), 2.54 (s, 3H), 1.97 (d, J=5.5 Hz, 3H).

Step B: 1-iodoethyl[3-(4-chlorophenyl)-6-methyl-1,3-dihydrofuro[3,4-c]pyridin-7-yl]carbonate To a suspension of sodium iodide (0.965 g, 6.44 mmol) in acetone (20 ml) was added 1-chloroethyl[3-(4-chlorophenyl)-6-methyl-1,3-dihydrofuro[3,4-c]pyridin-7-yl]carbonate (1.694 g, 4.6 mmol) and heated at 50° C. for 8 hrs. The reaction mixture was filtered and evaporated. To the residue was added water (20 mL) and the mixture was extracted with dichloromethane (2×20 mL). The combined organic Fractions were washed with water (5 mL), then with 5 ml aqueous bisulfite then dried over sodium sulfate, filtered and the solvent was evaporated under reduced pressure. Filtered through pad of silica with 10% acetone/dichloromethane to give title product $^1$H NMR (500 MHz, CDCl$_3$) δ 8.12 (d, J=4.5 Hz, 1H), 7.38 (d, J=8.5 Hz, 2H), 7.30 (d, J=8.5 Hz, 2H), 6.85 (q, J=6.0 Hz, 1H), 6.23 (s, 1H), 5.28 (ddd, J=2.5, 6.5, 14.0 Hz, 1H), 5.15 (ddd, J=14.0, 4.5, 2.0 Hz, 1H), 2.54 (s, 3H), 2.38 (d, J=5.5 Hz, 3H). LC-MS m/z 460 ($^{35}$Cl M+1), 462 ($^{37}$Cl M+1)

Step C: [-1,3-3-(4-chlorophenyl)-6-methyl dihydrofuro[3,4-c]pyridin-7-yl]oxycarbonyloxymethyl 3,4-dinitrooxycyclopentanecarboxylate To (1s,3R,4S)-3,4-bis(nitrooxy)cyclopentanecarboxylic acid (283 mg, 1.200 mmol) in 2 ml water was added NaHCO$_3$ (185 mg, 2.200 mmol) and Bu$_4$NHSO$_4$ (407 mg, 1.200 mmol). After 5 minutes a solution of 1-iodoethyl[3-(4-chlorophenyl)-6-methyl-1,3-dihydrofuro[3,4-c]pyridin-7-yl]carbonate (460 mg, 1.0 mmol) in 4 ml ethyl acetate was added and stirred at ambient until LC/MS showed reaction was complete. Separated layers and washed organic layer with 1 ml water, dried over sodium sulfate and concentrated followed by silica gel chromatography on a Biotage 25 g SNAP with 5-20% 6:3:1 Hexane-MTBE-MeCN/afforded title product. LC-MS m/z 568 ($^{35}$Cl M+1), 570 ($^{37}$Cl M+1)

The following examples were prepared using procedures analogous to those described for EXAMPLE 64 substituting the appropriate chloromethylchloroformate or chloroacetylchloride.

Example 65

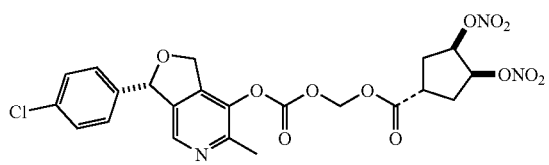

(3S)-3-(4-Chlorophenyl)-6-methyl-1,3-dihydrofuro[3,4-c]pyridin-7-yl-oxycarbonyloxymethyl (1s,3R,4S)-3,4-bis(nitrooxy)cyclopentanecarboxylate m/z 554 ($^{35}$Cl M+1), 556 ($^{37}$Cl M+1)

Example 66

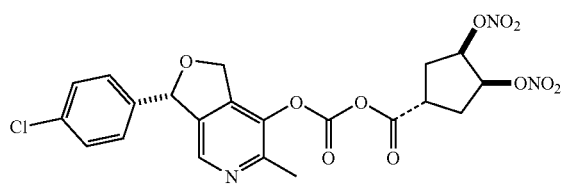

(3S)-3-(4-Chlorophenyl)-6-methyl-1,3-dihydrofuro[3,4-c]pyridin-7-yl-oxycarbonyl (1s,3R,4S)-3,4-bis(nitrooxy)cyclopentanecarboxylate m/z 524 ($^{35}$Cl M+1), 526 ($^{37}$Cl M+1)

Example 67

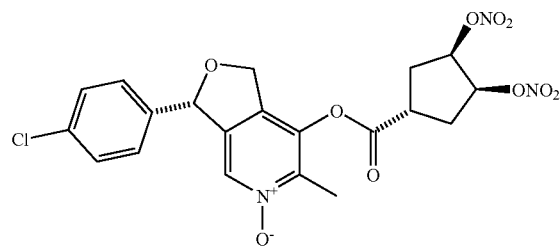

[3-(4-chlorophenyl)-6-methyl-5-oxido-1,3-dihydrofuro[3,4-c]pyridin-5-ium-7-yl](3S,4R)-3,4-dinitrooxycyclopentanecarboxylate A stock solution of 200 mg m-CPBA in 4 ml chloroform over sieves was allowed to stand 15 minutes. To (3S)-3-(4-chlorophenyl)-6-methyl-1,3-dihydrofuro[3,4-c]pyridin-7-yl (1s,3R,4S)-3,4-bis(nitrooxy)cyclopentanecarboxylate (98 mg, 0.204 mmol) in dry Chloroform (3 ml) was added 75 ml of the dried stock m-CPBA solution and allowed to stir at ambient for 3 hrs. LC/MS showed reaction complete. Filtered and partitioned between dichloromethane and NaHCO3 (aq). The organic layer washed with water and brine then dried over sodium sulfate. Concentrated and collected solid to give title product LC-MS m/z 496 ($^{35}$Cl M+1), 498 ($^{37}$Cl M+1)

The following were prepared from the appropriate epoxide or diol as previously described in EXAMPLES 8 and EXAMPLES 60.

| Structure | Ex. | m/z | ¹H NMR (500 MHz CDCl₃) |
|---|---|---|---|
| 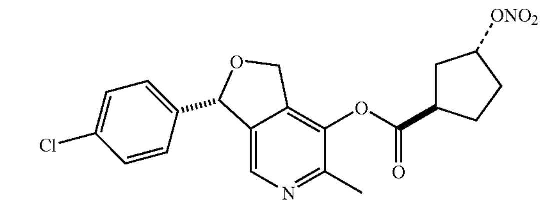 | 68 | 419 (M + 1, ³⁵Cl); 421 (M + 1, ³⁷Cl) | δ 2.02-2.17 (m, 1 H), 2.26-2.50 (m, 4 H), 2.47 (s, 3 H), 3.32-3.40 (m, 1 H), 5.05 (dd, J = 13.6, 1.6 Hz, 1 H), 5.16 (dd, J = 13.7, 2.3 Hz, 1 H), 5.56 (m, 1 H), 6.23 (s, 1 H), 7.29 (d, J = 8.3 Hz, 2 H), 7.37 (d, J = 8.4 Hz, 2 H), 8.09 (s, 1 H) |
| 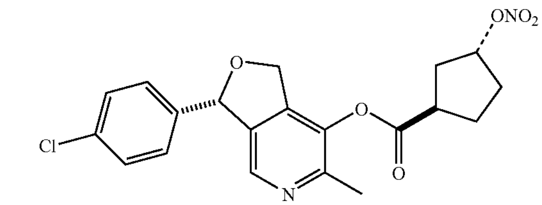 | 69 | 419 (M + 1, ³⁵Cl); 421 (M + 1, ³⁷Cl) | δ 2.02-2.17 (m, 1 H), 2.26-2.50 (m, 4 H), 2.47 (s, 3 H), 3.32-3.40 (m, 1 H), 5.05 (dd, J = 13.6, 1.6 Hz, 1 H), 5.16 (dd, J = 13.7, 2.3 Hz, 1 H), 5.56 (m, 1 H), 6.23 (s, 1 H), 7.29 (d, J = 8.3 Hz, 2 H), 7.37 (d, J = 8.4 Hz, 2 H), 8.09 (s, 1 H) |
| 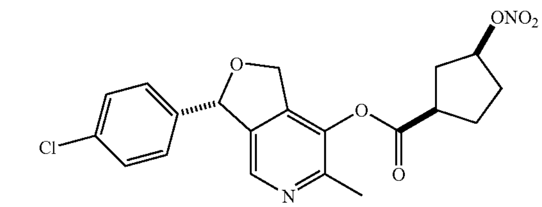 | 70 | 419 (M + 1, ³⁵Cl); 421 (M + 1, ³⁷Cl) | δ 2.11-2.18 (m, 1 H), 2.24-2.29 (m, 2 H), 2.40-2.46 (m, 1 H), 3.24 (m, 1 H), 5.07 (dd, J = 13.7, 1.8 Hz, 1 H), 5.18 (dd, J = 13.7, 2.4 Hz, 1 H), 5.48 (m, 1 H), 6.23 (s, 1 H), 7.29 (d, J = 7.5 Hz, 2 H), 7.37 (d, J = 8.5 Hz, 2 H), 8.09 (s, 1 H) |
| 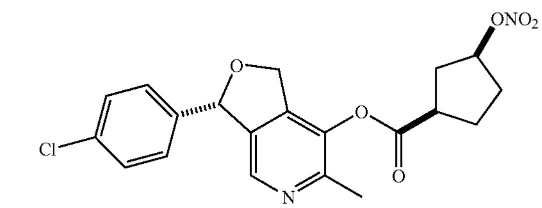 | 71 | 419 (M + 1, ³⁵Cl); 421 (M + 1, ³⁷Cl) | δ 2.11-2.18 (m, 1 H), 2.24-2.29 (m, 2 H), 2.40-2.46 (m, 1 H), 3.24 (m, 1 H), 5.07 (dd, J = 13.7, 1.8 Hz, 1 H), 5.18 (dd, J = 13.7, 2.4 Hz, 1 H), 5.48 (m, 1 H), 6.23 (s, 1 H), 7.29 (d, J = 7.5 Hz, 2 H), 7.37 (d, J = 8.5 Hz, 2 H), 8.09 (s, 1H) |
| 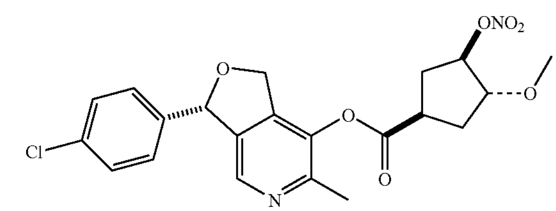 | 72 | 449 (M + 1, ³⁵Cl); 451 (M + 1, ³⁷Cl) | δ 2.26-2.34 (m, 3 H), 2.47 (s, 3 H), 2.7-2.78 (m, 1 H) 3.28-3.45 (m, 1 H), 3.47 (s, 3 H), 3.98 (m, 1 H), 5.05 (dd, J = 13.7, 2.3 Hz, 1 H), 5.12 (dd, J = 13.7, 2.3 Hz, 1 H), 5.34 (m, 1 H), 6.22 (s, 1 H), 7.29 (d, J = 8.4 Hz, 2 H), 7.37 (d, J = 8.4 Hz, 2 H), 8.09 (s, 1 H) |
| 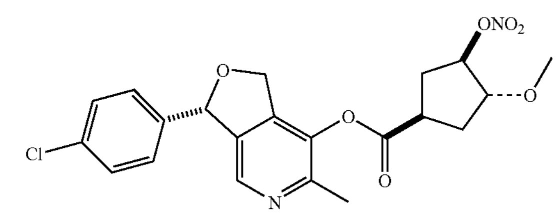 | 73 | 449 (M + 1, ³⁵Cl); 451 (M + 1, ³⁷Cl) | δ 2.26-2.34 (m, 3 H), 2.47 (s, 3 H), 2.7-2.78 (m, 1 H) 3.28-3.45 (m, 1 H), 3.47 (s, 3 H), 3.98 (m, 1 H), 5.05 (dd, J = 13.7, 2.3 Hz, 1 H), 5.12 (dd, J = 13.7, 2.3 Hz, 1 H), 5.34 (m, 1 H), 6.22 (s, 1 H), 7.29 (d, J = 8.4 Hz, 2 H), 7.37 (d, J = 8.4 Hz, 2 H), 8.09 (s, 1 H) |
| 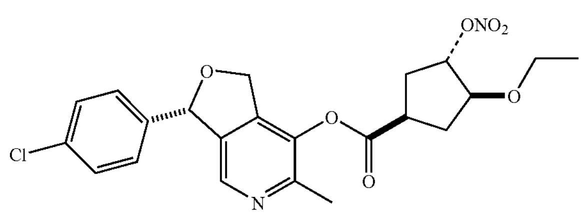 | 74 | 463 (M + 1, ³⁵Cl); 465 (M + 1, ³⁷Cl) | δ 1.27 (t, J = 7.0 Hz, 3 H), 2.20-2.32 (m, 2 H), 2.45-2.53 (m, 1 H), 2.45 (s, 3 H) 2.78 (m, 1 H) 2.30-3.38 (m, 1 H), 3.57-3.69 (m, 1 H), 4.03 (m, 1 H), 5.06 (dd, J = 13.8, 1.8 Hz, 1 H), 5.17 (dd, J = 13.8, 2.3 Hz, 1 H), 5.40 (m, 1 H), 6.23 (s, 1 H), 7.29 (d, J = 7.7 Hz, 2 H), 7.38 (d, J = 8.3 Hz, 2 H), 8.09 (s, 1 H) |

-continued

| Structure | Ex. | m/z | ¹H NMR (500 MHz CDCl₃) |
|---|---|---|---|
| 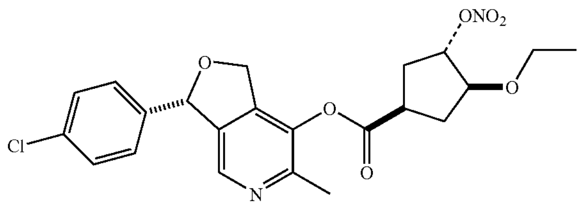 | 75 | 463 (M + 1, ³⁵Cl); 465 (M + 1, ³⁷Cl) | δ 1.27 (t, J = 7.0 Hz, 3 H), 2.20-2.32 (m, 2 H), 2.45-2.53 (m, 1 H), 2.45 (s, 3 H), 2.78 (m, 1 H) 2.30-3.38 (m, 1 H), 3.57-3.69 (m, 1 H), 4.03 (m, 1 H), 5.06 (dd, J = 13.8, 1.8 Hz, 1 H), 5.17 (dd, J = 13.8, 2.3 Hz, 1 H), 5.40 (m, 1 H), 6.23 (s, 1 H), 7.29 (d, J = 7.7 Hz, 2 H), 7.38 (d, J = 8.3 Hz, 2 H), 8.09 (s, 1 H) |
| 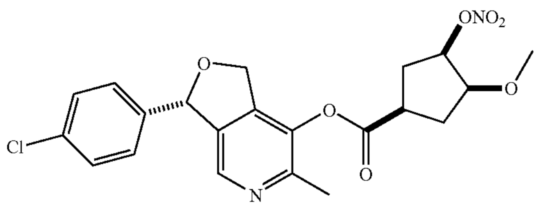 | 76 | 449 (M + 1, ³⁵Cl); 451 (M + 1, ³⁷Cl) | δ 2.37-2.43 (m, 2 H), 2.49 (s, 3 H), 2.51-2.56 (m, 1 H) 3.15-3.23 (m, 1 H), 3.44 (s, 3 H), 3.99 (m, 1 H), 5.07 (dd, J = 13.8, 1.9 Hz, 1 H), 5.17 (dd, J = 13.7, 2.4 Hz, 1 H), 5.39 (m, 1 H), 6.23 (s, 1 H), 7.29 (d, J = 7.3 Hz, 2 H), 7.38 (d, J = 8.5 Hz, 2 H), 8.09 (s, 1 H) |
| 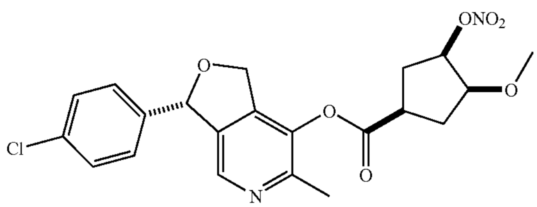 | 77 | 449 (M + 1, ³⁵Cl); 451 (M + 1, ³⁷Cl) | δ 2.37-2.43 (m, 2 H), 2.49 (s, 3 H), 2.51-2.56 (m, 1 H) 3.15-3.23 (m, 1 H), 3.44 (s, 3 H), 3.99 (m, 1 H), 5.07 (dd, J = 13.8, 1.9 Hz, 1 H), 5.17 (dd, J = 13.7, 2.4 Hz, 1 H), 5.39 (m, 1 H), 6.23 (s, 1 H), 7.29 (d, J = 7.3 Hz, 2 H), 7.38 (d, J = 8.5 Hz, 2 H), 8.09 (s, 1 H) |
| 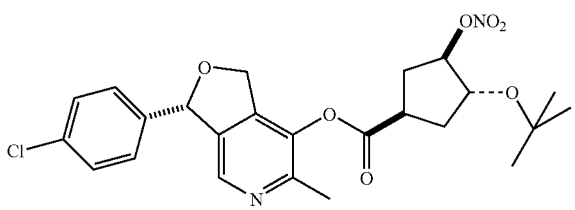 | 78 | 491 (M + 1, ³⁵Cl); 493 (M + 1, ³⁷Cl) | δ 1.25 (σ, 9 H), 2.10-2.16 (m, 1 H), 2.20-2.26 (m, 1 H), 2.49 (s, 3 H), 2.46-2.54 (m, 1 H) 2.68-2.75 (m, 1 H), 3.29 (m, 1 H), 4.20 (m, 1 H), 5.06 (dd, J = 13.8, 1.8 Hz, 1 H), 5.17 (dd, J = 13.7, 2.4 Hz, 1 H), 5.26 (m, 1 H), 6.23 (s, 1 H), 7.29 (d, J = 8.4 Hz, 2 H), 7.38 (d, J = 8.3 Hz, 2 H), 8.09 (s, 1 H) |
| 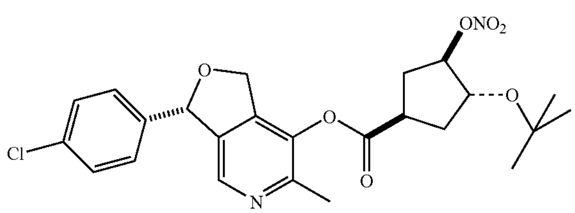 | 79 | 491 (M + 1, ³⁵Cl); 493 (M + 1, ³⁷Cl) | δ 1.25 (σ, 9 H), 2.10-2.16 (m, 1 H), 2.20-2.26 (m, 1 H), 2.49 (s, 3 H), 2.46-2.54 (m, 1 H) 2.68-2.75 (m, 1 H), 3.29 (m, 1 H), 4.20 (m, 1 H), 5.06 (dd, J = 13.8, 1.8 Hz, 1 H), 5.17 (dd, J = 13.7, 2.4 Hz, 1 H), 5.26 (m, 1 H), 6.23 (s, 1 H), 7.29 (d, J = 8.4 Hz, 2 H), 7.38 (d, J = 8.3 Hz, 2 H), 8.09 (s, 1 H) |
| 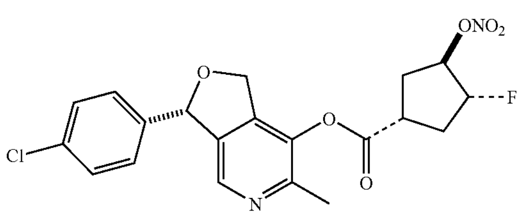 | 80 | 437 (M + 1, ³⁵Cl); 439 (M + 1, ³⁷Cl) | δ 2.27-2.34 (m, 1 H), 2.48 (s, 3 H), 2.51-2.63 (m, 1 H), 2.83-3.91 (m, 1 H), 3.42-3.54 (m, 1 H), 5.05 (dd, J = 13.7, 1.7 Hz, 1 H), 5.16 (dd, J = 13.7, 2.4 Hz, 1 H), 5.19 (d of m J = 50 Hz, 1 H), 5.42-5.58 (m, 1 H), 6.23 (s, 1 H), 7.29 (d, J = 8.5 Hz, 2 H), 7.38 (d, J = 8.4 Hz, 2 H), 8.10 (s, 1 H) |
| 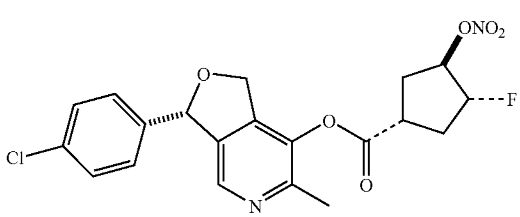 | 81 | 437 (M + 1, ³⁵Cl); 439 (M + 1, ³⁷Cl) | δ 2.27-2.34 (m, 1 H), 2.48 (s, 3 H), 2.51-2.63 (m, 1 H), 2.83-3.91 (m, 1 H), 3.42-3.54 (m, 1 H), 5.05 (dd, J = 13.7, 1.7 Hz, 1 H), 5.16 (dd, J = 13.7, 2.4 Hz, 1 H), 5.19 (d of m J = 50 Hz, 1 H), 5.42-5.58 (m, 1 H), 6.23 (s, 1 H), 7.29 (d, J = 8.5 Hz, 2 H), 7.38 (d, J = 8.4 Hz, 2 H), 8.10 (s, 1 H) |

| Structure | Ex. | m/z | $^1$H NMR (500 MHz CDCl$_3$) |
|---|---|---|---|
| [structure with ONO$_2$, methoxy, chlorophenyl dihydrofuropyridine] | 82 | 449 (M + 1, $^{35}$Cl); 451 (M + 1, $^{37}$Cl) | δ 2.23-2.29 (m, 1 H), 2.35-2.92 (m, 2 H), 2.48 (s, 3 H), 2.44-2.51 (m, 1 H), 3.44-3.51 (m, 1 H), 3.45 (s, 3 H), 4.11 (m, 1 H), 5.06 (dd, J = 13.7, 1.8 Hz, 1 H), 5.16 (dd, J = 13.6, 2.4 Hz, 1 H), 5.48-5.52 (m, 1 H), 6.23 (s, 1 H), 7.30 (d, J = 8.3 Hz, 2 H), 7.38 (d, J = 8.4 Hz, 2 H), 8.10 (s, 1 H) |
| [structure with ONO$_2$, methoxy, chlorophenyl dihydrofuropyridine] | 83 | 449 (M + 1, $^{35}$Cl); 451 (M + 1, $^{37}$Cl) | δ 2.23-2.29 (m, 1 H), 2.35-2.92 (m, 2 H), 2.48 (s, 3 H), 2.44-2.51 (m, 1 H), 3.44-3.51 (m, 1 H), 3.45 (s, 3 H), 4.11 (m, 1 H), 5.06 (dd, J = 13.7, 1.8 Hz, 1 H), 5.16 (dd, J = 13.6, 2.4 Hz, 1 H), 5.48-5.52 (m, 1 H), 6.23 (s, 1 H), 7.30 (d, J = 8.3 Hz, 2 H), 7.38 (d, J = 8.4 Hz, 2 H), 8.10 (s, 1 H) |

Examples 68-83 compound names:
68: (3S)-3-(4-chlorophenyl)-6-methyl-1,3-dihydrofuro[3,4-c]pyridin-7-yl(1R,3R)-3-(nitrooxy)cyclopentanecarboxylate,
69: (3S)-3-(4-chlorophenyl)-6-methyl-1,3-dihydrofuro[3,4-c]pyridin-7-yl(1R,3R)-3-(nitrooxy)cyclopentanecarboxylate,
70: (3S)-3-(4-chlorophenyl)-6-methyl-1,3-dihydrofuro[3,4-c]pyridin-7-yl(1R,3S)-3-(nitrooxy)cyclopentanecarboxylate,
71: (3S)-3-(4-chlorophenyl)-6-methyl-1,3-dihydrofuro[3,4-c]pyridin-7-yl(1R,3S)-3-(nitrooxy)cyclopentanecarboxylate,
72: (3S)-3-(4-chlorophenyl)-6-methyl-1,3-dihydrofuro[3,4-c]pyridin-7-yl(1R,3R,4R)-3-methoxy-4-(nitrooxy)cyclopentanecarboxylate,
73: (3S)-3-(4-chlorophenyl)-6-methyl-1,3-dihydrofuro[3,4-c]pyridin-7-yl(1R,3R,4R)-3-methoxy-4-(nitrooxy)cyclopentanecarboxylate,
74: (3S)-3-(4-chlorophenyl)-6-methyl-1,3-dihydrofuro[3,4-c]pyridin-7-yl(1R,3S,4S)-3-ethoxy-4-(nitrooxy)cyclopentanecarboxylate,
75: (3S)-3-(4-chlorophenyl)-6-methyl-1,3-dihydrofuro[3,4-c]pyridin-7-yl(1R,3S,4S)-3-ethoxy-4-(nitrooxy)cyclopentanecarboxylate,
76: (3S)-3-(4-chlorophenyl)-6-methyl-1,3-dihydrofuro[3,4-c]pyridin-7-yl(1R,3S,4R)-3-methoxy-4-(nitrooxy)cyclopentanecarboxylate,
77: (3S)-3-(4-chlorophenyl)-6-methyl-1,3-dihydrofuro[3,4-c]pyridin-7-yl(1R,3S,4R)-3-methoxy-4-(nitrooxy)cyclopentanecarboxylate,
78: (3S)-3-(4-chlorophenyl)-6-methyl-1,3-dihydrofuro[3,4-c]pyridin-7-yl(1S,3R,4R)-3-tert-butoxy-4-(nitrooxy)cyclopentanecarboxylate,
79: (3S)-3-(4-chlorophenyl)-6-methyl-1,3-dihydrofuro[3,4-c]pyridin-7-yl(1S,3R,4R)-3-tert-butoxy-4-(nitrooxy)cyclopentanecarboxylate,
80: (3S)-3-(4-chlorophenyl)-6-methyl-1,3-dihydrofuro[3,4-c]pyridin-7-yl(1R,3R,4R)-3-fluoro-4-(nitrooxy)cyclopentanecarboxylate,
81: (3S)-3-(4-chlorophenyl)-6-methyl-1,3-dihydrofuro[3,4-c]pyridin-7-yl(1R,3R,4R)-3-fluoro-4-(nitrooxy)cyclopentanecarboxylate,
82: (3S)-3-(4-chlorophenyl)-6-methyl-1,3-dihydrofuro[3,4-c]pyridin-7-yl(1S,3S,4R)-3-methoxy-4-(nitrooxy)cyclopentanecarboxylate, and
83: (3S)-3-(4-chlorophenyl)-6-methyl-1,3-dihydrofuro[3,4-c]pyridin-7-yl(1S,3S,4R)-3-methoxy-4-(nitrooxy)cyclopentanecarboxylate.

Example 84

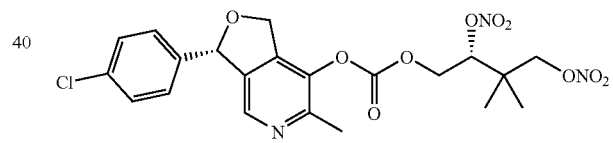

(S)-3-(4-chlorophenyl)-6-methyl-1,3-dihydrofuro[3,4-c]pyridin-7-yl(R)-3,3-dimethyl-2,4-bis(nitrooxy)butyl carbonate The compound was prepared using procedure analogous to that described for EXAMPLE 37 substituting (1r,3R,4S)-3,4-bis(nitrooxy)-cyclopentyl 1-chloroethyl carbonate with INTERMEDIATE 29.

$^1$H NMR (CDCl3): 8.19 (1H, s); 7.37 (2H, d); 7.29 (2H, d); 6.22 (1H, s); 5.39 (1H, m); 5.21 (2H, q); 4.76 (1H, m); 4.39 (3H, m); 2.51 (3H, s); 1.59 (3H, s); 1.20 (6H, d).

Example 85-87

The following examples were prepared using procedures analogous to those described for EXAMPLE 50, using respectively INTERMEDIATES 30, 31 and 32, instead of INTERMEDIATE 17

| EXAMPLE | STRUCTURE | 1H NMR (300 MHz, DMSO) δ (ppm) |
|---|---|---|
| 85 | 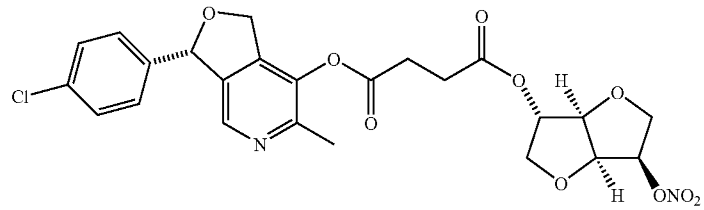 | 8.13 (s, 1 H), 7.43 (m, 4 H), 6.33 (s, 1 H), 5.52 (m, 1 H), 5.17 (m, 2 H), 4.99 (m, 2 H), 4.43 (m, 1 H), 4.03-3.79 (m, 4 H), 2.96 (m, 2 H), 2.76 (m, 2 H), 2.36 (s, 3 H). |
| 86 | 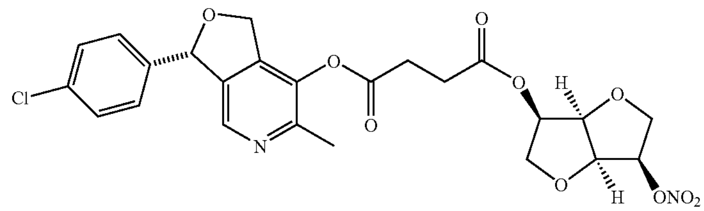 | 8.13 (s, 1 H), 7.43 (m, 4 H), 6.33 (s, 1 H), 5.49 (m, 1 H), 5.19-4.94 (m, 3 H), 4.87 (m, 1 H), 4.63 (m, 1 H), 4.06 (m, 1 H), 3.93 (m, 2 H), 3.63 (m, 1 H), 2.95 (m, 2 H), 2.78 (m, 2 H), 2.36 (s, 3 H). |
| 87 | 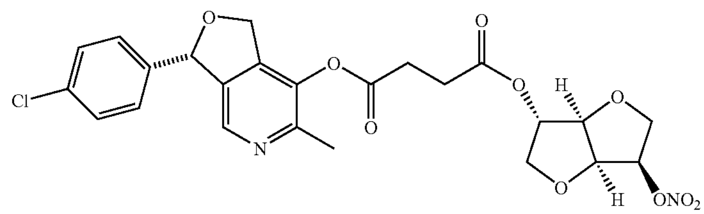 | 8.13 (s, 1 H), 7.44 (m, 4 H), 6.33 (s, 1 H), 5.45 (m, 1 H), 5.16 (m, 1 H), 5.13 (m, 1 H), 4.99 (m, 1 H), 4.83 (m, 1 H), 4.61 (m, 1 H), 4.03-3.82 (m, 4 H), 2.96 (m, 2 H), 2.76 (m, 2 H), 2.37 (s, 3 H). |

Examples 85-87 compounds names:
(S)-3-(4-chlorophenyl)-6-methyl-1,3-dihydrofuro[3,4-c]pyridin-7-yl(3S,3aR,6R,6aS)-6-(nitrooxy)hexahydrofuro[3,2-b]furan-3-yl succinate
(S)-3-(4-chlorophenyl)-6-methyl-1,3-dihydrofuro[3,4-c]pyridin-7-yl(3R,3aR,6R,6aS)-6-(nitrooxy)hexahydrofuro[3,2-b]furan-3-yl succinate
(S)-3-(4-chlorophenyl)-6-methyl-1,3-dihydrofuro[3,4-c]pyridin-7-yl(3S,3aR,6S,6aS)-6-(nitrooxy)hexahydrofuro[3,2-b]furan-3-yl succinate Example 88

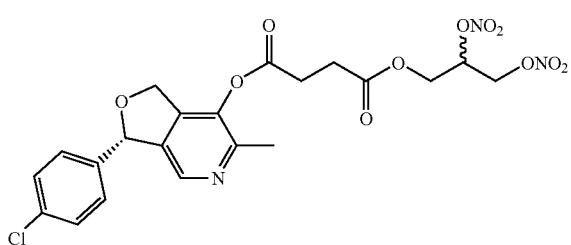

2,3-bis(nitrooxy)propyl (S)-3-(4-chlorophenyl)-6-methyl-1,3-dihydrofuro[3,4-c]pyridin-7-yl succinate Step A: 4-(allyloxy)-4-oxobutanoic acid To a solution of allyl alcohol (2.27 g, 39.0 mmol) in dichloromethane (60 ml), triethylamine (6.27 ml, 4.55 mmol) was added, then succinic anhydride (3.00 g, 30.0 mmol) was slowly added; the mixture was stirred at rt overnight. Then the mixture was diluted in dichloromethane and washed with 5% solution of NaH$_2$PO$_4$ (2×80 mL). The organic layer was dried over sodium sulfate, filtered and evaporated in vacuo, affording 3.90 g of desired product as a colourless oil.
$^1$H NMR (300 MHz, CDCl$_3$) δ 5.93 (m, 1H), 5.31 (m, 1H), 4.63 (d, 2H), 2.70 (m, 4H).

Step B: (S)-allyl 3-(4-chlorophenyl)-6-methyl-1,3-dihydrofuro[3,4-c]pyridin-7-yl succinate The title compound was prepared from the compound obtained in step A following the procedure described for EXAMPLE 50.
$^1$H NMR (300 MHz, DMSO) δ 8.13 (s, 1H), 7.44 (m, 4H), 6.33 (s, 1H), 5.92 (m, 1H), 5.38-4.95 (m, 4H), 4.60 (d, 2H), 2.96 (m, 2H), 2.78 (m, 2H), 2.36 (s, 3H).

Step C: 2,3-bis(nitrooxy)propyl (S)-3-(4-chlorophenyl)-6-methyl-1,3-dihydrofuro[3,4-c]pyridin-7-yl succinate To a solution of compound obtained in Step B (0.600 g, 1.49 mmol) in acetonitrile (10 mL) at −20° C., silver nitrate (0.253 g, 1.49 mmol) and iodine (0.378 g, 1.49 mmol) were added. The mixture was stirred at −20° C. for about 1 hour. Then further silver nitrate was added (0.505 g, 2.98 mmol) and the mixture was heated at 70° C. for 8 hours and at rt for 2 days. Then the silver salts were filtered off and the solution was concentrated. The residue was purified by chromatography on a 100G Biotage Snap cartridge with 20% to 100% EtOAc in Hex in 10 volumes of eluent, to give the title product, as yellow oil.
$^1$H NMR (300 MHz, DMSO) δ 8.13 (s, 1H), 7.44 (m, 4H), 6.33 (s, 1H), 5.67 (m, 1H), 5.19-4.92 (m, 3H), 4.84 (m, 1H), 4.51 (m, 1H), 4.39 (m, 1H), 2.96 (m, 2H), 2.78 (m, 2H), 2.36 (s, 3H).

Mononitrate compounds that have been orally dosed to rats result in nitrites (metabolites of nitric oxide) circulating in plasma with maximal concentrations in the 0.5-2 μM range. Similar dosing of isosorbide mononitrate compounds described in this invention results in increased circulating nitrite concentrations. Biochemical evidence for the generation of NO in vivo in response to test compound administration was obtained from studies in Sprague-Dawley rats. Administration of test compound to fasted SD rats (40 mpk, PO) results in the appearance of reactive nitrogen species (RNS), assessed using the diaminonapthalene derivitization (DAN) assay.

RNS were delected as S-nitrosothiols (RNSOs) in EDTA-treated rat plasma using an HPLC fluorescent assay based on the method of Kostka and Park (Methods Enzymol. 1999, 301, 227-235). The method is based on the detection of fluorescent 2,3-naphthotriazole (NAT) formed in the reaction between acidified 2,3-diaminonaphthalene and the nitrosonium moiety of RSNOs released by $HgCl_2$-mediated breakdown of the S—NO bond. The reaction mixture was chromatographed by reversed phase HPLC, and the fluorescent signal of the resolved NAT peak was quantified.

Plasma (20 μL) was first diluted 1:1 in $H_2O$ (20 μL) in a black polypropylene untreated microtiter plate. DAN reagent (100 μL per well, 100 μM DAN in 0.1 N HCl, 4 mM $HgCl_2$) was added, and the plate was immediately sealed with an opaque plate mat, vortexed, and incubated in the dark for 10 min. Plates were centrifuged (2000×g, 5 min) and chilled to 4° C. before HPLC analysis. HPLC was carried out on an Agilent 1200 system using a chilled autosampler (4° C.). Samples were chromatographed on a C8 column (Zorbax Eclipse XDB-C8, 4.6×150 mm, 5 μm) with isocratic elution using a mobile phase of 67% MeOH, 0.1% $NH_4OAc$ and a flow rate of 2 mL/min. NAT fluorescence was monitored at 450 nm using an excitation wavelength of 360 nm. Calibration curves were prepared using $NaNO_2$ in control plasma.

Vessel Relaxation

The ability of the compounds of the invention to induce vasorelaxation was tested in vitro in isolated rabbit thoracic aorta preparations (Wanstall J. C. et al., Br. J. Pharmacol., 134:463-472, 2001). Male New Zealand rabbits were anaesthetized with thiopental-Na (50 mg/kg, iv), sacrificed by exsanguinations and then the thorax was opened and the aorta dissected. Aortic ring preparations (4 mm in length) were set up in physiological salt solution (PSS) at 37° C. in small organ chambers (5 ml). The composition of PSS was (mM): NaCl 130, $NaHCO_3$ 14.9, $KH_2PO_4$ 1.2, $MgSO_4$ 1.2, HEPES 10, $CaCl_2$, ascorbic acid 170 and glucose 1.1 (95% $O_2$/5% $CO_2$; pH 7.4). Each ring was mounted under 2 g passive tension. Isometric tension was recorded with a Grass transducer (Grass FT03) attached to a BIOPAC MP150 System. Preparations were allowed to equilibrate for 1 h, and then contracted submaximally with noradrenaline (NA, 1 μM) and, when the contraction was stable, acetylcholine (ACh, 10 μM) was added. A relaxant response to ACh indicated the presence of a functional endothelium. Vessels that were unable to contract NA or showed no relaxation to ACh were discarded. When a stable precontraction was reached, a cumulative concentration-response curve to either of the vasorelaxant agents was obtained in the presence of a functional endothelium. Each arterial ring was exposed to only one combination of inhibitor and vasorelaxant. Moreover, the effect of the soluble guanylyl cyclase inhibitor ODQ (1-H-(1,2,4)-oxadiazol(4,3-a)quinoxalin-1-one) on vasorelaxation elicited by the compounds was examined preincubating the aortic rings with ODQ (10 μM) for 20 min.

Responses to relaxing agents are expressed as a percentage of residual contraction and plotted against concentration of test compound. $EC_{50}$ values (where $EC_{50}$ is the concentration producing 50% of the maximum relaxation to the test compound) were interpolated from these plots.

During the experimental period, the plateau obtained with NA was stable without significant spontaneous loss of contraction in the aortic rings.

As shown in data Table 1, the compounds of the invention were able to induce relaxation in a concentration-dependent manner. Furthermore, in experiments performed in the presence of ODQ (10 μM), the vasorelaxant responses to tested compounds were inhibited.

TABLE I

Vessel Relaxation Data

| Compound | $ED_{50}$ (uM) |
|---|---|
| Vehicle | >1000 |
| 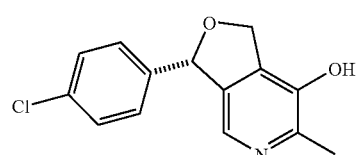 | 35.8 |
| 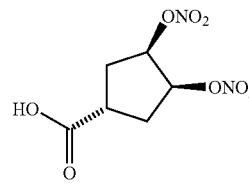 | 5.26 |
| 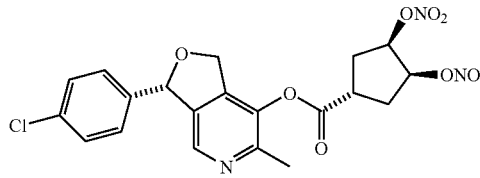 | 6.29 |
| 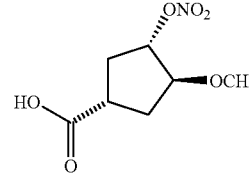 | 125.9 |
| 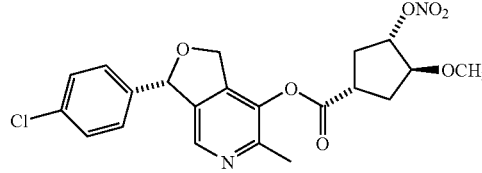 | 18.8 |
| SNAP (S-nitroso-N-acetylpenicillamine) | 0.237 |

Examples 39, 40, 45 and 60 all had vessel relaxation EC50s<50 μM.

What is claimed is:

1. A compound having the general formula I:

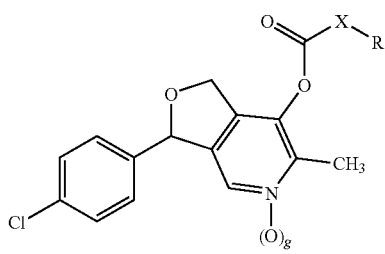

wherein

X is selected from the group consisting of:
a bond, —NHCH$_2$(CH$_2$)$_n$CH$_2$OC(O)—, —CH$_2$NHC(O)CH$_2$NHC(O)—, —CH$_2$OC(O)—, —OCH(CH$_3$)OC(O)—, —OCH$_2$OC(O)—, —O—, —NR$^1$—, —CR$^1$R$^3$—, —(CH$_2$)$_p$—, —(CH$_2$)$_p$NR$^1$C(O)—, —CHR$^5$NR$^2$C(O)—, —(CH$_2$)$_q$C(O)—, —(CH$_2$)$_q$C(O)NR$^1$—,

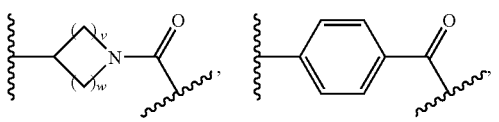

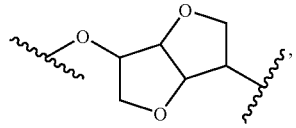

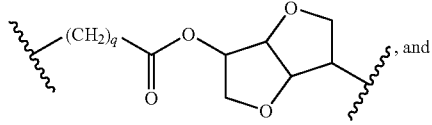, and

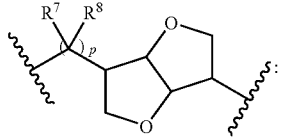:

R$^1$, R$^2$, R$^7$ and R$^8$, each instance in which they occur, are independently selected from the group consisting of hydrogen and C$_{1-7}$ alkyl;

R$^3$ is hydrogen, C$_{1-4}$ alkyl, —CH$_2$ONO$_2$, or —ONO$_2$;

R$^5$ and R$^9$ are independently selected from the group consisting of hydrogen, —CH$_3$, —CH$_2$CH$_3$, —CH(CH$_3$)$_2$, —C(CH$_3$)$_3$, —CH$_2$OH, —CH(OH)CH$_3$, and —CH$_2$C$_6$H$_5$;

g is 0 or 1;
p is 0, 1, 2, 3, 4, 5, 6, or 7;
q is 1, 2, 3, 4, or 5;
v and w are independently selected from the group consisting of 0, 1, 2, and 3, provided that
v+w is 1, 2, 3 or 4;

R is selected from the group consisting of
—(CH$_2$)$_x$CH(ONO$_2$)(CH$_2$)$_y$CH$_3$,
—(CH$_2$)$_x$CH(ONO$_2$)(CH$_2$)$_y$CH(ONO$_2$)(CH$_2$)$_z$CH$_3$,
—(CH$_2$)$_x$CH(ONO$_2$)(CH$_2$)$_y$CH$_2$(ONO$_2$),
—(CH$_2$)$_x$CH(ONO$_2$)(CR$^1$R$^2$)CH$_2$(ONO$_2$),
—CR$^1$R$^2$R$^3$, with the proviso that R$^3$ is —CH$_2$ONO$_2$ or —ONO$_2$,
—(CH$_2$)$_x$(ONO$_2$),
—O—C(O)—(CH$_2$)$_x$CH(ONO$_2$)(CH$_2$)$_y$CH$_2$(ONO$_2$),

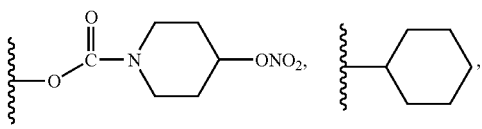

with the proviso that X is CR$^1$R$^3$ and R$^3$ is —CH$_2$ONO$_2$ or —ONO$_2$,

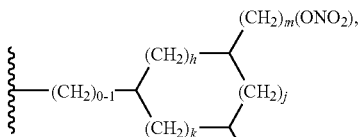

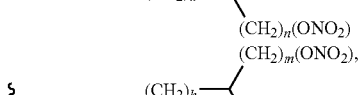

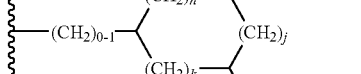

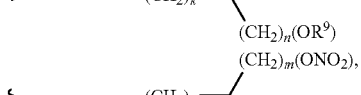

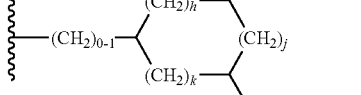

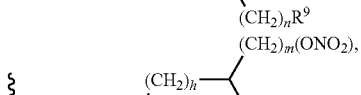

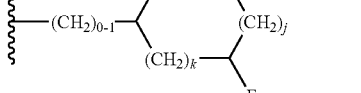

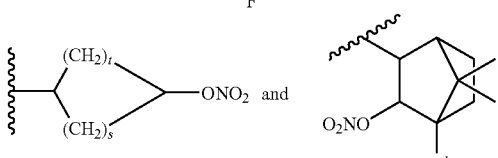

provided that when R is
—O—C(O)—(CH$_2$)—CH(ONO$_2$)(CH$_2$)$_y$CH$_2$(ONO$_2$) or

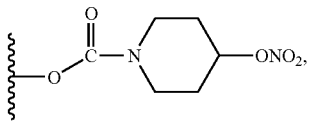

then X is selected from the group consisting of a bond,
—NR¹—, —CR¹R³—, —(CH₂)$_p$—, —(CH₂)$_q$NR¹C(O)—,
—CHR⁵NR²C(O)—, —(CH₂)$_q$C(O)—, —(CH₂)$_q$C(O)NR¹—,

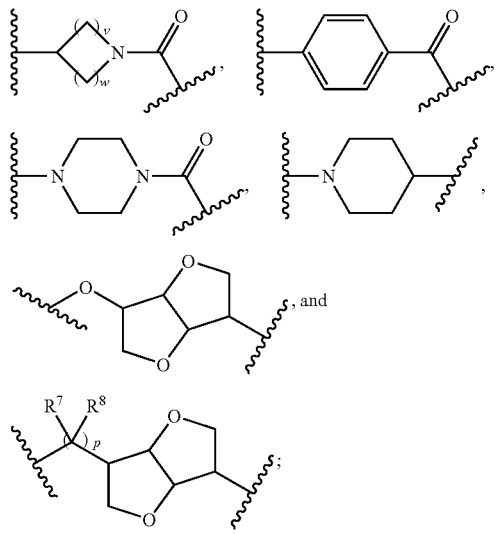

h, j, and k are independently selected from the group consisting of 0, 1, and 2;

m, n, x, y, and z are independently selected from the group consisting of 0, 1, 2, 3, and 4;

r and s are independently selected from the group consisting of 0, 1, 2, and 3, provided that r+s is 1, 2, 3 or 4.

2. A compound of claim 1, wherein the compound of Formula I is selected from the group consisting of

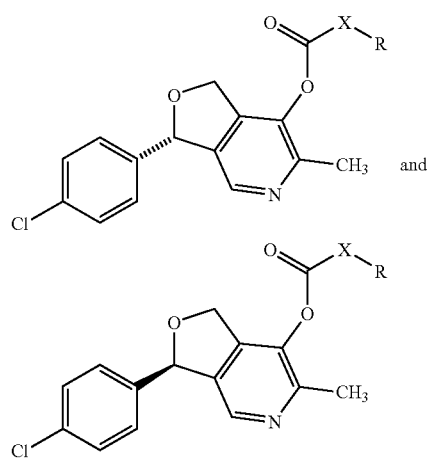

or a stereoisomer thereof, or a pharmaceutically acceptable salt thereof, or a pharmaceutically acceptable salt of the stereoisomer thereof.

3. A compound of claim 1, wherein X is selected from the group consisting of

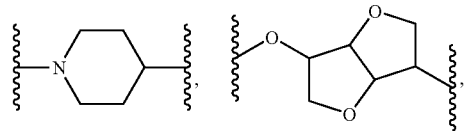

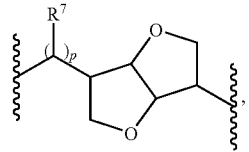

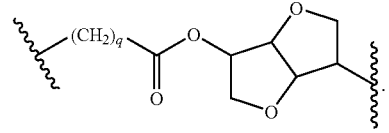

—NHCH₂(CH₂)$_n$CH₂OC(O)—, wherein n is 0, 1, 2, or 3,
—CH₂NHC(O)CH₂NHC(O)—, —CH₂OC(O)—,
—OCH(CH₃)OC(O)—, —OCH₂OC(O)—,
—CH₂CH₂C(O)NH—, —(CH₂)₅—, a bond,
—C(CH₃)₂—, —CH(CH₃)—, —C(CH₃)(CH₂ONO₂)—, —(CH₂)₂—, —(CH₂)₃—,
—CH₂—, —CH₂CH₂NHC(O)—, —CH₂NHC(O)—,
—CH(CH₂C₆H₅)NHC(O)—, —CH(CH₃)NHC(O)—,
—CH(CH(CH₃)₂NHC(O)—, —O—, —CH₂N(CH₃)C(O)—,

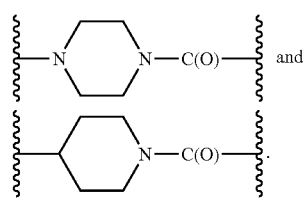

4. A compound of claim 1, wherein R is
—ONO₂, —O—CO—(CH₂)₃CH(ONO₂)CH₂(ONO₂),

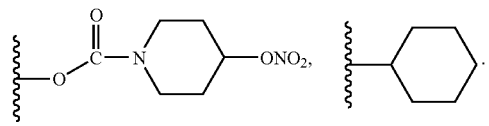

with the proviso that X is CR¹R³ and R³ is —CH₂ONO₂ or —ONO₂,
—(CH₂)₄ONO₂, —CH₂ONO₂, —(CH₂)₂ONO₂,
—(CH₂)₃ONO₂, —(CH₂)₂CH(CH₃)ONO₂,
—CH₂—CH(ONO₂)—C(CH₃)₂—CH₂ONO₂,
—CH₂CH(ONO₂)CH(CH₃)ONO₂, —(CH₂)₂CH(ONO₂)CH₂ONO₂, —(CH₂)₃CH(ONO₂)CH₂(ONO₂),
—(CH₂)₄CH(ONO₂)CH₂(ONO₂),

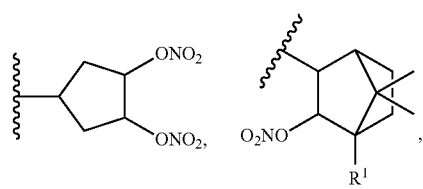

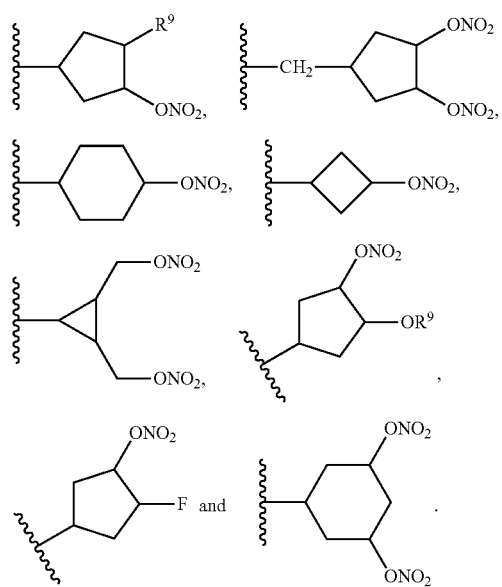
5. A compound of claim 1, wherein —X—R is selected from the group consisting of
—(CH₂)₅ONO₂, —C(CH₃)₂CH₂ONO₂, —CH(CH₃)(CH₂)₂ONO₂, —C(CH₃)(CH₂ONO₂)CH₂ONO₂,
—C(CH₃)₂(CH₂)₃ONO₂, —(CH₂)₂CH(CH₃)ONO₂, —(CH₂)₂CH(ONO₂)CH(CH₃)ONO₂,
—CH₂NHC(O)(CH₂)₂CH(ONO₂)CH(ONO₂)CH₃, CH₂NHC(O)(CH₂)₃CH(ONO₂)CH₂ONO₂,
—CH₂N(CH₃)C(O)(CH₂)₃CH(ONO₂)CH₂ONO₂, —O(CH₂)₄CH(ONO₂)CH₂ONO₂, —O(CH₂)₃ONO₂,
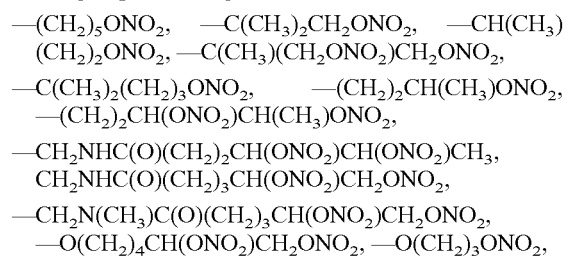
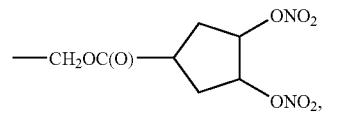
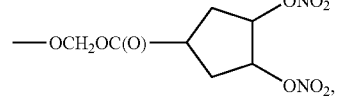
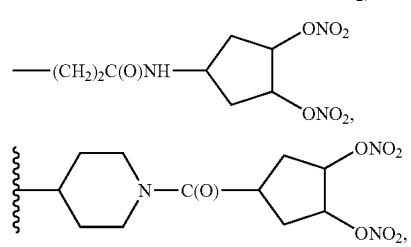
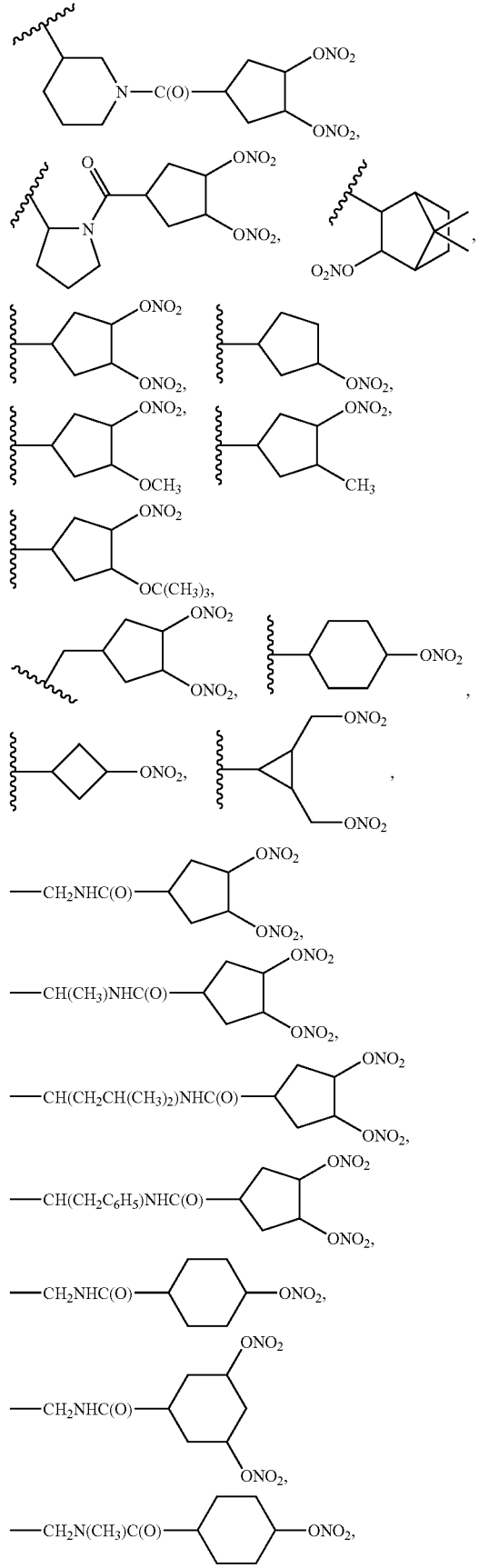

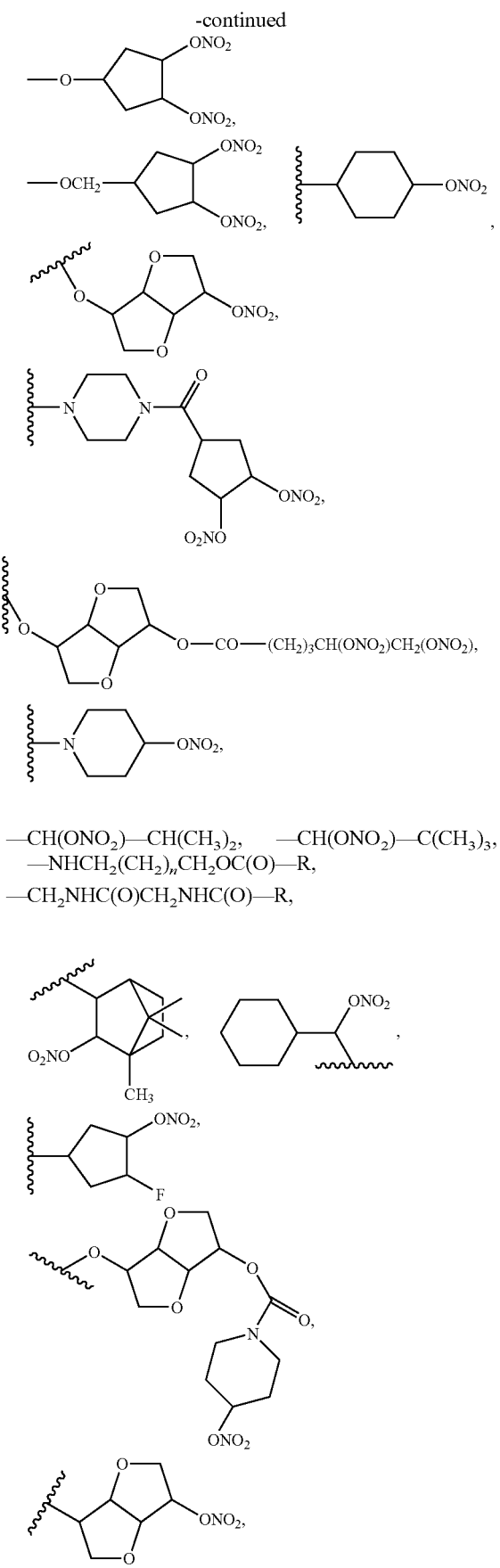
—CH(ONO$_2$)—CH(CH$_3$)$_2$,   —CH(ONO$_2$)—C(CH$_3$)$_3$,
—NHCH$_2$(CH$_2$)$_n$CH$_2$OC(O)—R,
—CH$_2$NHC(O)CH$_2$NHC(O)—R,
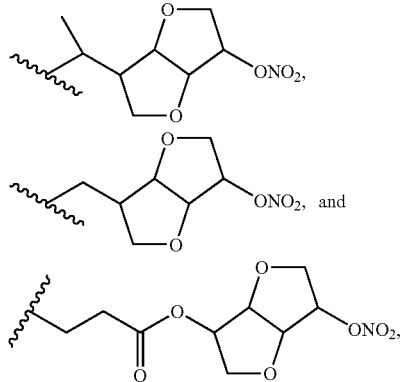
wherein n is 0, 1, 2 or 3.
6. A compound of claim 1, wherein —X—R is selected from the group consisting of
—(CH$_2$)$_5$ONO$_2$,   —C(CH$_3$)$_2$CH$_2$ONO$_2$,   —CH(CH$_3$)(CH$_2$)$_2$ONO$_2$, —C(CH$_3$)(CH$_2$ONO$_2$)CH$_2$ONO$_2$,
—C(CH$_3$)$_2$(CH$_2$)$_3$ONO$_2$,   —(CH$_2$)$_2$CH(CH$_3$)ONO$_2$,
—O(CH$_2$)$_4$CH(ONO$_2$)CH$_2$ONO$_2$, —O(CH$_2$)$_3$ONO$_2$,
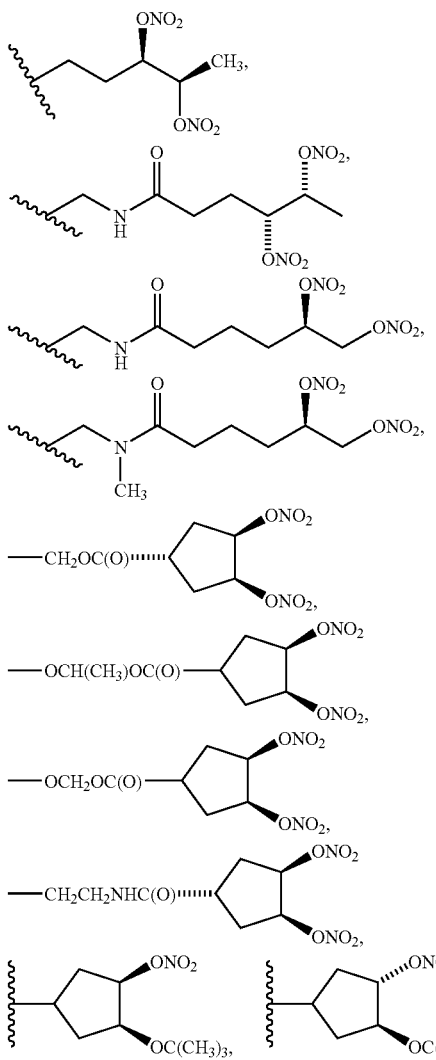

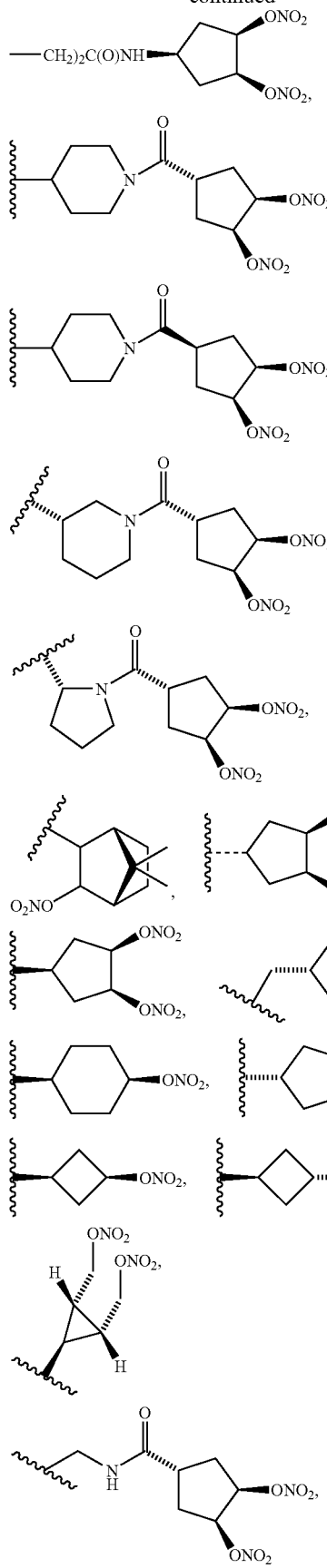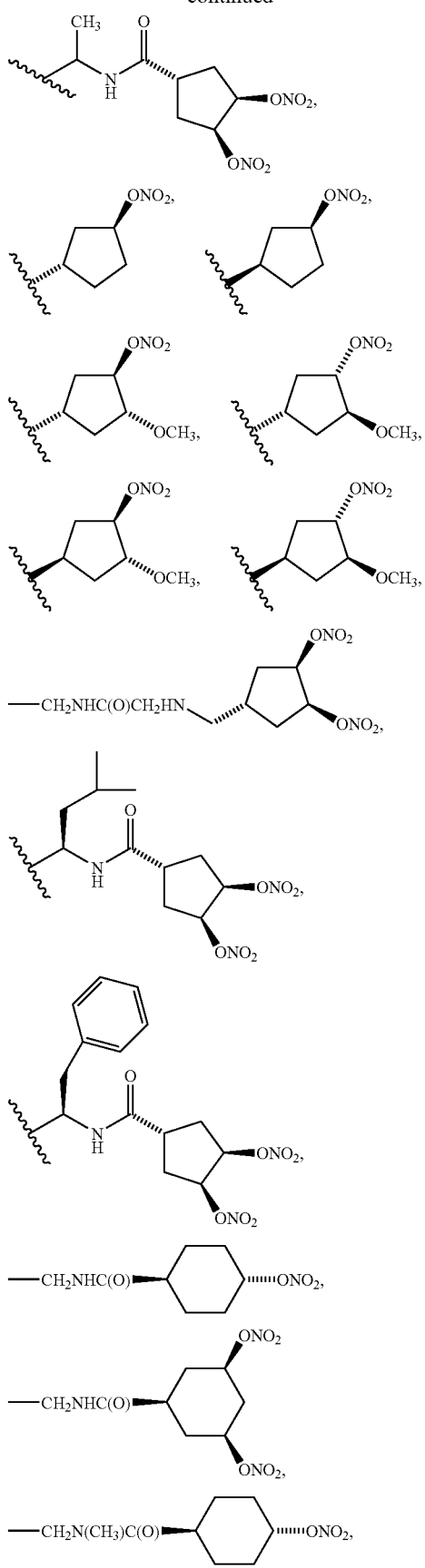

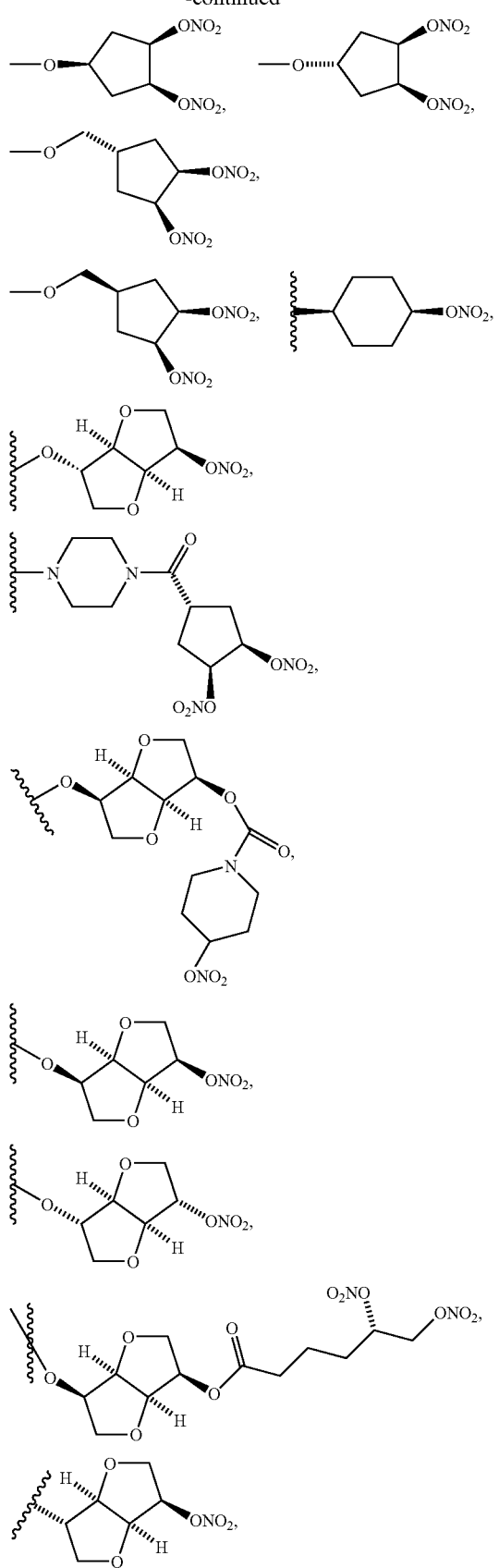

or a pharmaceutically acceptable salt thereof.

7. A compound of claim 1, selected from the group consisting of (3S)-3-(4-Chlorophenyl)-6-methyl-1,3-dihydrofuro[3,4-c]pyridin-7-yl 4-{[(1r,3R,4S)-3,4-bis(nitrooxy)cyclopentyl]amino}-4-oxobutanoate, 3-(4-chlorophenyl)-6-methyl-1,3-dihydrofuro[3,4-c]pyridin-7-yl(1s,3R,4S)-3,4-bis(nitrooxy)cyclopentanecarboxylate, 3-(4-chlorophenyl)-6-methyl-1,3-dihydrofuro[3,4-c]pyridin-7-yl(1r,3R,4S)-3,4-bis(nitrooxy)cyclopentanecarboxylate, (3S)-3-(4-chlorophenyl)-6-methyl-1,3-dihydrofuro[3,4-c]pyridin-7-yl(1s,3R,4S)-3,4-bis(nitrooxy)cyclopentanecarboxylate, (3R)-3-(4-chlorophenyl)-6-methyl-1,3-dihydrofuro[3,4-c]pyridin-7-yl(1s,3R,4S)-3,4-bis(nitrooxy)cyclopentanecarboxylate, (3S)-3-(4-chlorophenyl)-6-methyl-1,3-dihydrofuro[3,4-c]pyridin-7-yl(1s,3R,4S)-3,4-bis(nitrooxy)cyclopentanecarboxylate, 3-(4-chlorophenyl)-6-methyl-1,3-dihydrofuro[3,4-c]pyridin-7-yl 2,2-dimethyl-3-(nitrooxy)propanoate, 3-(4-chlorophenyl)-6-methyl-1,3-dihydrofuro[3,4-c]pyridin-7-yl 2-methyl-4-(nitrooxy)butanoate, 3-(4-chlorophenyl)-6-methyl-1,3-dihydrofuro[3,4-c]pyridin-7-yl 2-methyl-3-(nitrooxy)-2-[(nitrooxy)methyl]propanoate, 3-(4-chlorophenyl)-6-methyl-1,3-dihydrofuro[3,4-c]pyridin-7-yl 3-(nitrooxy)cyclopentanecarboxylate, 3-(4-chlorophenyl)-6-methyl-1,3-dihydrofuro[3,4-c]pyridin-7-yl 2,2-dimethyl-5-(nitrooxy)pentanoate, 3-(4-chlorophenyl)-6-methyl-1,3-dihydrofuro[3,4-c]pyridin-7-yl 4-(nitrooxy)pentanoate, 3-(4-chlorophenyl)-6-methyl-1,3-dihydrofuro[3,4-c]pyridin-7-yl[1s,3R,4S)-3,4-bis(nitrooxy)cyclopentyl]acetate, 3-(4-chlorophenyl)-6-methyl-1,3-dihydrofuro[3,4-c]pyridin-7-yl cis-4-(nitrooxy)cyclohexanecarboxylate, 3-(4-chlorophenyl)-6-methyl-1,3-dihydrofuro[3,4-c]pyridin-7-yl 2,2-dimethyl-5-(nitrooxy)pentanoate, 3-(4-chlorophenyl)-6-methyl-1,3-dihydrofuro[3,4-c]pyridin-7-yl(3R,4R)-3,4-bis(nitrooxy)cyclopentanecarboxylate, (3S)-3-(4-chlorophenyl)-6-methyl-1,3-dihydrofuro[3,4-c]pyridin-7-yl(4R,5R)-4,5-bis(nitrooxy)hexanoate, 3-(4-chlorophenyl)-6-methyl-1,3-dihydrofuro[3,4-c]pyridin-7-yl cis-3-(nitrooxy)cyclobutanecarboxylate, 3-(4-chlorophenyl)-6-methyl-1,3-dihydrofuro[3,4-c]pyridin-7-yl trans-3-(nitrooxy)cyclobutanecarboxylate, (3S)-3-(4-chlorophenyl)-6-methyl-1,3-dihydrofuro[3,4-c]pyridin-7-yl(1r,2R,3S)-2,3-bis[(nitrooxy)methyl]cyclopropanecarboxylate, (3S)-3-(4-chlorophenyl)-6-methyl-1,3-dihydrofuro[3,4-c]pyridin-7-yl N-{[(1s,3R,4S)-3,4-bis(nitrooxy)cyclopentyl]carbonyl}glycinate, (3S)-3-(4-chlorophenyl)-6-methyl-1,3-dihydrofuro[3,4-c]pyridin-7-yl N-{[(1s,3R,4S)-3,4-bis(nitrooxy)cyclopentyl]carbonyl}-D-alaninate, (3S)-3-(4-chlorophenyl)-6-methyl-1,3-dihydrofuro[3,4-c]pyridin-7-yl N-{[(1s,3R,4S)-3,4-bis(nitrooxy)cyclopentyl]carbonyl}-D-leucinate, (3S)-3-(4-chlorophenyl)-6-methyl-1,3-dihydrofuro[3,4-c]pyridin-7-yl N-{[1s,3R,4S)-3,4-bis(nitrooxy)cyclopentyl]carbonyl}-D-phenylalaninate, (1r,3R,4S)-3,4-Bis(nitrooxy)cyclopentyl (3S)-3-(4-chlorophenyl)-6-methyl-1,3-dihydrofuro[3,4-c]pyridin-7-yl carbonate, 5,6-Bis(nitrooxy)hexyl 3-(4-chlorophenyl)-6-methyl-1,3-dihydrofuro[3,4-c]pyridin-7-yl carbonate, 3-(4-Chlorophenyl)-6-methyl-1,3-dihydrofuro[3,4-c]pyridin-7-yl 3-(nitrooxy)propyl carbonate, (3S)-3-(4-Chlorophenyl)-6-methyl-1,3-dihydrofuro[3,4-c]pyridine-7-yl 4-{[(1s,3R,4S)-3,4-bis(nitrooxy)cyclopentyl]carbonyl}piperazine-1-carboxylate, (S)—((S)-3-(4-chlorophenyl)-6-methyl-1,3-dihydrofuro[3,4-c]pyridin-7-yl)2-cyclohexyl-2-(nitrooxy)acetate, (S)-3-(4-chlorophenyl)-6-methyl-1,3-dihydrofuro[3,4-c]pyridin-7-yl 2-(4,7,7-trimethyl-3-(nitrooxy)bicyclo[2.2.1]heptan-2-yl)acetate, (R)—((S)-3-(4-chlorophenyl)-6-methyl-1,3-dihydrofuro[3,4-c]pyridin-7-yl)3-methyl-2-(nitrooxy)butanoate, (S)—((S)-3-(4-chlorophenyl)-6-methyl-1,3-dihydrofuro[3,4-c]pyridin-7-yl)3,3-dimethyl-2-(nitrooxy)butanoate, (6R,6aS)-6-((3-(4-chlorophenyl)-6-methyl-1,3-dihydrofuro[3,4-c]pyridin-7-yloxy)carbonyloxy)hexahydrofuro[3,2-b]furan-3-yl 4-(nitrooxy)piperidine-1-carboxylate, 3-(4-chlorophenyl)-6-methyl-1,3-dihydrofuro[3,4-c]pyridin-7-yl 4-(nitrooxy)piperidine-1-carboxylate, (S)-((3R,3aR,6R,6aR)-6-(((S)-3-(4-chlorophenyl)-6-methyl-1,3-dihydrofuro[3,4-c]pyridin-7-yloxy)carbonyloxy)hexahydrofuro[3,2-b]furan-3-yl)5,6-bis(nitrooxy)hexanoate, (R)-((3S,3aR,6S,6aR)-6-(((S)-3-(4-chlorophenyl)-6-methyl-1,3-dihydrofuro[3,4-c]pyridin-7-yloxy)carbonyloxy)hexahydrofuro[3,2-b]furan-3-yl)5,6-bis(nitrooxy)hexanoate, (S)-3-(4-chlorophenyl)-6-methyl-1,3-dihydrofuro[3,4-c]pyridin-7-yl(3R,3aR,6R,6aS)-6-(nitrooxy)hexahydrofuro[3,2-b]furan-3-yl carbonate, (3S)-3-(4-chlorophenyl)-6-methyl-1,3-dihydrofuro[3,4-c]pyridine-7-yl(3S,3aR,6R,6aS)-6-(nitrooxy)hexahydrofuro[3,2-b]furan-3-yl carbonate, (3S)-3-(4-chlorophenyl)-6-methyl-1,3-dihydrofuro[3,4-c]pyridin-7-yl(1R,3S,4S)-3-methoxy-4-(nitrooxy)cyclopentanecarboxylate, (S)-3-(4-chlorophenyl)-6-methyl-1,3-dihydrofuro[3,4-c]pyridin-7-yl(3S,3aR,6S,6aS)-6-(nitrooxy)hexahydrofuro[3,2-b]furan-3-yl carbonate, 3-(4-Chlorophenyl)-6-methyl-1,3-dihydrofuro[3,4-c]pyridin-7-yl 4-(nitrooxy)butanoate, (3S)-3-(4-Chlorophenyl)-6-methyl-1,3-dihydrofuro[3,4-c]pyridin-7-yl 4-(nitrooxy)butanoate, (3R)-3-(4-Chlorophenyl)-6-methyl-1,3-dihydrofuro[3,4-c]pyridin-7-yl 4-(nitrooxy)butanoate, 1-[({[(3S)-3-(4-chlorophenyl)-6-methyl-1,3-dihydrofuro[3,4-c]pyridin-7-yl]oxy}carbonyl)oxy]ethyl(1s,3R,4S)-3,4-bis(nitrooxy)cyclopentanecarboxylate, (3S)-3-(4-Chlorophenyl)-6-methyl-1,3-dihydrofuro[3,4-c]pyridin-7-yl-oxycarbonyloxymethyl(1s,3R,4S)-3,4-bis(nitrooxy)cyclopentanecarboxylate, (3S)-3-(4-Chlorophenyl)-6-methyl-1,3-dihydrofuro[3,4-c]pyridin-7-yl-oxycarbonyl (1s,3R,4S)-3,4-bis(nitrooxy)cyclopentanecarboxylate,

[3-(4-chlorophenyl)-6-methyl-5-oxido-1,3-dihydrofuro[3,4-c]pyridin-5-ium-7-yl](3S,4R)-3,4-dinitrooxycyclopentanecarboxylate, (3S)-3-(4-chlorophenyl)-6-methyl-1,3-dihydrofuro[3,4-c]pyridin-7-yl(1R,3R)-3-(nitrooxy)cyclopentanecarboxylate, (3S)-3-(4-chlorophenyl)-6-methyl-1,3-dihydrofuro[3,4-c]pyridin-7-yl(1R,3R)-3-(nitrooxy)cyclopentanecarboxylate, (3S)-3-(4-chlorophenyl)-6-methyl-1,3-dihydrofuro[3,4-c]pyridin-7-yl(1R,3S)-3-(nitrooxy)cyclopentanecarboxylate, (3S)-3-(4-chlorophenyl)-6-methyl-1,3-dihydrofuro[3,4-c]pyridin-7-yl(1R,3S)-3-(nitrooxy)cyclopentanecarboxylate, (3S)-3-(4-chlorophenyl)-6-methyl-1,3-dihydrofuro[3,4-c]pyridin-7-yl(1R,3R,4R)-3-methoxy-4-(nitrooxy)cyclopentanecarboxylate, (3S)-3-(4-chlorophenyl)-6-methyl-1,3-dihydrofuro[3,4-c]pyridin-7-yl(1R,3R,4R)-3-methoxy-4-(nitrooxy)cyclopentanecarboxylate, (3S)-3-(4-chlorophenyl)-6-methyl-1,3-dihydrofuro[3,4-c]pyridin-7-yl(1R,3S,4S)-3-ethoxy-4-(nitrooxy)cyclopentanecarboxylate, (3S)-3-(4-chlorophenyl)-6-methyl-1,3-dihydrofuro[3,4-c]pyridin-7-yl(1R,3S,4S)-3-ethoxy-4-(nitrooxy)cyclopentanecarboxylate, (3S)-3-(4-chlorophenyl)-6-methyl-1,3-dihydrofuro[3,4-c]pyridin-7-yl(1R,3S,4S)-3-methoxy-4-(nitrooxy)cyclopentanecarboxylate, (3S)-3-(4-chlorophenyl)-6-methyl-1,3-dihydrofuro[3,4-c]pyridin-7-yl(1R,3S,4S)-3-methoxy-4-(nitrooxy)cyclopentanecarboxylate, (3S)-3-(4-chlorophenyl)-6-methyl-1,3-dihydrofuro[3,4-c]pyridin-7-yl(1S,3R,4R)-3-tert-butoxy-4-(nitrooxy)cyclopentanecarboxylate, (3S)-3-(4-chlorophenyl)-6-methyl-1,3-dihydrofuro[3,4-c]pyridin-7-yl(1S,3R,4R)-3-tert-butoxy-4-(nitrooxy)cyclopentanecarboxylate, (3S)-3-(4-chlorophenyl)-6-methyl-1,3-dihydrofuro[3,4-c]
  pyridin-7-yl(1R,3R,4R)-3-fluoro-4-(nitrooxy)cyclopentanecarboxylate,
(3S)-3-(4-chlorophenyl)-6-methyl-1,3-dihydrofuro[3,4-c]
  pyridin-7-yl(1R,3R,4R)-3-fluoro-4-(nitrooxy)cyclopentanecarboxylate,
(3S)-3-(4-chlorophenyl)-6-methyl-1,3-dihydrofuro[3,4-c]
  pyridin-7-yl(1S,3S,4R)-3-methoxy-4-(nitrooxy)cyclopentanecarboxylate, and
(3S)-3-(4-chlorophenyl)-6-methyl-1,3-dihydrofuro[3,4-c]
  pyridin-7-yl(1S,3S,4R)-3-methoxy-4-(nitrooxy)cyclopentanecarboxylate,
(S)-3-(4-chlorophenyl)-6-methyl-1,3-dihydrofuro[3,4-c]
  pyridin-7-yl(R)-3,3-dimethyl-2,4-bis(nitrooxy)butyl carbonate,
(S)-3-(4-chlorophenyl)-6-methyl-1,3-dihydrofuro[3,4-c]
  pyridin-7-yl(3S,3aR,6R,6aS)-6-(nitrooxy)hexahydrofuro[3,2-b]furan-3-yl succinate,
(S)-3-(4-chlorophenyl)-6-methyl-1,3-dihydrofuro[3,4-c]
  pyridin-7-yl(3R,3aR,6R,6aS)-6-(nitrooxy)hexahydrofuro[3,2-b]furan-3-yl succinate,
(S)-3-(4-chlorophenyl)-6-methyl-1,3-dihydrofuro[3,4-c]
  pyridin-7-yl(3S,3aR,6S,6aS)-6-(nitrooxy)hexahydrofuro[3,2-b]furan-3-yl succinate,
2,3-bis(nitrooxy)propyl(S)-3-(4-chlorophenyl)-6-methyl-1,3-dihydrofuro[3,4-c]pyridin-7-yl succinate, or a stereoisomer thereof, or a pharmaceutically acceptable salt thereof, or a pharmaceutically acceptable salt of the stereoisomer thereof.

8. A compound of claim 7, which is
(3S)-3-(4-chlorophenyl)-6-methyl-1,3-dihydrofuro[3,4-c]
  pyridin-7-yl(1R,3S,4S)-3-methoxy-4-(nitrooxy)cyclopentanecarboxylate, or a stereoisomer thereof, or a pharmaceutically acceptable salt thereof, or a pharmaceutically acceptable salt of the stereoisomer thereof.

9. A pharmaceutical composition comprising a compound of claim 8 and a pharmaceutically acceptable carrier.

10. A pharmaceutical composition comprising a compound of claim 1 and a pharmaceutically acceptable carrier.

11. A pharmaceutical composition comprising a compound of claim 1, a diuretic, and a pharmaceutically acceptable carrier.

12. A method for treating hypertension in a patient which comprises administering to the patient a therapeutically effective amount of the composition of claim 10.

* * * * *